(12) United States Patent
Weiss

(10) Patent No.: US 7,411,637 B2
(45) Date of Patent: Aug. 12, 2008

(54) SYSTEM AND METHOD FOR VARYING THE REFLECTANCE OR TRANSMITTANCE OF LIGHT

(75) Inventor: Victor Weiss, Rehovot (IL)

(73) Assignee: Elop Electro-Optics Industries Ltd., Rehovot (IL)

( * ) Notice: Subject to any disclaimer, the term of this patent is extended or adjusted under 35 U.S.C. 154(b) by 241 days.

(21) Appl. No.: 10/917,664

(22) Filed: Aug. 13, 2004

(65) Prior Publication Data

US 2005/0057701 A1    Mar. 17, 2005

Related U.S. Application Data

(63) Continuation of application No. PCT/IL03/00111, filed on Feb. 12, 2003.

(60) Provisional application No. 60/357,290, filed on Feb. 15, 2002.

(51) Int. Cl.
*G02F 1/1335* (2006.01)
*G02F 1/1347* (2006.01)
*G02F 1/1337* (2006.01)
*G02F 1/13* (2006.01)

(52) U.S. Cl. .............. 349/16; 349/11; 349/13; 349/77; 349/96; 349/129; 349/195

(58) Field of Classification Search .......... 349/16, 349/77
See application file for complete search history.

(56) References Cited

U.S. PATENT DOCUMENTS

| | | | |
|---|---|---|---|
| 4,660,937 A | 4/1987 | Richardson | |
| 4,671,617 A | 6/1987 | Hara | |
| 4,690,508 A | 9/1987 | Jacob | |
| 4,964,251 A * | 10/1990 | Baughman et al. | 52/171.3 |
| 5,015,086 A | 5/1991 | Okaue et al. | |
| 5,074,647 A | 12/1991 | Fergason et al. | |
| 5,113,270 A * | 5/1992 | Fergason | 349/87 |
| 5,113,271 A | 5/1992 | Fergason | |
| 5,694,188 A | 12/1997 | Sano et al. | |
| 5,841,499 A | 11/1998 | Baur et al. | |
| 6,239,778 B1 | 5/2001 | Palffy-Muhoray et al. | |
| 6,392,725 B1 * | 5/2002 | Harada et al. | 349/74 |

(Continued)

FOREIGN PATENT DOCUMENTS

DE    40 04 206 A1    2/1990

(Continued)

OTHER PUBLICATIONS

Patent Abstracts of Japan, Publication No. 02087122, published Mar. 28, 1990, Mitsubishi Kasei Corp., Abstract.

(Continued)

*Primary Examiner*—Michael H Caley
(74) *Attorney, Agent, or Firm*—Darby & Darby PC

(57) ABSTRACT

Device for transmitting light at variable intensity, the device including a front variable polarizer, polarizing incoming light at a first selected polarization level, in a first direction and a rear variable polarizer, optically coupled with the front variable polarizer, polarizing light exiting the front variable polarizer at a second selected polarization level, in a second direction, wherein the first selected polarization level and the second selected polarization level are substantially zero, when no substantial electric power is applied respectively, to the front variable polarizer and the rear variable polarizer.

57 Claims, 27 Drawing Sheets

U.S. PATENT DOCUMENTS 6,559,903 B2 * 5/2003 Faris et al. .................... 349/16
6,621,534 B2 * 9/2003 Lin et al. ...................... 349/16

FOREIGN PATENT DOCUMENTS

EP          1 158 336 A2    11/2001
WO     WO-02/06888 A1       1/2002

OTHER PUBLICATIONS

Takafumi Chiba, et al., "Polarization Stabilizer Using Liquid Crystal Rotatable Waveplates", Journal of Lightwave Technoloy, vol. 17, No. 5, May 1999, pp. 885-890.

I. Dozov, et al., "Nemoptic's Bistable Nematic Liquid-Crystal Technology", Nemoptic, Information Display—Jan. 2002, pp. 10-12.

I. Dozov, et al., "Fast bistable nematic display from coupled surface anchoring breaking", Laboratoire de Physique des Solides, Universite Paris-Sud.

S. Kato et al., "Study of Liquid Crystal Antiglare Mirros", SAE Technical Paper Series, 860639, Feb. 1986.

Shinya Ohmi et al., "Fall-Safe Type Liquid Crystal Mirror for Autombiles", SAE Technical Paper Series, 870637, Feb. 1987.

Guest-Host Displays.

* cited by examiner

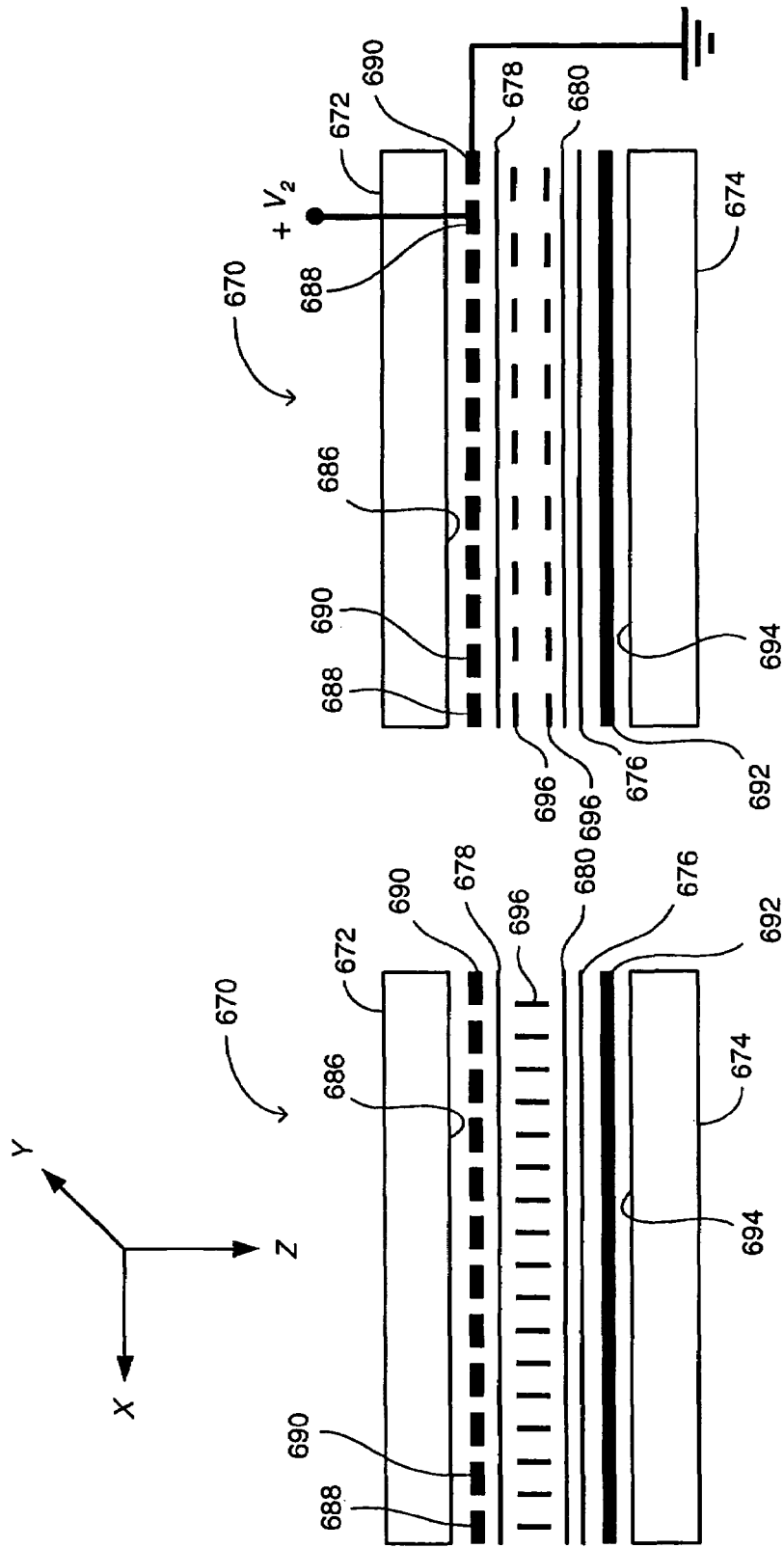

SYSTEM AND METHOD FOR VARYING THE REFLECTANCE OR TRANSMITTANCE OF LIGHT

FIELD OF THE DISCLOSED TECHNIQUE

The disclosed technique relates to electro-optic windows, mirrors or visor devices for incorporation in observation, viewing or display applications. More particularly, the disclosed technique relates to systems and methods, for providing variable light control in conjunction with emissive sources, and for providing reflectance or transmittance of light, based on non-conventional liquid crystal device (LC) technology.

BACKGROUND OF THE DISCLOSED TECHNIQUE

Systems and methods for varying the transmittance or reflectance of light are known in the art. Such systems are employed in automotive rear-view or side-view mirrors, automotive windows, spectacles, head-up displays (HUD), head-mounted displays (HMD), and the like.

Conventional automotive rear-view mirrors have a constant reflectance. Hence, a sudden increase in luminance, for example when the image of the headlamps of a vehicle approaching from behind is reflected toward the driver through the rear-view mirror, may temporarily blind the driver. This is especially disturbing during poor environmental lighting conditions, when the eyes of the driver have become accommodated to the reduced background luminance. In conventional viewing glasses, motorcycle or ski goggles, automotive windows, and the like, the operator is frequently exposed to excessive sun light, which may cause discomfort and even eye damage.

In HUD and HMD systems, the displayed information includes symbols, graphical or alphanumeric image components. Displaying this information on the field of view of the pilot, considerably reduces the physical tasks required during the flight, such as checking the flight instruments, aiming toward a target, landing, and the like. Similarly, in cameras or other visor assisted devices, assisting data (e.g., aiming, pointing, focusing or zooming data, exposure time, lens stop data, and the like) are superimposed on the external field of view. The operator of such devices should be able to perceive both the displayed data and the background view, without moving his eyes or head between the display and the outside scene. In conventional HUD and HMD, the background scene, which is illuminated by sunlight, is often of a very high luminance, up to several thousands of foot-Lamberts (fL), and furthermore, direct sunlight has a luminance even several orders of magnitude larger.

The term "contrast" herein below refers to the ratio of the luminance of two images at a certain viewing plane. When an image is displayed on a background scene, the contrast is equal to the ratio between the luminance of the displayed image and the sum of the luminances of the displayed image and the background scene. The higher the luminance of the background scene, the lower the contrast of the displayed image against the background scene. For example, the contrast of a displayed image having a luminance of 500 fL, which is displayed against a background scene having a luminance of 4000 fL, is about 11%. However, the same displayed image would have a contrast of about 40%, if displayed against a background scene having a luminance of 800 fL.

Hence, in such situations it is desirable to reduce the luminance of the background scene. Different techniques have been applied or proposed, for reducing the background luminance. One such technique employs a mechanism for switching between a plurality of fixed states, such as commonly applied in automotive rear-view mirrors. Other techniques employ a fixed, transparent light filter, similar to that used in sunglasses or sun visors, or a fixed opaque shield for reducing the viewing aperture, such as sun blinds. However, these devices reduce the visibility of the background scene under poor illumination.

Another technique for reducing background luminance employs auto-dimming mirrors (ADM) or variable transmittance optics (VTO) with real-time adaptive reflectance and transmittance, respectively. Mirrors or viewing glasses according to these techniques, exhibit variable reflection or transmission, respectively, whereby they can be manually or automatically switched to a dark state or a bright state, or switched between a plurality of intermediate states, which may either be continuous or discrete. The dark state, also referred to as the closed state, is the state of minimal transmittance or reflectance. The bright state, also referred to as the open state, is the state of maximal transmittance or reflectance.

Conventional ADM devices, according to one technique, include a VTO component, and a highly reflective surface. Light incident upon such a device, passes through the VTO component and is reflected by the reflective surface back to the VTO component, whereby the amount of light eventually reflected from the device depends on the state of the VTO component.

Electro-optic ADM and VTO devices may be either normally open (also referred to as normally bright), meaning they are in the open state when no electric field is applied, or normally closed (also referred to as normally dark), meaning they are in the open state when an electric field is applied. Normally open devices have the property that in case of power failure, the device continues to transmit or reflect the incident light, without substantially affecting the incident light. It is noted that this property may be critical in human eye related applications, such as automotive rear-view mirrors or windows, wherein the driver has to be able to view the images through the device, at all times. The contrast ratio, also referred to as the dynamic range, is equal to the ratio of the maximal and minimal obtainable transmittance or reflectance values of the VTO or ADM device, respectively.

VTO and ADM techniques have employed various elements, such as photochromic (PhC) materials, electrochromic (EC) cells, suspended particle technology and conventional liquid crystal (LC) technology. PhC materials have a limited spectral and photochemical sensitivity. Hence, devices using these materials are highly dependent on the incidence of strong ultraviolet illumination thereupon.

EC and SP cells have relatively large response times, typically in the order of seconds to minutes, and hence, they are not normally employed in rapidly-changing illumination conditions. Furthermore, EC materials exhibit a memory effect in their dark state, and hence, devices employing these materials require a special reverse drive circuit in order to return to the transparent default state. SP cells are normally dark by nature, and hence are applicable only to normally dark devices.

There are several conventional ADM and VTO techniques which employ the LC technology. A device, according to one such technique, includes an LC pane sandwiched between two crossed polarizers. The transmittance of the device depends on the state of the LC pane, which may be controlled by an electric field applied thereto. However, a polarizer absorbs at least 50% of unpolarized incident light, thereby determining the open state transmittance to be no more than 50%.

U.S. Pat. No. 5,015,086 issued to Okaue et al., and entitled "Electronic Sunglasses", is directed to electronically controlled sunglasses utilizing conventional LC technology and powered by a solar cell. According to embodiment 1 of the disclosure, the LC panel used has a film substrate including an electrode surface and a nematic liquid crystal having a proper amount of right-spinning chirality material. Light-polarizing plates are pasted on both sides of the film substrate, with the absorption axes of these light-polarizing plates matching the rubbing direction of the film substrate. The maximal transmittance of the transmittance varying section is 35%.

Another technique which employs LC technology, alleviates the polarizer dependent light loss by using dichroic or pleochroic guest-host liquid crystal (GH-LC) mixtures, whereby no polarizers are needed. Devices according to these techniques, especially those with normally open cells, have generally yielded poor contrast ratios.

U.S. Pat. No. 4,660,937 issued to Richardson, and entitled "Dichroic Dye-Nematic Liquid Crystal Mirror", is directed to an auto-dimming mirror, which utilizes a liquid crystal containing a dichroic dye. The auto-dimming mirror includes a liquid crystal material enclosed by a seal, a reflective surface, an electrically conducting layer and transparent front and back members on each side of the liquid crystal material. The auto-dimming mirror may be either normally open or normally closed, depending on whether the liquid crystal has positive or negative anisotropy and whether the dichroic dye is positive or negative. The dynamic range reported was about 3.7 for the normally closed embodiment, and about 1.3 for the normally open embodiment.

U.S. Pat. No. 6,239,778 issued to Palffy-Muhoray et al., and entitled "Variable Light Attenuating Dichroic Dye Guest-Host Device", is directed to a VTO cell which utilizes a host material and a light absorbing dichroic dye guest. A solution of dichroic dye and a liquid crystalline material is disposed between two transmissive substrates, whose inner surfaces are coated with an electrically conducting layer. Each side of the VTO cell further includes an alignment layer and a passivation or insulating layer. The electrically conducting layers are connected to a power circuit, which includes a variable voltage supply controlling the transmittance of the cell.

European Patent Application Publication No. EP1158336A2 to Weiss et al., and entitled "System and Method for Varying the Transmittance of Light Through a Media", discloses a system and method for varying the transmittance through selected portions of a media, on which images are displayed. The system includes a VTO media made of a non-conventional LC material, such as a dichroic dye GHLC. In one embodiment of the disclosed system, a double cell configuration is applied. Accordingly, two VTO cells are applied, which have mutually perpendicular LC director orientations, thereby effectively behaving as two crossed polarizers when no voltage is applied. When a voltage is applied, each of the cells switches to a homeotropic phase, with the director orientation perpendicular to the cell surface, thereby minimizing the dichroic dye absorption. Thus, the double-cell configuration may be used for a normally closed VTO cell.

U.S. Pat. No. 4,690,508 issued to Jacob and entitled "Liquid Crystal Closed-Loop Controlled Mirror Systems", is directed to a rear view mirror system of an automotive vehicle, which reflects light at variable intensities. The rear view mirror system includes a mirrored reflecting surface, a liquid crystal unit, two light sensors, a pair of adjustment devices and an electronic circuit, all located within a housing. The mirrored reflecting surface is located behind the liquid crystal unit and tilted with respect to the liquid crystal unit. One of the light sensors detects ambient light and the other light sensor detects the light which reaches the mirrored reflecting surface after passing through the liquid crystal unit. The mirrored reflecting surface is tilted with respect to the liquid crystal unit, thereby preventing first surface reflections from the liquid crystal unit to from reaching the driver, where the mirrored reflecting surface was substantially parallel with the liquid crystal unit.

The electronic circuit changes the opaqueness of the liquid crystal unit in a closed control loop, according to signals received from the two light sensors, thereby changing the intensity of the light which is reflected by the mirrored reflecting surface. When the intensity of the incident light to the liquid crystal unit increases, the electronic circuit increases the opaqueness of the liquid crystal unit. Conversely, when the intensity of the incident light to the liquid crystal unit decreases, the electronic circuit decreases the opaqueness of the liquid crystal unit. When the ambient light changes from brighter to darker, the electronic circuit increases the opaqueness of the liquid crystal unit. Conversely, when the ambient light changes from darker to brighter, the electronic circuit decreases the opaqueness of the liquid crystal unit. The driver can change the opaqueness of the liquid crystal unit manually, by the pair of adjustment devices.

International Publication No. WO 02/06888 A1 published on 24 Jan. 2002 and entitled "Bistable Liquid Crystal Devices", is directed to methods to change the direction of alignment of the molecules of a liquid crystal device. The liquid crystal device includes a layer of liquid crystal material containing a dichroic additive, sandwiched between a first substrate and a second substrate. The surface of the first substrate is treated in order to introduce surface profiles having different azimuthal directions and thus provide azimuthal bistable surface alignment. The profiles can be 90 degrees apart. The surface of the second substrate is rubbed in order to provide planar alignment.

Linearly polarized light which strikes the first surface applies a torque to the molecules of the liquid crystal material. When an electric field is applied across the liquid crystal device, the molecules produce a homeotropic orientation. When the electric field is removed, the alignment of the first substrate relaxes to the direction of polarization of the linearly polarized light. This alignment is transferred to the second substrate, such that all molecules of the liquid crystal material are aligned in the direction of polarization of the linearly polarized light, even after removal of the linearly polarized light. When a dye or a light absorptive material is incorporated with the liquid crystal material, the linearly polarized light induces local heating, which assists the alignment of the molecules with the direction of polarization of the linearly polarized light.

A report published by Dozov et al., and entitled "Fast Bistable Nematic Display From Coupled Surface Anchoring Breaking", is directed to a bistable nematic liquid crystal, whose structure can be switched between a uniform (untwisted) stable state and a twisted stable state. This report is published in collaboration with SFIM-ODS SPIE Vol. 3011115 027-786X/97 p 61-69.

The bistable nematic liquid crystal in the uniform state, operates as a half-wave plate, so that if the bistable nematic liquid crystal is located between crossed polarizers, maximum light is transmitted. In the twisted state, the bistable nematic liquid crystal operates as an isotropic chiral optical system which introduces a relatively small rotation of the polarization (i.e., 10-30 degrees). Thus, with crossed polarizers, the bistable nematic liquid crystal in the twisted state is relatively dark.

In the uniform state, the molecules of the bistable nematic liquid crystal are uniformly parallel with the two plates of the bistable nematic liquid crystal. In the twisted state, only the layer of the molecules adjacent to the two plates are parallel to each plate and the other molecules are twisted between the two layers, thereby providing a twist of 180 degrees. The bistable nematic liquid crystal can be switched to the twisted state while passing through a homeotropic intermediate state, by applying a rapidly decreasing electric field. The bistable nematic liquid crystal can be switched to the uniform state while passing through the homeotropic intermediate state, by applying a slowly decreasing or a stepwise electric field.

SUMMARY OF THE DISCLOSED TECHNIQUE

It is an object of the disclosed technique to provide a novel method and system for transmitting and reflecting light at variable intensity, which overcome the disadvantages of the prior art.

In accordance with the disclosed technique, there is thus provided a device for transmitting light at variable intensity. The device includes a front variable polarizer and a rear variable polarizer, optically coupled with the front variable polarizer. The front variable polarizer applies substantially no polarization to incoming light and transmits the incoming light as an outgoing light, when substantially no electric field is applied across the front variable polarizer. The front variable polarizer polarizes the incoming light in a first direction, thereby producing a polarized incoming light, when an electric field is applied across the front variable polarizer.

The rear variable polarizer applies substantially no polarization to the outgoing light, when substantially no electric field is applied across the rear variable polarizer. The rear variable polarizer polarizes the polarized incoming light in a second direction, when an electric field is applied across the rear variable polarizer. Thus, each of the front variable polarizer and the rear variable polarizer operates as a normally open variable polarizer. A controller which is coupled with the front variable polarizer and with the rear variable polarizer, sets each of the front variable polarizer and the rear variable polarizer, to a selected polarization level.

In accordance with another aspect of the disclosed technique, there is thus provided a device for transmitting light at a variable intensity. The device includes a front variable polarizer, a rear variable polarizer, and at least one controllable optical phase shifter, located between the front variable polarizer and the rear variable polarizer. The front variable polarizer polarizes incoming light at a first selected polarization level, in a first direction. The rear variable polarizer is optically coupled with the front variable polarizer. The controllable optical phase shifter shifts the relative phase between two linearly polarized components of light which exits the front variable polarizer, by a selected phase shift. The rear variable polarizer polarizes light received from the controllable optical phase shifter, at a second selected polarization level, in a second direction.

In accordance with a further aspect of the disclosed technique, there is thus provided a method for transmitting light at variable intensity. The method includes the procedure of transmitting incoming light by a first variable polarizer toward a second variable polarizer, when no electric field is applied across the first variable polarizer. The method further includes the procedure of applying a first selected polarization to incoming light by the first variable polarizer, when an electric field is applied across the first variable polarizer.

The method further includes the procedure of transmitting light exiting the first variable polarizer, by the second variable polarizer, when no electric field is applied across the second variable polarizer. The method further includes the procedure of applying a second selected polarization to the light exiting the first variable polarizer, by the second variable polarizer, when an electric field is applied across the second variable polarizer.

In accordance with another aspect of the disclosed technique, there is thus provided an apparatus for viewing an image at variable intensity. The apparatus includes an optical assembly and a variable transmitter. The variable transmitter includes a front variable polarizer and a rear variable polarizer, optically coupled with the front variable polarizer.

BRIEF DESCRIPTION OF THE DRAWINGS

The disclosed technique will be understood and appreciated more fully from the following detailed description taken in conjunction with the drawings in which:

FIG. 15B is a schematic illustration of cross section IV of the variable polarizer of FIG. 15A, when no electric voltage is applied across the interdigitating electrodes and the planar electrode of the protective layers of the variable polarizer of FIG. 15A;

FIG. 15C is a schematic illustration of cross section IV of the variable polarizer of FIG. 15A, operating in an in-plane mode;

DETAILED DESCRIPTION OF THE EMBODIMENTS

Figure 1A:
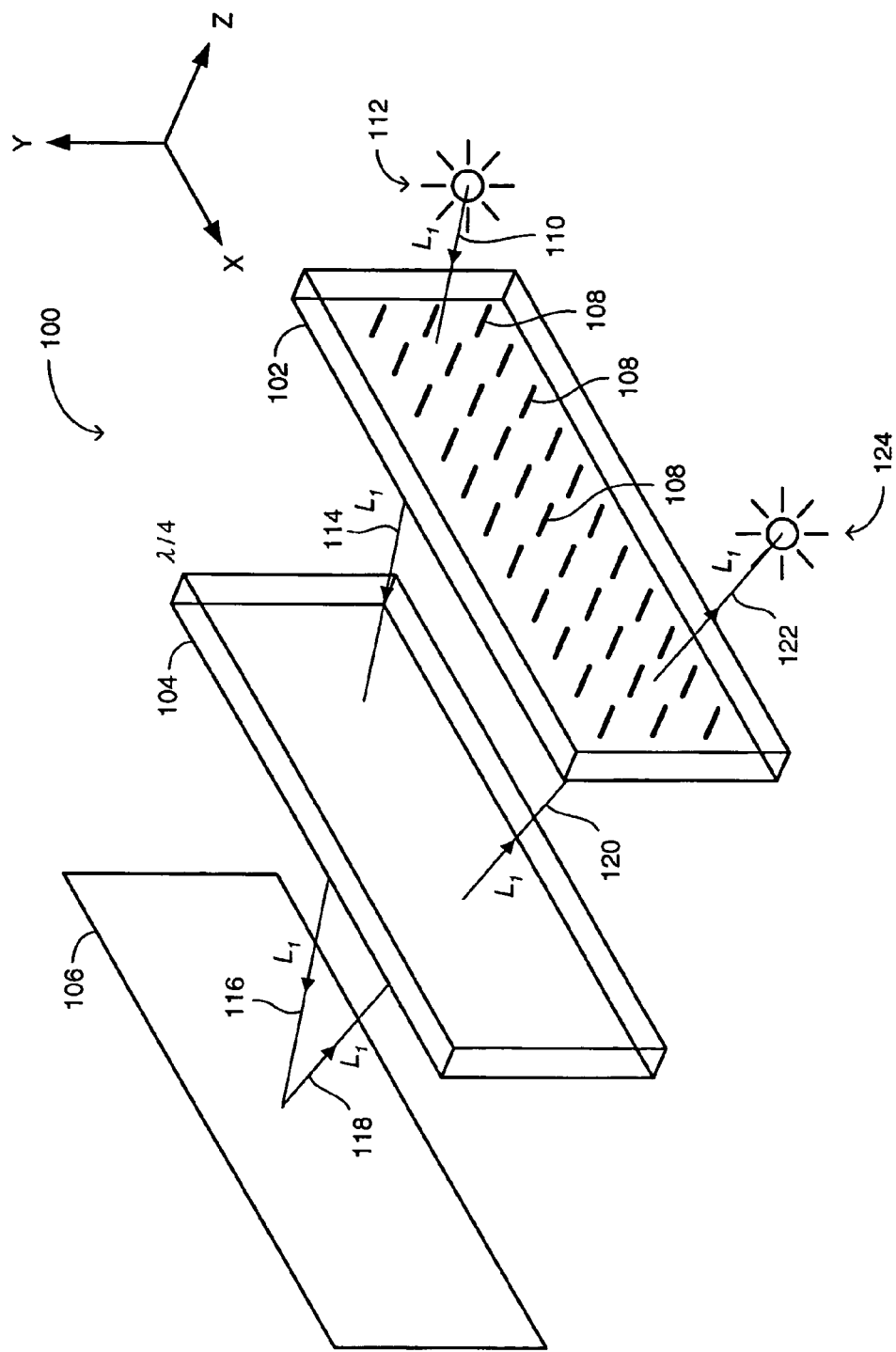
FIG. 1A is a schematic perspective view of a variable reflector, constructed and operative in accordance with an embodiment of the disclosed technique.

The disclosed technique overcomes the disadvantages of the prior art by providing a novel optical reflecting structure, which directs incoming light through a variable polarizer, followed by rotating the polarization of a portion of that light by a quarter of a circle and redirecting the rotated light back toward the variable polarizer. Every time incident light passes through a variable polarizer, the luminance thereof falls to an extent which depends on the polarization of the incident light, the orientation of the variable polarizer and the level of polarization to which the variable polarizer is set.

The level of dichroism of the variable polarizer dictates the polarization level of the variable polarizer at that time. Dichroism level is defined with respect to a specific direction of the variable polarizer. For example, assume that $A_x$ and $A_y$ are the amplitudes of the X and Y components, respectively, of the electromagnetic wave of a light beam entering a variable polarizer, and $A'_x$ and $A'_y$ are the magnitudes of the respective components of the electromagnetic wave of that light beam as it exits the variable polarizer. Then a measure of the dichroism level $D_x$ may be given with respect to the X axis as:

$$D_x = (T_x - T_y)/(T_x + T_y), \quad (1)$$

wherein $$T_y = \frac{A'_y}{A_y} \quad (2)$$

$$T_x = \frac{A'_x}{A_x} \quad (3)$$

and wherein it is assumed that $$T_x > T_y \geq 0. \quad (4)$$

Similarly, $$D_y = (T_y - T_x)/(T_x + T_y) \quad (5)$$

when $$T_y > T_x \geq 0. \quad (6)$$

It is noted that in the description herein below, the relative and absolute values of different parameters, such as luminance, electric field, voltage, dichroism, polarization level, direction, orientation angle, and the like, are approximate values and not precise values.

An "optical phase shifter" is an optical element which either retards or advances the phase of at least one linearly polarized component of an incoming light beam relative to another linearly polarized component thereof or to a reference light beam. It is noted that any monochromatic light beam, may be represented as a combination of two linearly polarized components, whose electromagnetic fields oscillate in orthogonal directions. The phase change can be any value between zero and $2\pi$ radians, and integer multiples thereof.

One type of optical phase shifter, which is called a wave plate, retards one linearly polarized component of an incoming light beam, with respect to the other linearly polarized component of that incoming light beam, by a fraction of a wavelength (e.g., $\lambda/8$, $\lambda/4$, $3\lambda/8$, $\lambda/n$, and the like). A $\lambda/4$ wave plate is an example of such a wave plate, also known as a quarter-wave plate. A $\lambda/4$ wave plate retards one linearly polarized component of an incoming light beam having a certain wavelength $\lambda$, by a quarter of wavelength $\lambda/4$, with respect to the other linearly polarized component of that incoming light beam. As a result, a linearly polarized incoming light beam which is linearly polarized at 45 degrees relative to the axes of the $\lambda/4$ wave plate, shall exit circularly polarized. Similarly, a circularly polarized incoming light beam shall exit the λ/4 wave plate, linearly polarized at 45 degrees relative to the axes of the λ/4 wave plate.

The disclosed technique is applicable for monochromatic light as well as for polychromatic light. It is noted that a wave plate is generally intended for a specific wavelength λ. However, the wave plate still provides approximately the same effect for wavelengths near λ. For example, if the device is intended for sunlight, a wave plate intended for a 550-nm wavelength (i.e., approximately the average wavelength of the sunlight spectrum) can be used.

The term "variable polarizer" herein below, refers to an optical element, whose polarization level can be varied between zero and a predetermined level of polarization, by varying the electric field applied thereto. Such a variable polarizer includes a light affecting substance, which is a combination of an optically active substance and anisotropic light absorbing particles. In the description herein below, the term "light affecting substance" refers to a substance which applies a polarization level to the incoming light, depending on the direction (i.e., the director) along which the anisotropic light absorbing particles are aligned. An optically active substance is one which affects the polarization direction or components of the incoming light, while having substantially no effect on the intensity of the incoming light. Such an optically active substance can be for example, liquid crystal, liquid crystal polymer, birefringent crystal, bireferingent polymer, bireferingent plastic, and the like.

The anisotropic light absorbing particles can be for example, dichroic dye molecules, dichroic microcrystals, pleochroic dye stuff, and the like. Each of dichroic or pleochroic dyes is composed of linear, rod-shaped molecules having large anisotropic absorbance, wherein the anisotropic absorbance depends on the orientation of the rod-shaped molecules relative to the direction of the incident light and the incident light polarization. The anisotropic light absorbing particles are aligned along the director (i.e., the direction of the molecules of the optically active substance) at all times.

Preferably, the liquid crystal (i.e., the host) is coupled with the dichroic or pleochroic dye (i.e., the guest), by mixing the dye in the liquid-crystal phase, referred to herein below as "guest-host liquid crystal (GHLC) phase". In the description herein below, the guest molecules and the host molecules are assumed to be rod-shaped. When these dye molecules are mixed within a nematic liquid crystal phase, the dye molecules are aligned along the liquid crystal phase director, and as a result, the dye molecules exhibit switchable absorbance, switchable polarization and switchable reflectance or transmittance.

The variable polarizer can be either a continuously powered device or an intermittently powered device. In case of the continuously powered device, the orientation of the rod-shaped molecules (i.e., the dye molecules) is set at a predetermined direction, by continuously applying an electric field at a respective predetermined value, thereby setting the continuously powered device at a predetermined polarization level.

For example, when the electric field is applied, the rod-shaped molecules are uniformly aligned perpendicular to the boundary surfaces of the variable polarizer (i.e., the variable polarizer is in a homeotropic state). On the contrary, when no electric field is applied, the rod-shaped molecules are uniformly aligned parallel with the boundary surfaces of the variable polarizer (i.e., the variable polarizer is in a planar state). Thus, by applying different electric fields to the light affecting substance of the variable polarizer, the variable polarizer applies different polarization levels to the incident light. A homeotropic alignment layer aligns the rod-shaped molecules in a direction perpendicular to the boundary surfaces of the variable polarizer, while a planar alignment layer aligns the rod-shaped molecules in a direction parallel with the boundary surfaces of the variable polarizer.

In case of an intermittently powered device, the variable polarizer can be set at the homeotropic, planar, or at at least one stable intermediate state, by applying a momentary electric field pulse having a predetermined pulse shape. A multi-stable liquid crystal cell has at least two stable states, each stable state having a predetermined liquid crystalline structure. Each structure has a predetermined ground state energy (i.e., energy well). Thus, by applying an electric field at a predetermined activation energy, which exceeds a respective predetermined energy barrier, the multi-stable cell transfers from one structure to another.

The multi-stable cell can be manufactured by applying a mixed planar and homeotropic surface alignment procedure. Each stable state corresponds to a predetermined anchoring strength respective of the rod-shaped molecules (i.e., at each stable state the rod-shaped molecules are anchored to the boundary surface of the cell, at a predetermined strength). When the structure of the light affecting substance is in the homeotropic state, the incident light passes there through without being affected in any manner. When the structure of the light affecting substance is in the planar state, only the component of light, which is linearly polarized in the direction of the rod-shaped molecules, passes through.

A "controllable optical phase shifter" is a device, which can operate in a plurality of phase shifting states, which may include a non-phase shift state as well (i.e., applying no phase shift to light).

A controllable optical phase shifter can be in the form of a multi-stable optical phase shifter, having a plurality of stable states (i.e., states which are maintained, without the application of an electric field or any other form of energy). It is noted that a multi-stable optical phase shifter may further be maintained at a plurality of unstable states, by applying different electric fields, thereto.

For example, the controllable optical phase shifter can be in the form of a bi-stable (i.e., having two stable states) twisted nematic liquid crystal, a bi-stable polymer stabilized liquid crystal, a bi-stable surface stabilized liquid crystal, and the like, having a selected thickness, and herein below referred to as "bi-stable optical phase shifter". The structure of the bi-stable optical phase shifter can be switched between an untwisted (or uniform) state and a twisted state, by applying a momentary electric field having a predetermined pulse shape. The type of the bi-stable optical phase shifter (e.g., λ/4 wave plate, λ/2 wave plate, and the like), depends on the thickness thereof. Alternatively, a controllable optical phase shifter can be in the form of a switchable optical phase shifter, as described herein below in conjunction with FIG. 4.

For example, when the structure of the twisted nematic liquid crystal is in the untwisted state, the bi-stable optical phase shifter operates as a λ/2 wave plate. When the structure of the twisted nematic liquid crystal is in the twisted state, the bi-stable optical phase shifter passes the incident light without having any effect thereon. The twisted nematic liquid crystal can be switched from the untwisted state to the twisted state, by applying a short duration pulse of electric field and from the twisted state to the untwisted state, by applying a slowly decreasing or a stepwise decreasing pulse of electric field.

The phase distribution of the light affecting substance is divided to two classes. Class 1 (or dispersed phase) is a liquid phase which consists of randomly dispersed and randomly oriented microphases such as GHLC droplet (GH-PDLC) or GHLC microdomains, which are embedded in polymer matrices. Class 2 (or homogeneous phase) is another liquid phase which consists of a homogeneous GHLC phase, which can be derived from liquid crystal materials and phases of nematic, twisted nematic, supertwisted nematic, cholesteric, smectic phases, other phases, and combinations or mixtures thereof.

Each of class 1 and class 2 GHLC phase distributions, can be either in form of a mixture or a chemical compound. In a mixture, the dichroic dye molecules (i.e., the guest molecules) are mixed at a small concentration (approximately 1-3%), in the liquid crystal (i.e., the host molecules). In a chemical compound, the anisotropic light absorbing particles and the light affecting substance molecules are coupled together in a chemical bond, such as covalent bonds, van der Waals bonds, Hydrogen bonds, electrostatic bonds, ionic bonds, and the like.

The various types of class 1 light affecting substances used in the disclosed technique, may include Guest-Host Polymer Dispersed Liquid Crystal (GH-PDLC), Dichroic Polymer Dispersed Liquid Crystal and their subclasses such as Polymer Stabilized Cholesteric Texture (PSCT) Liquid Crystal, and Nematic Curved Aligned Polymeric (NCAP) Liquid Crystal.

Class 1 GHLC structures usually exhibit inherent light scattering due to refractive index anisotropy of the liquid crystal phase relative to the surrounding phase. Accordingly, in class 1 GHLC, the inherent light scattering has to be eliminated or reduced to negligible levels, especially for visor-type applications. This may be accomplished by applying the GHLC phase to a liquid crystal material of very small birefringence, based on small dielectric anisotropy, with the average liquid crystal index being close to the surrounding polymer phase. In such cases, the refractive index anisotropy between the ordinary index and the extraordinary index is substantially small (e.g., smaller than 0.1), so that light scattering is greatly reduced. The reduction in light scattering may also be accomplished by defining the size of the microdroplets or microdomains, to be significantly smaller than the wavelength of the interacting light. The systems are dominantly absorption-modulated, leading to the desired ADM and VTO characteristics.

The structure of the microphase or droplet distribution of class 1 GH-PDLC is preferably non-spherical, having an anisotropic geometry, such as elliptical, sheared geometry, elongated geometry, and the like. In this manner it is possible to render the liquid crystal phase in the droplets at a preferred orientation, which may be further employed in the context of the disclosed technique, for increasing the contrast of single or multiple layers of variable polarizers, as described herein below.

A class 2 structure can be a Guest-Host (GH) dichroic liquid crystal incorporating a homogeneous nematic phase (Heilmeier), a cholesteric phase (White-Taylor), a multistable phase, and the like. In class 2 variable polarizers, dichroic dye guests are mixed with the homogenous liquid crystal phase hosts. Media utilizing these kinds of materials usually have the property of pure absorption-modulated images, without any light scattering. A normally closed GHLC can be formed for example, by mixing dichroic dyes of suitable dipole moments in a positive dielectric anisotropy twisted nematic GHLC cell. This cell has the liquid crystal phase in the twisted planar texture in the absence of an electric field, producing a normally closed type variable polarizer. This cell can be switched, by the application of an electric field, to the homeotropic phase, thus yielding an open state.

In a similar fashion, mixing suitable dichroic dyes in a GHLC cell of negative dielectric anisotropy, shall produce a normally open type variable polarizer. However, this type of cell conventionally yields poor contrast, and therefore it is impractical for some applications due to the fact that the liquid crystal phase obtained under the electric field is not a pure planar texture, and therefore yields negligible polarization.

A normally open variable polarizer can be constructed by adding a small amount of cholesteric liquid crystal to the nematic GHLC mixture, and applying a mixed homeotropic and planar surface alignment process. This surface alignment process allows the rod-shaped molecules to align substantially in the same direction, when an electric field is applied to the liquid crystal (i.e., the guest-host director is well defined when an electric field is applied). Thus, significant contrast is obtained, especially in a double cell configuration, together with a normally clear (open) VTO.

Figure 1B:
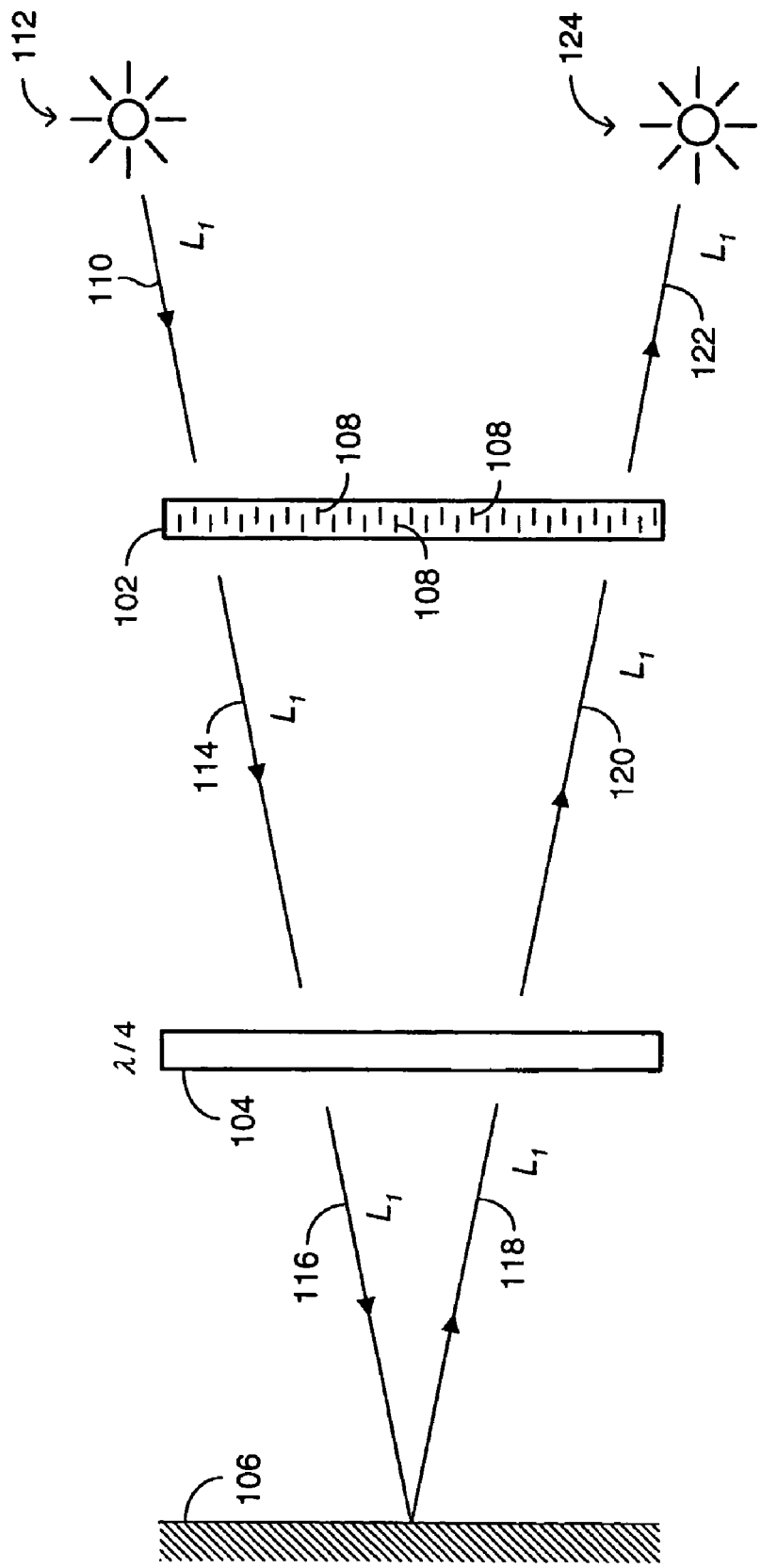
FIG. 1B is a schematic illustration of a side view of the variable reflector of FIG. 1A.
Figure 1C:
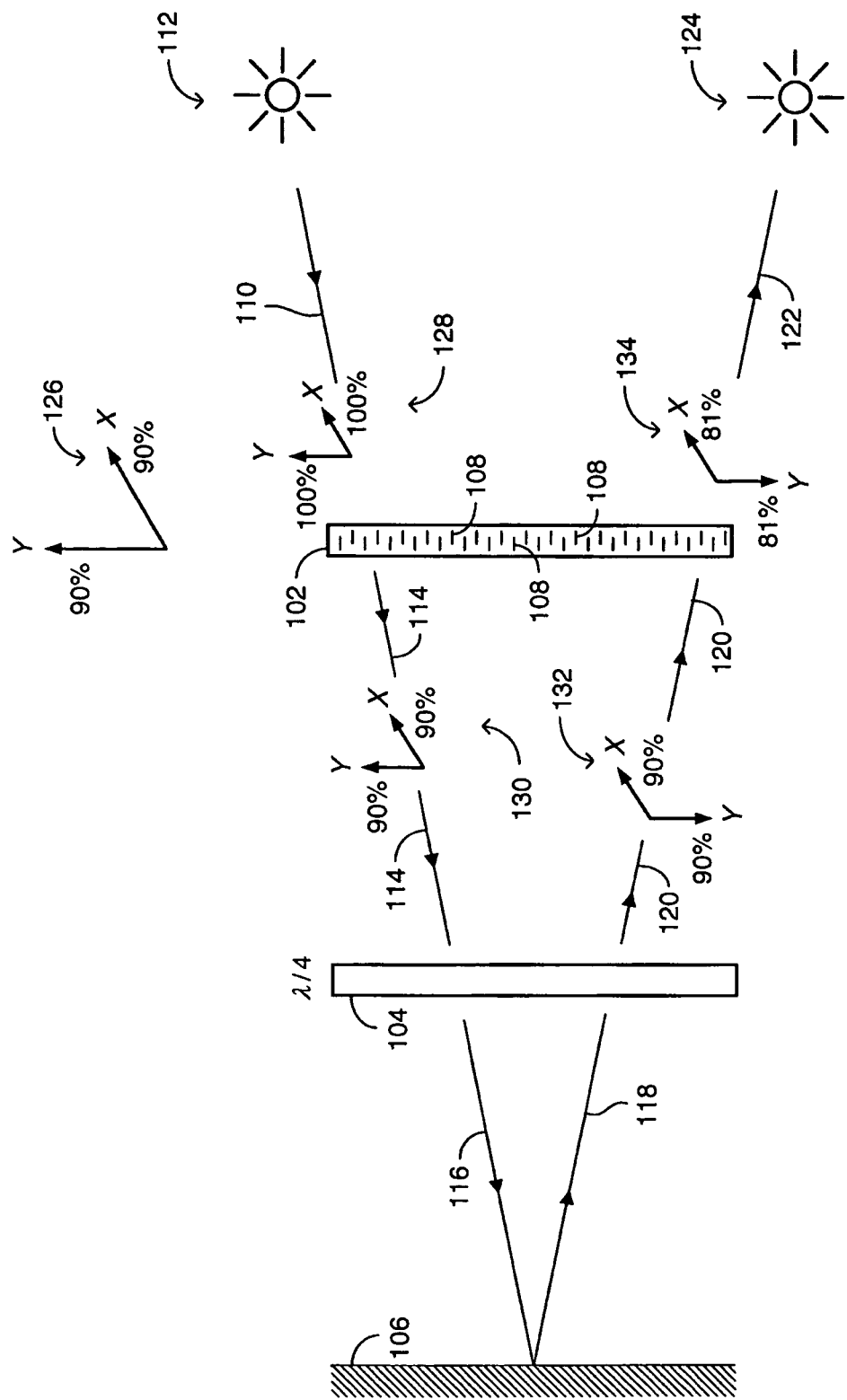
FIG. 1C is a schematic illustration of a side view of the variable reflector of FIG. 1A, in which the relative luminance of a light beam at different stages is shown.
Figure 1D:
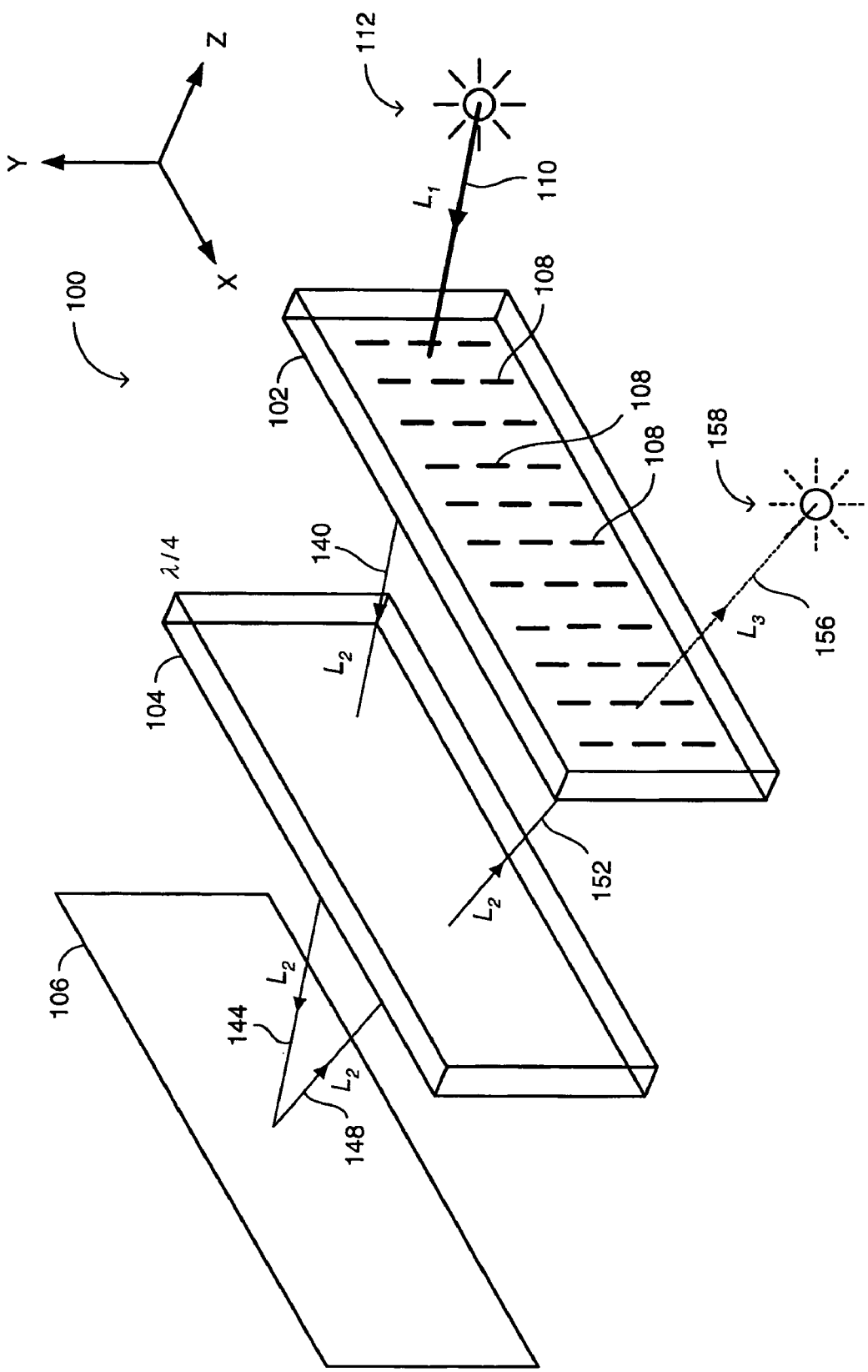
FIG. 1D is a schematic perspective view of the variable reflector of FIG. 1A, in another mode of operation.
Figure 1E:
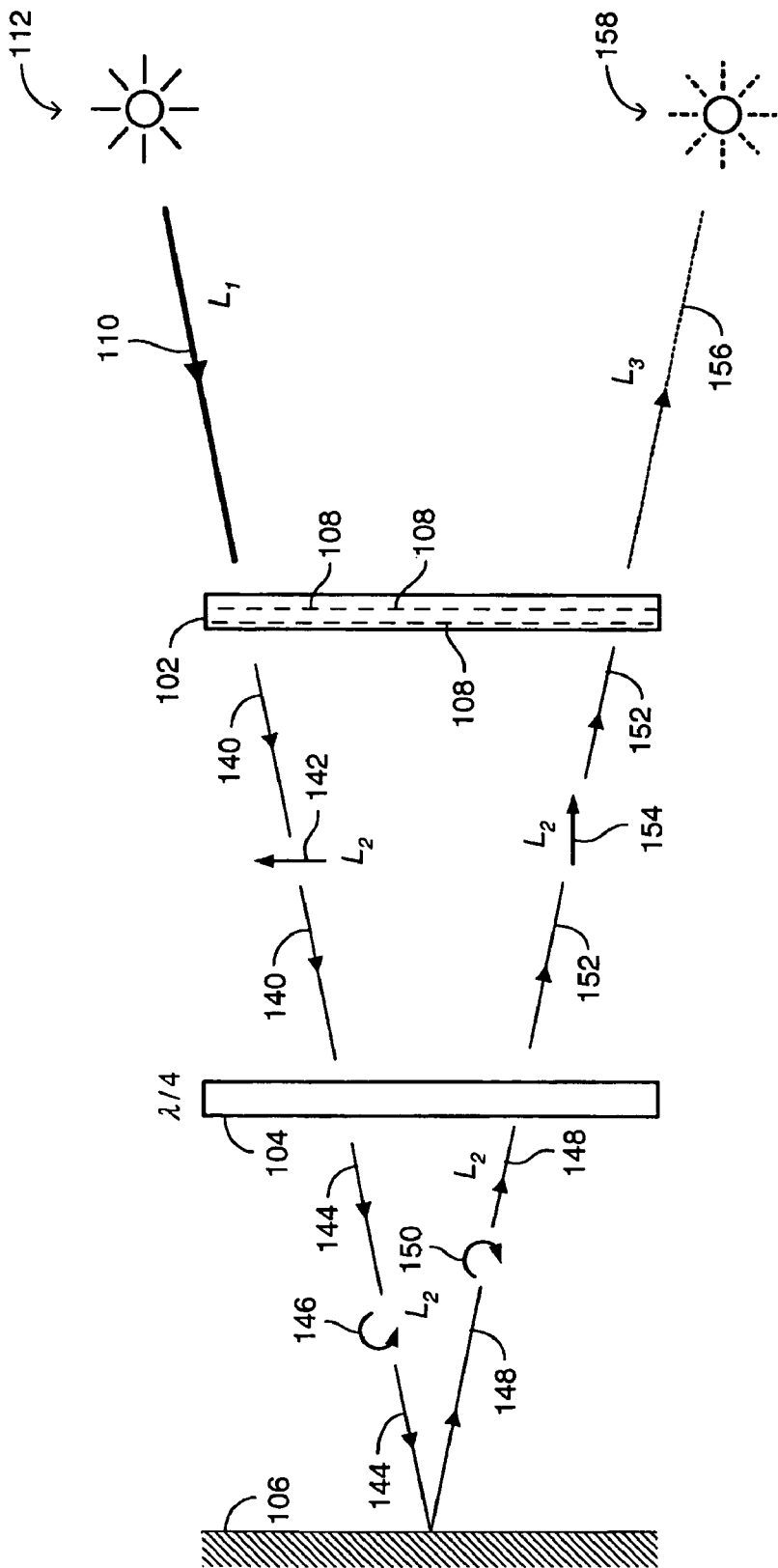
FIG. 1E is a schematic illustration of a side view of the variable reflector of FIG. 1D.
Figure 1F:
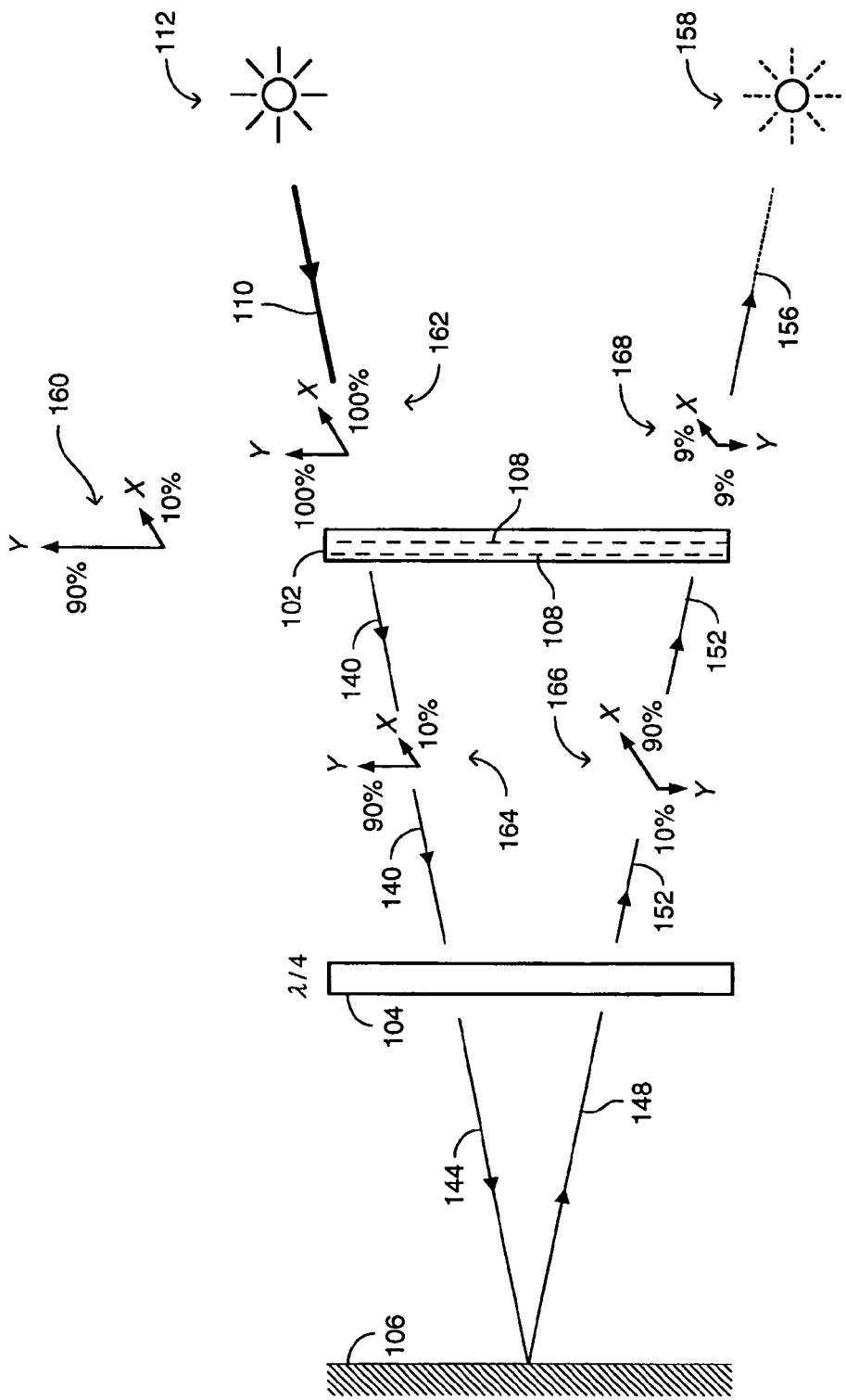
FIG. 1F is a schematic illustration of a side view of the variable reflector of FIG. 1D, in which the relative luminance of a light beam at different stages is shown.

Reference is now made to FIGS. 1A, 1B, 1C, 1D, 1E, and 1F. FIG. 1A is a schematic perspective view of a variable reflector, generally referenced 100, constructed and operative in accordance with an embodiment of the disclosed technique. FIG. 1B is a schematic illustration of a side view of the variable reflector of FIG. 1A. FIG. 1C is a schematic illustration of a side view of the variable reflector of FIG. 1A, in which the relative luminance of a light beam at different stages is shown. FIG. 1D is a schematic perspective view of the variable reflector of FIG. 1A, in another mode of operation. FIG. 1E is a schematic illustration of a side view of the variable reflector of FIG. 1D. FIG. 1F is a schematic illustration of a side view of the variable reflector of FIG. 1D, in which the relative luminance of a light beam at different stages is shown.

Variable reflector 100 includes a variable polarizer 102, an optical phase shifter 104 and a mirror 106. Variable polarizer 102 is a normally-open guest-host liquid crystal (GHLC), known in the art. Advantageously, a small amount of a chiral agent, such as a cholesteric liquid crystal, and the like, is added to variable polarizer 102 in order to impart increased directional order, when an electric voltage is applied there across. The addition of the chiral agent increases the contrast of the reflected or the transmitted image, by diminishing the non-homogenous phase distributions. An optical phase shifter can be a $\lambda/8$ plate, $\lambda/4$ plate, $3\lambda/8$ plate, and the like. However, optical phase shifter 104 is a $\lambda/4$ (quarter-wave) plate.

Optical phase shifter 104 can be made of glass, organic crystal, inorganic crystal, organic polymer, inorganic polymer, liquid crystal, a combination thereof, and the like. Optical phase shifter 104 can be coated by organic polymer, inorganic polymer, and the like.

The optical phase shifter may be in the form of a substantially thin film, having a thickness which provides a desired phase shift to the incoming light. For example, if the thickness of this coating is approximately equal to one-quarter of the wavelength of the incoming light, then this optical phase shifter operates as a $\lambda/4$ plate.

Alternatively, the optical phase shifter may be in the form of a substantially thicker sheet. Accordingly, the thickness of the optical phase shifter can be greater than the wavelength of the incoming light by at least one order of magnitude. In this case, the operation of the optical phase shifter depends on the atomic and molecular structure thereof, which dictates the optical properties.

Optical phase shifter 104 can be either rigid or flexible. When in the form of a substantially thin film (as described herein above), optical phase shifter 104 can be located between two substantially thick layers of an optically transparent material.

A variable polarizer can be either a continuously powered device or an intermittently powered device, as described herein above. In case the variable polarizer is of the continuously powered type, when no electric field is applied across the variable polarizer, the rod-shaped molecules thereof tend to be aligned in a predetermined direction. When an electric field is applied to the variable polarizer, the rod-shaped molecules thereof, tend to be aligned either along the electric field vector or along directions orthogonal to the electric field vector, depending on whether the LC is of positive or negative electrical anisotropy, respectively. With reference to FIG. 1A, variable polarizer 102 is of the continuously powered type. When no electric field is applied to variable polarizer 102, rod-shaped molecules 108 tend to align in a direction, parallel to the Z axis, which is perpendicular to the plane defined by variable polarizer 102. With reference to FIG. 1D, when an electric field is applied to variable polarizer 102 in the Z axis, rod-shaped molecules 108 tend to align in a certain direction (e.g., parallel to the Y axis), which is parallel to the plane defined by variable polarizer 102. The tendency of rod-shaped molecules 108 to align in that certain direction depends on the liquid crystal material, the surface alignment properties and the strength of the electric field applied. When the electric field is decreased to a null value, rod-shaped molecules 108 are aligned back to the original direction. Optical phase shifter 104 is a crystal of a selected thickness, which retards one of the two linearly polarized components of incoming light, by a quarter of wavelength relative to the other linearly polarized component.

Thus, by retarding one of two linearly polarized components of incident linearly polarized light, optical phase shifter 104 converts that linearly polarized light to circularly polarized light. Likewise, optical phase shifter 104 converts incoming circularly polarized light to linearly polarized light. Optical phase shifter 104 is located between variable polarizer 102 and mirror 106.

With reference to FIGS. 1A and 1B, the direction of rod-shaped molecules 108 is parallel to the Z axis (i.e., perpendicular to the plane of variable polarizer 102). It is noted that the term perpendicular is applied to infinitesimal surfaces of variable polarizer 102. For example, if the plane of variable polarizer 102 is curved, then the direction of rod-shaped molecules 108 is normal to the surface of the curved plane. This example is applicable to optical devices whose surfaces are curved, such as lenses, curved mirrors, and the like.

A light beam 110 of a luminance $L_1$ originating from an object 112, reaches variable polarizer 102. Since the direction of rod-shaped molecules 108 is normal to the plane of variable polarizer, variable polarizer 102 transmits a large portion of light beam 110, while having no effect on light beam 110. Thus, a light beam 114 which is unaffected and of luminance $L_1$, exits variable polarizer 102 and enters optical phase shifter 104. Optical phase shifter 104 delays one of the two linearly polarized components of light beam 114 relative to the other linearly polarized component of light beam 114, by π/2 radians and directs light beam 116 toward mirror 106.

Since optical phase shifter 104 is transparent, the luminance of light beam 116 is equal to $L_1$. Mirror 106 reflects light beam 116 as a light beam 118 toward optical phase shifter 104. Optical phase shifter 104 delays one of the two linearly polarized components of light beam 118 relative to the other linearly polarized component of light beam 118, by π/2 radians and directs light beam 120 toward variable polarizer 102. Likewise, the luminance of light beam 120 is equal to $L_1$.

Variable polarizer 102 receives light beam 120 and emits a light beam 122. Since the direction of rod-shaped molecules 108 is normal to the plane of variable polarizer 102, variable polarizer 102 transmits a large portion of light beam 120 while having no effect on light beam 120. Thus, the luminance of light beam 122 is theoretically equal to $L_1$. An observer (not shown) can view an image 124 of object 112 at almost the same luminance $L_1$ as of object 112.

With further reference to FIG. 1C, a set of arrows 126 represents the transmittance of variable polarizer 102 along the X and Y axes (i.e., the transmittance of the components linearly polarized in the X and Y directions, respectively). The following is a semi-realistic example in which variable polarizer 102 transmits 90% of the incoming light along each of the X and Y axes, when rod-shaped molecules 108 are aligned along the X axis. The luminance of light beam 110 along each of the X and Y axes is defined 100% (as indicated by a set of arrows 128). Since variable polarizer 102 transmits 90% of the incoming light, the luminance of light beam 114 emerging from variable polarizer 102 along each of the X and Y axes, is reduced to 90% of that of light beam 110 (represented by a set of arrows 130).

The components of light beam 120 linearly polarized in the X and Y directions (represented by a set of arrows 132) are rotated by π/2 radians relative to those of light beam 114, after light beam 114 passes through optical phase shifter 104, is reflected by mirror 106 and passes through optical phase shifter 104 once again. Since optical phase shifter 104 and mirror 106 do not have any substantial effect on the luminance of light beam 114, the luminance of light beam 120 along the X and Y axes is still 90% of that of light beam 110.

As indicated by the set of arrows 126, in practice, variable polarizer 102 transmits 90% of light beam 120. Thus, the luminance of light beam 122 along the X and Y axes, as represented by a set of arrows 134, is reduced to 81% of that of light beam 110 (i.e., 90% of 90%).

With reference to FIGS. 1D and 1E, the direction of rod-shaped molecules 108 is parallel to the Y axis (i.e., parallel to the plane of variable polarizer 102). Thus, in this mode, variable polarizer 102 operates as a linear polarizer, which linearly polarizes the incident light along the Y axis. Variable polarizer 102 linearly polarizes light beam 110 and emits a polarized light beam 140. Light beam 140 includes a component of light beam 110, which is polarized along the Y axis, and is represented by an arrow 142. Hence, the luminance thereof is $L_2$ which is a fraction of luminance $L_1$ of object 112.

It is noted that in practice, rod-shaped molecules 108 may behave similar to the rod-shaped molecules of a twisted-nematic liquid crystal, wherein the rod-shaped molecules are twisted by ninety degrees from one plane of the liquid crystal to the other. In this case, the light which exits the exit plane of the variable polarizer is polarized at ninety degrees relative to the direction of the rod-shaped molecules at the entrance plane of the variable polarizer.

Optical phase shifter 104 receives light beam 140 and emits a light beam 144. Light beam 144 is circularly polarized and is represented by a curved arrow 146. Since optical phase shifter 104 is transparent, the luminance of light beam 144 is equal to $L_2$. Mirror 106 reflects light beam 144 as a light beam 148 toward optical phase shifter 104. Light beam 148 is circularly polarized, represented by a curved arrow 150 and the luminance thereof is equal to $L_2$. Optical phase shifter 104 emits a light beam 152 which is linearly polarized and represented by an arrow 154 (i.e., parallel to the X axis). Since optical phase shifter 104 is transparent, the luminance of light beam 152 is equal to $L_2$.

It is noted that arrow 154 (representing the linear polarization of light beam 152), is orientated at 90 degrees relative to arrow 142 (representing the linear polarization of light beam 140). Thus, optical phase shifter 104 and mirror 106 together operate as a device which rotates the linear polarization of light beam 140 by π/2 radians.

Variable polarizer 102 receives light beam 152 from optical phase shifter 104, linearly polarizes light beam 152 and emits a light beam 156. Light beam 152 is polarized along the X axis and perpendicular to the direction of rod-shaped molecules 108 which lies along the Y axis. Light beam 156 includes only a component of light beam 152, which is linearly polarized along the Y axis. In an idealized example, variable polarizer 102 is an ideal polarizer, which completely blocks any component of incident light whose linear polarization is orthogonal to the orientation thereof. In such an idealized example, the luminance $L_3$ thereof shall be equal to zero.

Alternatively, in an example wherein variable polarizer 102 is not an ideal polarizer, it does not entirely block a component of light beam 110 which is linearly polarized along the X axis. Accordingly, light beam 140 further includes a small portion of a component of light beam 110 which is linearly polarized along the X axis. Light beam 152 includes this component, rotated to be polarized parallel to the Y axis. In this case, the luminance $L_3$ thereof shall be small but greater than zero, and thus, the observer shall view an image 158 of object 112, whose luminance $L_3$ is a fraction of luminance $L_1$ of object 112.

With further reference to FIG. 1F, which is complementary to the example set forth in FIG. 1C, a set of arrows 160 represents the transmittance of variable polarizer 102 along the X and Y axes. For example, when rod-shaped molecules 108 are aligned along the Y axis, variable polarizer 102 transmits 90% of the incoming light along the Y axis and 10% thereof along the X axis. The incident luminance of light beam 110 along each of the X and Y axes is defined 100% (as indicated by a set of arrows 162). Thus, the luminance of light beam 140, as represented by a set of arrows 164, is reduced to 90% of that of light beam 110 along the Y axis and to 10% of that of light beam 110 along the X axis.

The X and Y components of light beam 152 (represented by a set of arrows 166) are rotated by π/2 radians relative to those of light beam 140, after light beam 140 passes through optical phase shifter 104, is reflected by mirror 106 and passes through optical phase shifter 104 once again. Since optical phase shifter 104 and mirror 106 do not have any substantial effect on the luminance of light beam 140, the luminance of light beam 152 along the rotated X axis is still 90% of that of light beam 110 and along the Y axis it is 10% of that of light beam 110.

As indicated by the set of arrows 160, variable polarizer 102 transmits 90% of light beam 152 along the Y axis and 10% thereof along the X axis. Thus, the luminance of light beam 156, as represented by a set of arrows 168, along the Y axis is reduced to 9% of that of light beam 110 (i.e., 90% of 10%). Likewise, the luminance of light beam 156 along the X axis is reduced to 9% of that of light beam 110 (i.e., 10% of 90%).

It is noted that variable reflector 100 can be used with various types of optical devices, such as general purpose mirror, ground vehicle mirror, aircraft mirror, marine vehicle mirror, spacecraft mirror (e.g., rear-view mirror or side-view mirror), spectacles, binoculars, periscope, reflex camera, telescope, microscope, camera viewer (for locating an object before taking the picture of the object), view finder (for viewing an object while making a video recording of the object), and the like.

Variable polarizer 102 of variable reflector 100 is normally open (i.e., rod-shaped molecules 108 are aligned normal to the plane of variable polarizer 102, when no electric field is applied across variable polarizer 102). However, it is noted that a normally closed type variable polarizer can be employed instead of the normally open type. In this case, the rod-shaped molecules of the variable polarizer are aligned parallel to the plane of the variable polarizer, when no electric field is applied across the variable polarizer.

Alternatively, variable polarizer 102 is of the intermittently powered type, whereby the level of polarization thereof can be changed by applying a momentary electric field in a predetermined pulse shape. Thus, in case of power failure, an electric field in a predetermined pulse shape can be applied momentarily to variable polarizer 102, thereby transforming variable reflector 100 to a state of maximum reflectivity. The electric pulse can be drawn from an electric storage unit (not shown), such as a capacitor, an inductor (coil), a battery, a generator, and the like.

According to another aspect of the disclosed technique, a controller adjusts the level of polarization of the variable polarizer according to variations in the luminance of the incoming light. For this purpose, a light sensor provides information to the controller, respective of the luminance of the incoming light at any given time. The light sensor together with the controller and the variable polarizer form an open loop control system.

Figure 2:
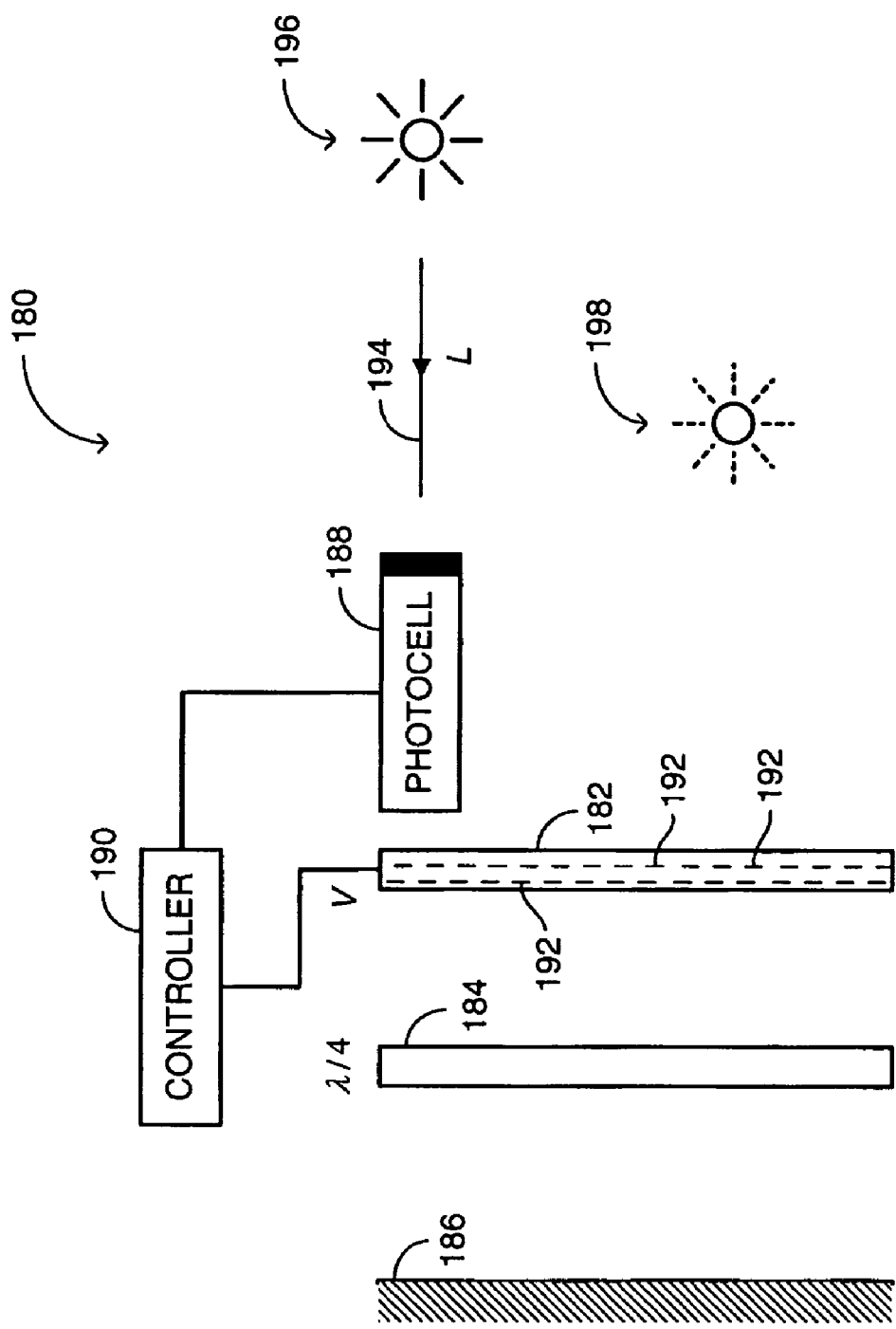
FIG. 2 is a schematic illustration of a variable reflector, constructed and operative in accordance with another embodiment of the disclosed technique.

Reference is now made to FIG. 2, which is a schematic illustration of a variable reflector, generally referenced 180, constructed and operative in accordance with another embodiment of the disclosed technique. Variable reflector 180 includes a variable polarizer 182, an optical phase shifter 184, a mirror 186, a photocell 188 and a controller 190. Variable polarizer 182 and optical phase shifter 184 are similar to variable polarizer 102 and optical phase shifter 104, respectively, as described herein above in connection with FIG. 1A. An optical phase shifter can be a λ/8 plate, λ/4 plate, 3λ/8 plate, and the like. However, optical phase shifter 184 is a λ/4 (quarter-wave) plate. Optical phase shifter 184 is located between variable polarizer 182 and mirror 186. Controller 190 is coupled with photocell 188 and with variable polarizer 182.

Controller 190 controls the electric field across of the variable polarizer 182, by applying a voltage V across variable polarizer 182. Rod-shaped molecules 192 are aligned along a predetermined direction, according to the magnitude of this electric field. As described herein above in connection with FIGS. 1D and 1E, the reflectance of variable reflector 180 depends on the collective directions of rod-shaped molecules 192. Photocell 188 detects a luminance L of a light beam 194 reflected by an object 196 and provides a signal respective of luminance L to controller 190. Controller 190 determines the value of voltage V according to the value of luminance L, and provides it to variable polarizer 182, whereby an electric field E is applied across variable polarizer 182. Thus, controller 190 dynamically sets the reflectance of variable reflector 180 according to value luminance L.

For example, if an observer (not shown) desires to view a reflected image 198 of object 196 at 400 fL and the luminance of light beam 194 is 1000 fL, then controller 190 applies a voltage V across variable polarizer 182 such that variable polarizer 182 transmits only 63% of light in each direction (i.e., $$\left(\text{i.e., } \sqrt{\frac{400}{1000}} \approx 0.63\right).$$

If the luminance of light beam 194 decreases to 800 fL, then controller 190 changes the value of the applied voltage V, such that variable polarizer 182 transmits 70% of light in each direction (i.e., $$\left(\text{i.e., } \sqrt{\frac{400}{800}} \approx 0.70\right).$$

Photocell 188 can be of various types. For example, photocell 188 can utilize various types of light metering schemes, such as spot metering, center-weighted metering, multi-zone metering, ambient light metering, and the like.

According to another aspect of the disclosed technique, a light sensor detects the luminance of the light which emerges from the variable polarizer and provides information respective of the detected luminance to the controller. The controller together with the light sensor and the variable polarizer form a closed loop control system, wherein the controller adjusts the reflectance of the variable reflector by comparing the detected luminance with a reference value.

Figure 3:
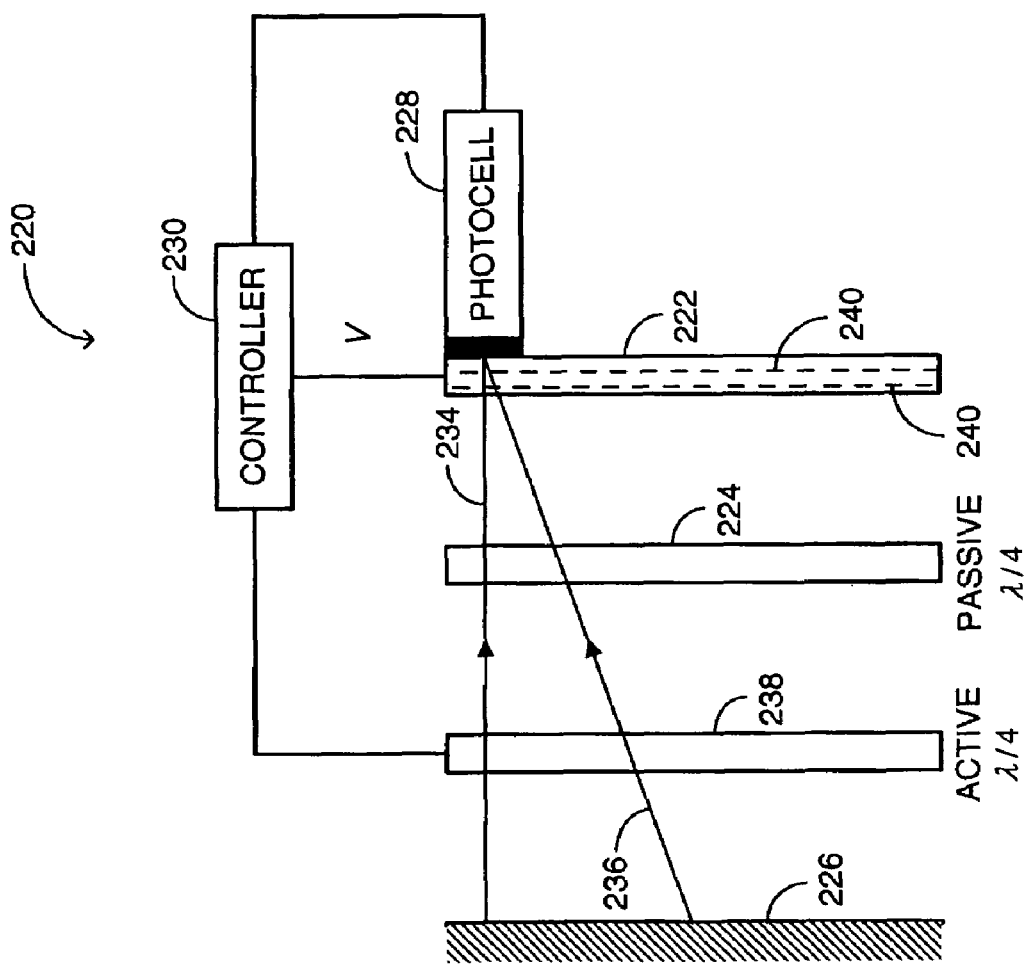
FIG. 3 is a schematic illustration of a variable reflector, constructed and operative in accordance with a further embodiment of the disclosed technique.

Reference is now made to FIG. 3, which is a schematic illustration of a variable reflector, generally referenced 220, constructed and operative in accordance with a further embodiment of the disclosed technique. Variable reflector 220 includes a variable polarizer 222, a passive optical phase shifter 224, a bi-stable optical phase shifter 238, a mirror 226, a photocell 228 and a controller 230. An optical phase shifter can generally be a λ/8 plate, λ/4 plate, 3λ/8 plate, and the like. In the present example, passive optical phase shifter 224 is a λ/4 (quarter-wave) plate. Bi-stable optical phase shifter 238 can operate either as a transparent optical element or as a quarter-wave plate. An electric field pulse, can cause bi-stable optical phase shifter 238 to switch between the two states. Variable polarizer 222 is constructed such that when no electric field is applied thereto, the structure thereof is planar and when an electric field is applied thereto, the structure thereof switches to a homeotropic one (i.e., variable polarizer 222 is of the normally closed type).

Passive optical phase shifter 224 is located between variable polarizer 222 and bi-stable optical phase shifter 238. Bi-stable optical phase shifter 238 is located between passive optical phase shifter 224 and mirror 226. Photocell 228 is coupled with variable polarizer 222 and detects the luminance of light beams 234 and 236 which exit variable polarizer 222.

Controller 230 is coupled with variable polarizer 222, bi-stable optical phase shifter 238 and with photocell 228, thereby forming together a closed loop control system. When substantial electric power is available, controller 230 sets bi-stable optical phase shifter 238 in a twisted state. In this case, variable polarizer 222, passive optical phase shifter 224, bi-stable optical phase shifter 238 and mirror 226, operate in a similar way to variable polarizer 102, optical phase shifter 104 and mirror 106 (FIG. 1D). Light beams (not shown) which enter passive optical phase shifter 224 from variable polarizer 222 and pass through passive optical phase shifter 224, pass through bi-stable optical phase shifter 238 unaffected and strike mirror 226. A set of reflected light beams (not shown) which are reflected from mirror 226, likewise pass back through bi-stable optical phase shifter 238 unaffected and exit variable polarizer 222 after passing through passive optical phase shifter 224, thereby providing a reflected image (not shown) of an object (not shown), at a reduced luminance. Controller 230 adjusts the electric field across variable polarizer 222, by comparing the value of the luminance detected by photocell 228, with a reference value.

In case of power failure, variable polarizer 222 switches to a planar state and controller 230 applies an electric field of a predetermined pulse shape to bi-stable optical phase shifter 238, setting optical phase shifter 238 to an untwisted state, whereby bi-stable optical phase shifter 238 operates as a quarter-wave plate. Only the component of incident light, which is polarized in the direction of rod-shaped molecules 240 of variable polarizer 222, passes through variable polarizer 222 and strikes passive optical phase shifter 224. It is noted that unpolarized light (e.g., sunlight) undergoes a reduction of approximately 50% in intensity when passing through variable polarizer 222. Thus, light beams (not shown) polarized in the direction of rod-shaped molecules 240, strike passive optical phase shifter 224. These light beams pass through passive optical phase shifter 224 and bi-stable optical phase shifter 238, and are reflected from mirror 226 back through bi-stable optical phase shifter 238 and passive optical phase shifter 224. Since passive optical phase shifter 224 and bi-stable optical phase shifter 238 together operate as a half-wave plate, these light beams do not undergo changes in their state of polarization. Hence, these light beams, being polarized in the direction of rod-shaped molecules 240, pass back through variable polarizer 222 with little reduction in intensity.

Thus, in case of power failure, variable reflector 220 provides a reflected image of the object, while reducing the image luminance by approximately 50%.

It is noted that instead of a bi-stable optical phase shifter, a passive optical phase shifter can be employed. It is further noted that a plurality of either bi-stable optical phase shifters or passive optical phase shifters can be employed. For example, four passive optical phase shifters, each in the form of λ/8 plate can be located between the variable polarizer and the mirror.

According to another aspect of the disclosed technique, an active-region light sensor detects the luminance of an object of interest and a passive-region light sensor detects the luminance of the ambient light. A controller adjusts the polarization level of a variable polarizer according to the luminance levels detected by the active-region light sensor and the passive-region light sensor, such that the contrast of an image of the object displayed by the variable polarizer, is at a selected level.

Figure 4:
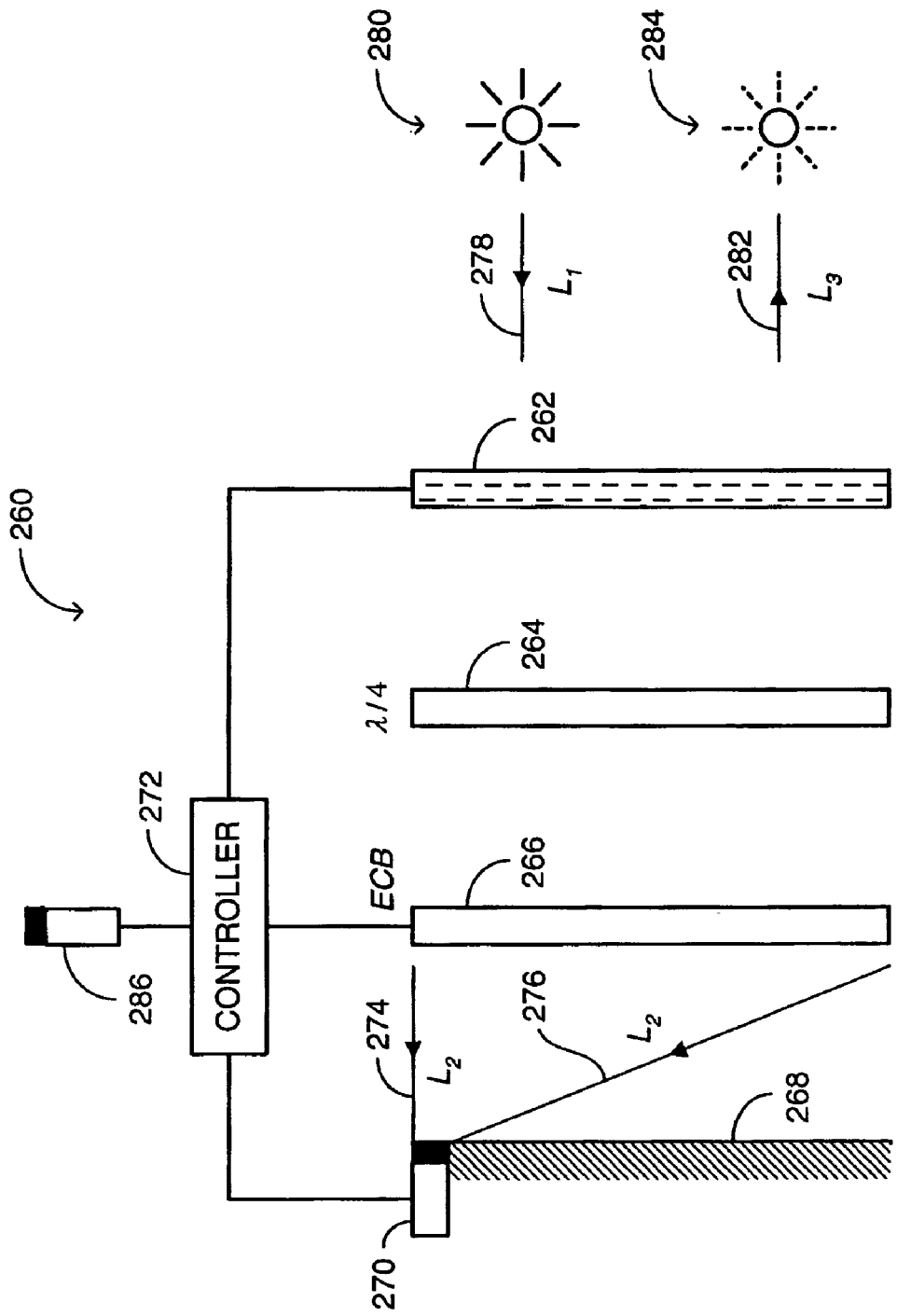
FIG. 4 is a schematic illustration of a variable reflector, constructed and operative in accordance with another embodiment of the disclosed technique.

Reference is now made to FIG. 4, which is a schematic illustration of a variable reflector, generally referenced 260, constructed and operative in accordance with another embodiment of the disclosed technique. Variable reflector 260 includes a variable polarizer 262, an optical phase shifter 264, a switchable optical phase shifter 266, a mirror 268, at least one active-region light sensor 270, at least one passive-region light sensor 286 and a controller 272. Variable polarizer 262 is of the normally closed type. In the present example, optical phase shifter 264 is a λ/4 (quarter-wave) plate.

Switchable optical phase shifter 266 is an optical element which operates as an optical phase shifter when no electric voltage is applied thereto, and does not change the phase of the incoming light, when an electric voltage is applied thereto. Switchable optical phase shifter 266, can be an Electrically Controllable Birefringent (ECB) crystal, and the like. Active-region light sensor 270 is located and oriented so as to detect the luminance of light arriving from an active region of interest (e.g., in case of a rear view mirror of a vehicle, the backward field of view of the operator, which is visible using the mirror). Passive-region light sensor 286 is located and oriented so as to detect the luminance of light coming from a passive region of interest (e.g., in case of a vehicle, the ambient light external to the backward field of view).

Each of active-region light sensor 270 and passive-region light sensor 286 is similar to photocell 188 (FIG. 2), as described herein above. It is noted that instead of active-region light sensor 270 and passive-region light sensor 286 a plurality of active-region light detectors and passive-region light detectors can be employed. For example, the plurality of light detectors may be arranged in a light detecting array.

Switchable optical phase shifter 266 is a crystal which operates as a quarter-wave plate, when no electric voltage is applied thereto, and operates as a passive transparent medium, when an electric voltage is applied thereto. Optical phase shifter 264 is located between variable polarizer 262 and switchable optical phase shifter 266. Switchable optical phase shifter 266 is located between optical phase shifter 264 and mirror 268. Active-region light sensor 270 is optically coupled with mirror 268 and detects a luminance $L_2$ of light beams 274 and 276 which emerge from variable polarizer 262. The portion of mirror 268, which covers active-region light sensor 270, may be semi-transparent.

Controller 272 is coupled with variable polarizer 262, switchable optical phase shifter 266, active-region light sensor 270 and passive-region light sensor 286, thereby forming together a closed loop control system. $L_1$ designates the luminance of a uniform unpolarized light beam 278 as reflected from an object 280 or emitted thereby. $L_3$ designates the desired average luminance of a light beam 282 producing an image 284 of object 280. Controller 272 adjusts the electric field across variable polarizer 262, by comparing the value of luminance $L_2$ as detected by active-region light sensor 270, with a reference luminance value.

When substantial electric power is available, switchable optical phase shifter 266 operates as a passive transparent medium and thus, variable reflector 260 operates similar to variable reflector 100 as illustrated in FIG. 1A (except that variable polarizer 262 in this case is a normally closed variable polarizer). When substantial electric power is unavailable, switchable optical phase shifter 266 operates as a quarter-wave plate and variable polarizer 262 switches to the closed state.

When no substantial power is present, variable polarizer 262 linearly polarizes a light beam passing there through in a certain direction. Switchable optical phase shifter 266 and optical phase shifter 264 together form a λ/2 wave plate, thereby rotating the polarized light beam by half a circle. Reflector 268 reflects the light beam, thereby rotating it by an additional half circle. Finally, switchable optical phase shifter 266 together with optical phase shifter 264 rotate the light beam by an additional half circle, where it arrives at the variable polarizer 262, polarized in that same certain direction and left unaffected thereby. Accordingly, variable reflector 260 reflects approximately 50% of an incoming unpolarized light beam.

In general, it is desirable to vary the contrast of an image of an object as displayed by a variable reflector, against the background of the variable reflector. For example, when a driver is operating an automobile during daylight, the contrast of the view of the car driving behind, as viewed by the driver in the rear view mirror, should be substantially high for the driver to be able to distinguish the image of the car behind, against the background. On the contrary, during the darker hours of the day, the contrast of the view of the car driving behind which is distinguished by the headlights thereof, should be substantially low, so that the eyes of the driver are not disturbed by the high intensity of the headlights against the dark background.

During normal operation, when electric power is available, controller 272 sets the polarization level of variable polarizer 262, according to signals received from active-region light sensor 270 and passive-region light sensor 286 and contrast data, such that variable reflector 260 displays image 284 at a selected contrast value. The contrast data can be in the form of a look-up table, an algorithm, and the like, stored within controller 272. Alternatively, the contrast data can be a single contrast value which is set by the driver (not shown). The driver can set the single contrast value by varying the setting of a potentiometer, a voltage source, a power storage device, and the like.

Figure 5:
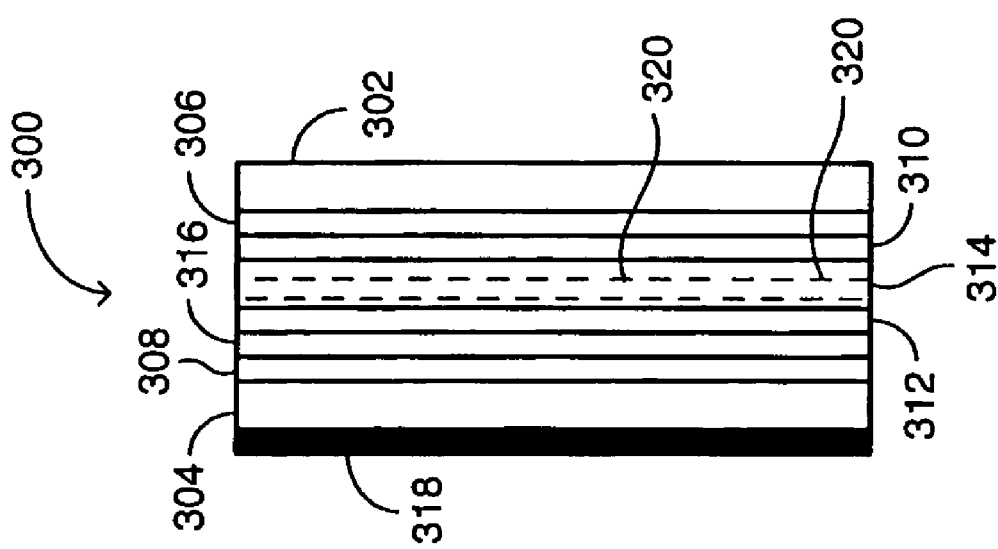
FIG. 5 is a schematic illustration of a section of a variable reflector, constructed and operative in accordance with a further embodiment of the disclosed technique.

Reference is now made to FIG. 5, which is a schematic illustration of a section of a variable reflector, generally referenced 300, constructed and operative in accordance with a further embodiment of the disclosed technique. Variable reflector 300 includes protective layers 302 and 304, electrically conducting layers 306 and 308, electrically insulating layers 310 and 312, a variable level polarizing layer 314, an optical phase shifting layer 316 and a reflector 318.

Each of protective layers 302 and 304 is made of a transparent material which transmits a large portion of light without distorting the image, such as glass, crystal, polymer, plastic, and the like. Each of electrically conducting layers 306 and 308 is made of a thin, transparent and electrically conductive material, such as a conductive polymer, glass coated by indium-tin-oxide, tin-oxide, a metal (e.g., gold and silver), and the like. Each of electrically insulating layers 310 and 312 is made of a thin, transparent and electrically insulating material, such as a polymer, inorganic silicon dioxide, silicon oxide, silicon nitride, and the like.

Variable level polarizing layer 314 is a thin layer of a material similar to that of variable polarizer 102 (FIG. 1A). Optical phase shifting layer 316 is a thin layer of a material similar to that of optical phase shifter 104 (FIG. 1A). Reflector 318 is made of a material such as glass, polymer, plastic, beryllium, and the like, whose surface is coated with a reflective material, such as chrome, mercury, aluminum, silver, and the like.

Protective layers 302 and 304, electrically conducting layers 306 and 308, electrically insulating layers 310 and 312, variable level polarizing layer 314 and optical phase shifting layer 316 are located at the reflective side of reflector 318. Electrically conducting layers 306 and 308, electrically insulating layers 310 and 312, variable level polarizing layer 314 and optical phase shifting layer 316 are located between protective layers 302 and 304. Electrically insulating layers 310 and 312, variable level polarizing layer 314 and optical phase shifting layer 316 are located between electrically conducting layers 306 and 308. Electrically insulating layers 310 and 312 and variable level polarizing layer 314 are located between electrically conducting layer 306 and optical phase shifting layer 316. Variable level polarizing layer 314 is located between electrically insulating layers 310 and 312.

Electrically conducting layers 306 and 308 are coupled with a power source (not shown) and the output of the power source is controlled by a controller (not shown), similar to controllers 190, 230 and 270 as described herein above in connection with FIGS. 2, 3 and 4, respectively. Electrically conducting layers 306 and 308 produce an electric field across variable level polarizing layer 314, thereby changing the direction of rod-shaped molecules 320 form one position to the other, and varying the transmittance of variable level polarizing layer 314. The employment of two electrically conducting layers, such as electrically conducting layers 306 and 308, in a variable reflector or a variable transmitter, wherein the electrically conducting layers are located parallel to one another, is referred to herein below as "parallel-plane configuration". Electrically insulating layers 310 and 312 electrically insulate between electrically conducting layers 306 and 308.

It is noted that if variable reflector 300 is operated without electrically insulating layers 310 and 312, the electric voltage applied across electrically conducting layers 306 and 308, brings about oxidation and reduction reactions in rod-shaped molecules 320, thereby causing the properties of rod-shaped molecules 320 to deteriorate after a few cycles of operation. The dielectric constant of each of electrically insulating layers 310 and 312 is of such a value, that diffusion of electric charges to rod-shaped molecules 320 is reduced, thereby preventing damage to rod-shaped molecules 320. However, this dielectric constant is of such value that the electromagnetic field generated by electrically conducting layers 306 and 308, readily penetrate through electrically insulating layers 310 and 312 and reach rod-shaped molecules 320. Variable reflector 300 can be used with a lens or a lens system, such as converging lens, diverging lens, Fresnel lens, holographic lens, deffractive, a combination thereof, and the like. In this case, for example a combination of a flat reflector, similar to reflector 318, and a converging lens (not shown), can be incorporated in the variable reflector, instead of employing a concave reflector. Thus, variable reflector 300 can direct an image (not shown) of an object (not shown) to a predetermined location in space. Furthermore, by incorporating a lens with a substantially flat variable reflector, the particular optical properties of the lens can be imparted to the flat variable reflector.

Variable reflector 300 can have either a positive radius of curvature (i.e., being convex), a negative radius of curvature (i.e., being concave), or a combination of positive and negative radii of curvatures (i.e., an arbitrary curved plane, as well as being substantially flat. Variable reflector 300 can be used in a liquid environment as well as in a gaseous one. Variable reflector 300 can be flexible as well as being rigid. Each of electrically insulating layers 310 and 312 can also operate as an alignment layer. Alternatively, alignment layers are individually located adjacent to the variable polarizer and coupled with the respective electrically insulating layer.

Figure 6:
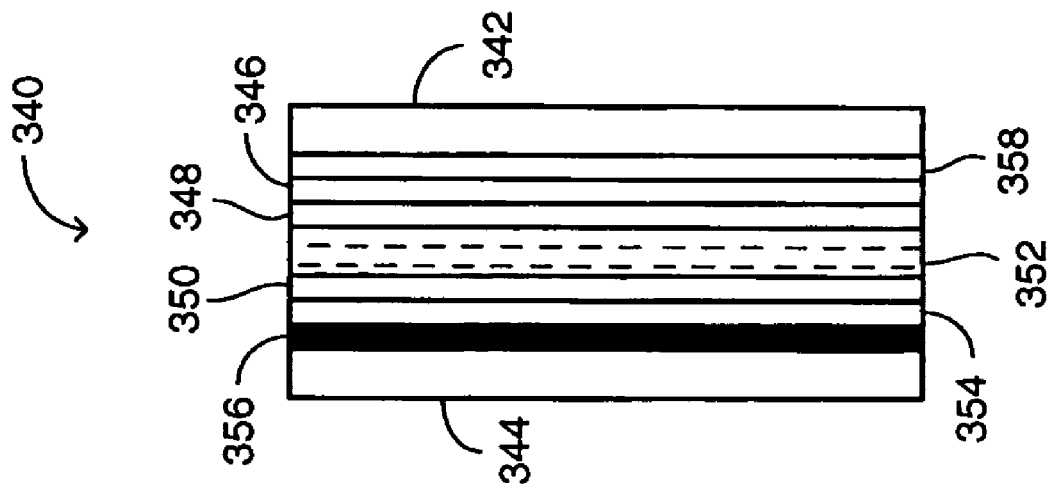
FIG. 6 is a schematic illustration of a section of a variable reflector, constructed and operative in accordance with another embodiment of the disclosed technique.

Reference is now made to FIG. 6, which is a schematic illustration of a section of a variable reflector, generally referenced 340, constructed and operative in accordance with another embodiment of the disclosed technique. Variable reflector 340 includes protective layers 342 and 344, an electrically conducting layer 346, electrically insulating layers 348 and 350, a variable level polarizing layer 352, an optical phase shifting layer 354 an electrically conducting reflector 356 and a temperature control layer 358.

Protective layers 342 and 344 are similar to protective layers 302 and 304, as described herein above in connection with FIG. 5. Electrically conducting layer 346 is similar to electrically conducting layers 306 and 308, as described herein above in connection with FIG. 5. Electrically insulating layers 348 and 350 are similar to electrically insulating layers 310 and 312, as described herein above in connection with FIG. 5. Variable level polarizing layer 352 is similar to variable level polarizing layer 314, as described herein above in connection with FIG. 5. Optical phase shifting layer 354 is similar to optical phase shifting layer 316, as described herein above in connection with FIG. 5. Electrically conducting reflector 356 is made of a reflective material which conducts electrical current. Temperature control layer 358 is a transparent layer, which can provide either a cooling or a heating effect. For example, temperature control layer 358 can be a layer in which a cooling or heating fluid (e.g., air, water, Freon) flows, a Josephson junction providing cooling, a high electrical resistance element providing heating, and the like. Electrically conducting layer 346, electrically insulating layers 348 and 350, variable level polarizing layer 352, optical phase shifting layer 354, electrically conducting reflector 356 and temperature control layer 358 are located between protective layers 342 and 344. Electrically conducting layer 346, electrically insulating layers 348 and 350, variable level polarizing layer 352 and optical phase shifting layer 354 are located between temperature control layer 358 and electrically conducting reflector 356. Electrically insulating layers 348 and 350 and variable level polarizing layer 352 are located between electrically conducting layer 346 and optical phase shifting layer 354. Variable level polarizing layer 352 is located between electrically insulating layers 348 and 350.

Electrically conducting layer 346, electrically conducting reflector 356 are coupled with a power source (not shown). Temperature control layer 358 can also be coupled to the power source, to a heating or cooling source, and the like. Thus, electrically conducting layer 346 and electrically conducting reflector 356 produce an electric field across variable level polarizing layer 352. In addition, electrically conducting reflector 356 reflects light which enters protective layer 342, out through protective layer 342. It is noted that since electrically conducting reflector 356 operates both as an electrically conducting layer (such as electrically conducting layers 306 and 308 of FIG. 5) and as a reflector (such as reflector 318), the total thickness of variable reflector 340 is less than that of variable reflector 300.

Temperature control layer 358 either heats or cools variable level polarizing layer 352, thereby allowing operation of variable level polarizing layer 352 in low or high temperature environments. Operation of temperature control layer 358 can be controlled either automatically, according to the temperature setting of a temperature sensor coupled thereto, or manually.

Figure 7:
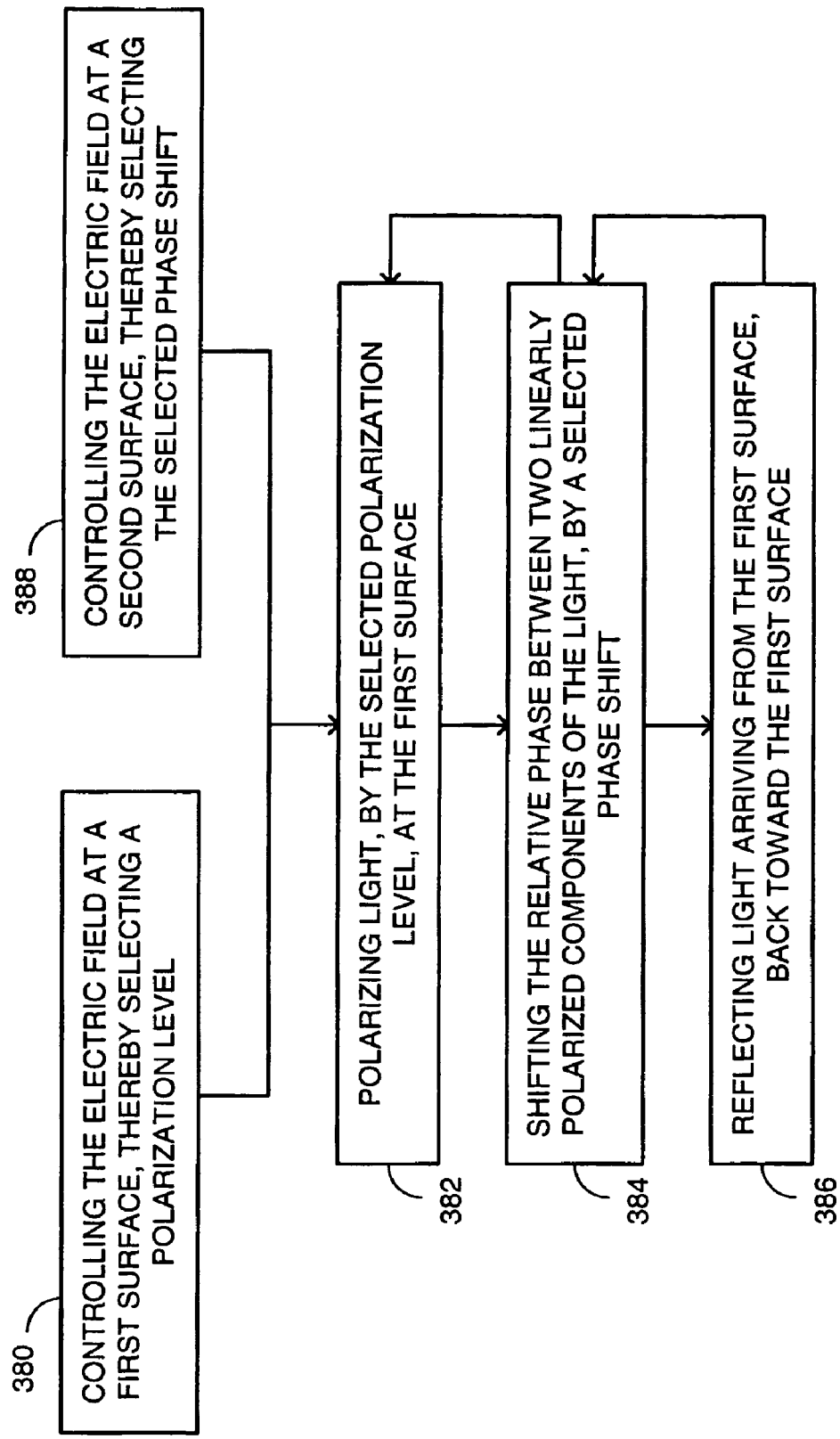
FIG. 7 is a schematic illustration of a method for operating the variable reflector of FIG. 1A, operative in accordance with a further embodiment of the disclosed technique.

Reference is now made to FIG. 7, which is a schematic illustration of a method for reflecting light at a variable reflectance, operative in accordance with a further embodiment of the disclosed technique. In procedure 380, the electric field at a first surface is controlled, thereby selecting a polarization level. It is noted that the electric field is controlled to set the variable polarizer at a selected dichroism level, thereby setting the variable polarizer at a polarization level corresponding to the selected dichroism level.

For example, the electric field can be turned on to a selected value and be kept at that value, or completely turned off. Alternatively, the value of the electric field can be changed in sequence, thereby forming a pulse of a selected shape. It is noted that one of the polarization levels may be zero (i.e., corresponding to a non-polarizing state of the surface). With reference to FIGS. 1A and 1D, variable polarizer 102 is set to either a homeotropic state (i.e., a zero polarization level), as shown in FIG. 1A, or a planar state (i.e., a non-zero polarization level), as shown in FIG. 1D.

In procedure 382, light is polarized by the selected level of polarization, at the first surface. In case the selected polarization level is zero, the first surface may transmit the light there through without polarizing that light. In the example set forth in FIG. 1A, variable polarizer 102 applies no polarization to light beam 110. In the example set forth in FIG. 1D, variable polarizer 102 polarizes light beam 110 in the direction of the Y axis.

In procedure 384, the relative phase between two linearly polarized components of the light, is shifted by a selected phase shift. It is noted that the selected phase shift may be either zero or non-zero. If the selected phase shift is zero, the light may be transmitted, or a phase shift equivalent to zero (e.g., a multiple of $2\pi$ radians) may be applied to the linearly polarized components of the light. In the example set forth in FIG. 1A, optical phase shifter 104 delays one of the two linearly polarized components of light beam 114 relative to the other linearly polarized component of light beam 114, by $\pi/2$ radians. In the example set forth in FIG. 3, when bi-stable optical phase shifter 238 is set to an untwisted state, passive optical phase shifter 224 and bi-stable optical phase shifter 238 together operate as a half-wave plate, shifting the phase of one linearly polarized component of light by $\pi$ radians relative to the other linearly polarized component of the light.

In procedure 386, light arriving from the first surface, is reflected back towards the first surface. In the example set forth in FIG. 1A, a reflector (i.e., mirror 106) reflects light beam 116 as a light beam 118.

After applying procedure 386, the method proceeds back to procedures 384 and 382 sequentially, whereby procedures 384 and 382 are applied to light, which was reflected in procedure 386. The relative phase between the two linearly polarized components of the light, which has been reflected in procedure 386, is shifted by the selected phase shift. In the example set forth in FIG. 1A, optical phase shifter 104 delays one of the two linearly polarized components of light beam 118 relative to the other linearly polarized component of light beam 118, by $\pi/2$ radians. The method then proceeds back to procedure 382. The reflected light is polarized by the selected polarization level, at the first surface. In the example set forth in FIG. 1D, variable polarizer 156 polarizes light beam 152 in the direction of the Y axis.

According to another aspect of the disclosed technique, the method of FIG. 7 may further include procedure 388, which is performed before procedure 382. In procedure 388, the electric field at a second surface is controlled, thereby selecting the selected phase shift. In the example set forth in FIG. 3, bi-stable optical phase shifter 238 can operate either as a transparent optical element (i.e., applying a zero relative phase shift) or a quarter-wave plate (i.e., applying a phase shift of $\pi/2$ radians). Passive optical phase shifter 224 always applies a $\pi/2$ radians relative phase shift. Hence, passive optical phase shifter 224 and bi-stable optical phase shifter 238 together form an optical phase shifter which applies either a $\pi/2$ radians phase shift or a $\pi$ radians phase shift.

Figure 8A:
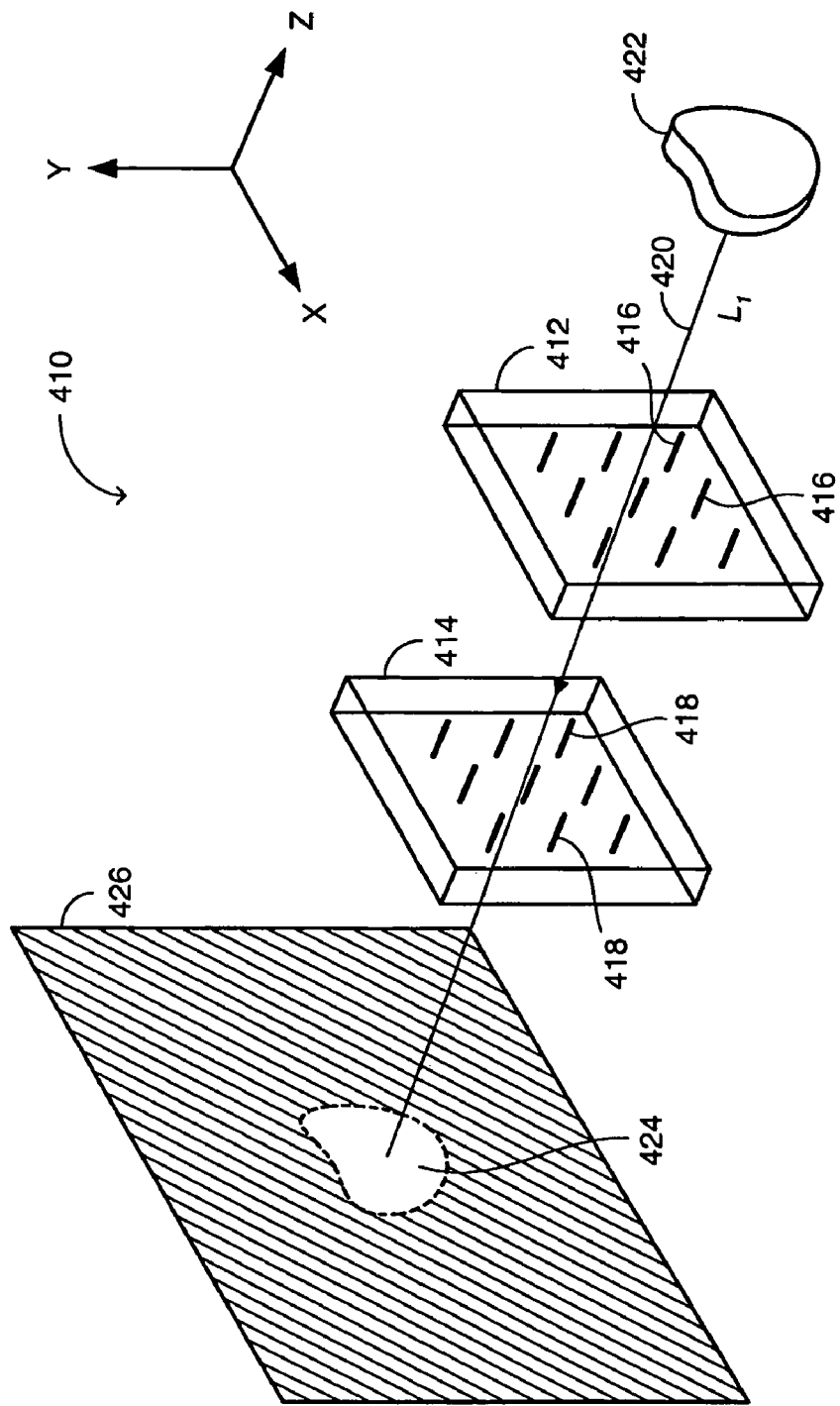
FIG. 8A is a schematic perspective view of a variable transmitter, constructed and operative in accordance with another embodiment of the disclosed technique.
Figure 8B:
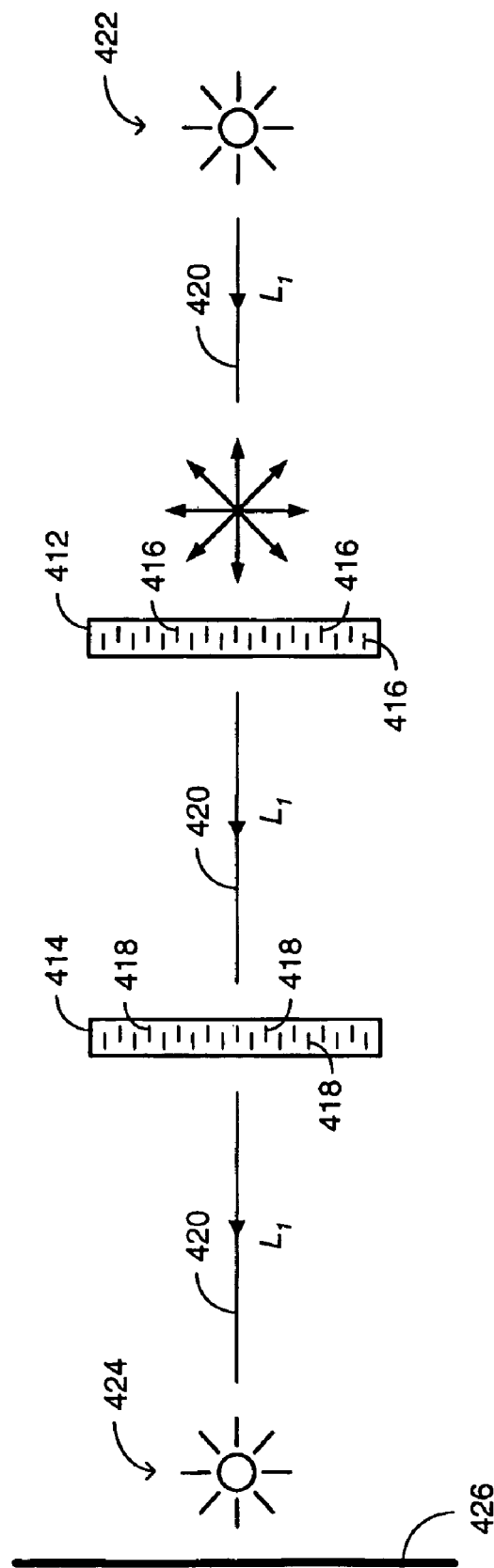
FIG. 8B is a schematic illustration of a side view of the variable transmitter of FIG. 8A.
Figure 8C:
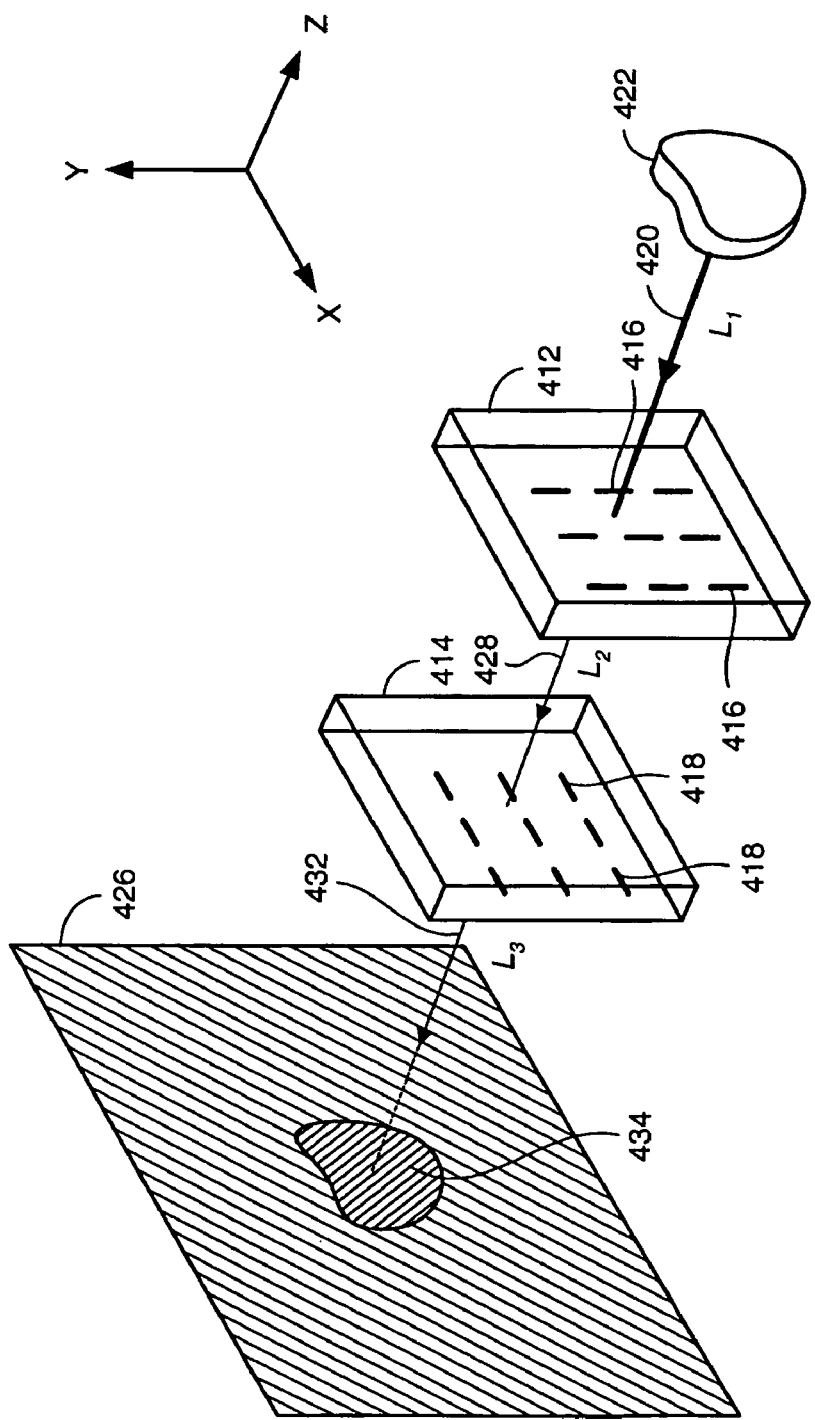
FIG. 8C is a schematic perspective view of the variable transmitter of FIG. 8A, in another mode of operation.
Figure 8D:
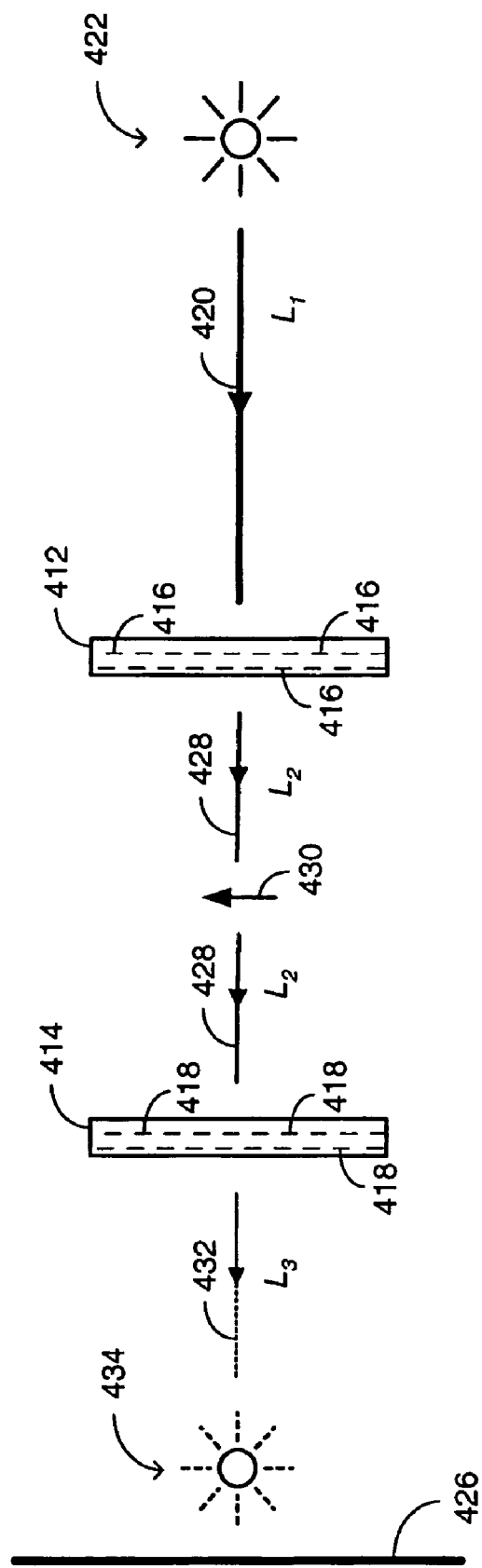
FIG. 8D is a schematic illustration of a side view of the variable transmitter of FIG. 8C.

Reference is now made to FIGS. 8A, 8B, 8C and 8D. FIG. 8A is a schematic perspective view of a variable transmitter, generally referenced 410, constructed and operative in accordance with another embodiment of the disclosed technique. FIG. 8B is a schematic illustration of a side view of the variable transmitter of FIG. 8A. FIG. 8C is a schematic perspective view of the variable transmitter of FIG. 8A, in another mode of operation. FIG. 8D is a schematic illustration of a side view of the variable transmitter of FIG. 8C.

Variable transmitter 410 includes variable polarizers 412 and 414. Each of variable polarizers 412 and 414 is similar to variable polarizer 102 as described herein above in connection with FIG. 1A. Each of variable polarizers 412 and 414 is a normally open variable polarizer. Variable polarizers 412 and 414 are positioned relative to each other in a cross-polarized manner (i.e., when in a polarizing mode, the polarization of one is perpendicular to the polarization of the other), as shall be further described in FIG. 8C. It is noted that the difference in the polarization direction of variable polarizer 412 and variable polarizer 414 can be any value, however the preferred value in order to provide maximum dynamic range, is $\pi/2$ radians.

With reference to FIGS. 8A and 8B, when no electric field is applied across variable polarizer 412, the direction of rod-shaped molecules 416 thereof, is parallel to the Z axis (i.e., perpendicular to the plane of variable polarizer 412). Likewise, when no electric field is applied across variable polarizer 414, the direction of rod-shaped molecules 418 thereof, is parallel to the Z axis (i.e., perpendicular to the plane of variable polarizer 414). Thus, when no electric field is applied across each of variable polarizers 412 and 414, the respective variable polarizer transmits the incoming light, without having any effect on the incoming light and without affecting the luminance of the incoming light. Variable polarizers 412 and 414 transmit a light beam 420 of an object 422 having a luminance $L_1$, without affecting the value of luminance $L_1$ and an observer (not shown) views an image 424 of object 422, on a viewing plane 426.

With reference to FIGS. 8C and 8D, when an electric field is applied across variable polarizer 412, rod-shaped molecules 416 tend to be aligned along the Y axis, wherein variable polarizer 412 operates as a linear polarizer and thus reduces the luminance of the incoming light. In like manner, when an electric field is applied across variable polarizer 414, rod-shaped molecules 418 tend to be aligned along the X axis, wherein variable polarizer 414 operates as a linear polarizer and thus reduces the luminance of the incoming light. Variable polarizer 412 linearly polarizes light beam 420 along the Y axis and as a result a light beam 428 emerges from variable polarizer 412 whose luminance $L_2$ is less than luminance $L_1$. The direction of polarization of light beam 428 is represented by an arrow 430. Variable polarizer 414 linearly polarizes light beam 428 along the X axis and as a result a light beam 432 emerges from variable polarizer 414 whose luminance $L_3$ is less than luminance $L_2$. The observer views an image 434 of object 422 on viewing plane 426, wherein the luminance $L_3$ of image 434 is less than luminance $L_1$ of object 422.

It is noted that a set of electrically conducting layers similar to electrically conducting layers 306 and 308 (FIG. 5) and a set of electrically insulating layers similar to electrically insulating layers 310 and 312, can be used with variable transmitter 410. One pair of electrically conducting layers applies an electric field across variable polarizer 412 and another pair of electrically conducting layers applies an electric field across variable polarizer 414. It is noted that each of the pairs of electrically conducting layers can apply a different electric field to the respective variable polarizer. For example, variable transmitter 410 can include a sequence of layers as follows: a protective layer, an electrically conducting layer, an electrically insulating layer, a variable polarizer, an electrically insulating layer, an electrically conducting layer, an electrically insulating layer, an electrically conducting layer, an electrically insulating layer, a variable polarizer, an electrically insulating layer, an electrically conducting layer and a protective layer.

Alternatively, one pair of electrically conducting layers simultaneously applies an electric field across variable polarizers 412 and 414. For example, variable transmitter 410 can include a sequence of layers as follows: a protective layer, an electrically conducting layer, an electrically insulating layer, a variable polarizer, an LC separating layer, another variable polarizer, an electrically insulating layer, an electrically conducting layer and a protective layer. The LC separating layer is made of a transparent polymer, such as nylon, and the like, which separates two adjacent variable polarizers and prevents the LC phases of these two variable polarizers to intermix. Additionally, a controller similar to controller 190 (FIG. 2) can be coupled with the electrically conducting layers and a photocell similar to photocell 188 can be coupled with the controller.

It is further noted that variable transmitter 410 can be employed in various optical devices, such as spectacles, helmet visor, welding visor, periscope, telescope, microscope, binoculars, ground vehicle window, aircraft window, spacecraft window, marine vehicle window, grazing, greenhouse window head-up display (HUD), head-mounted display (HMD), and the like. In case each of the variable polarizers is in form of a bi stable twisted nematic GHLC cell, during power failure an electric field in a predetermined pulse shape can be applied to the variable polarizers, thereby enabling the variable transmitter to transmit light at the maximum intensity. It is noted that the user can set the polarization level of variable polarizers 412 and 414, thereby setting the contrast level and the brightness of image 424.

Figure 9:
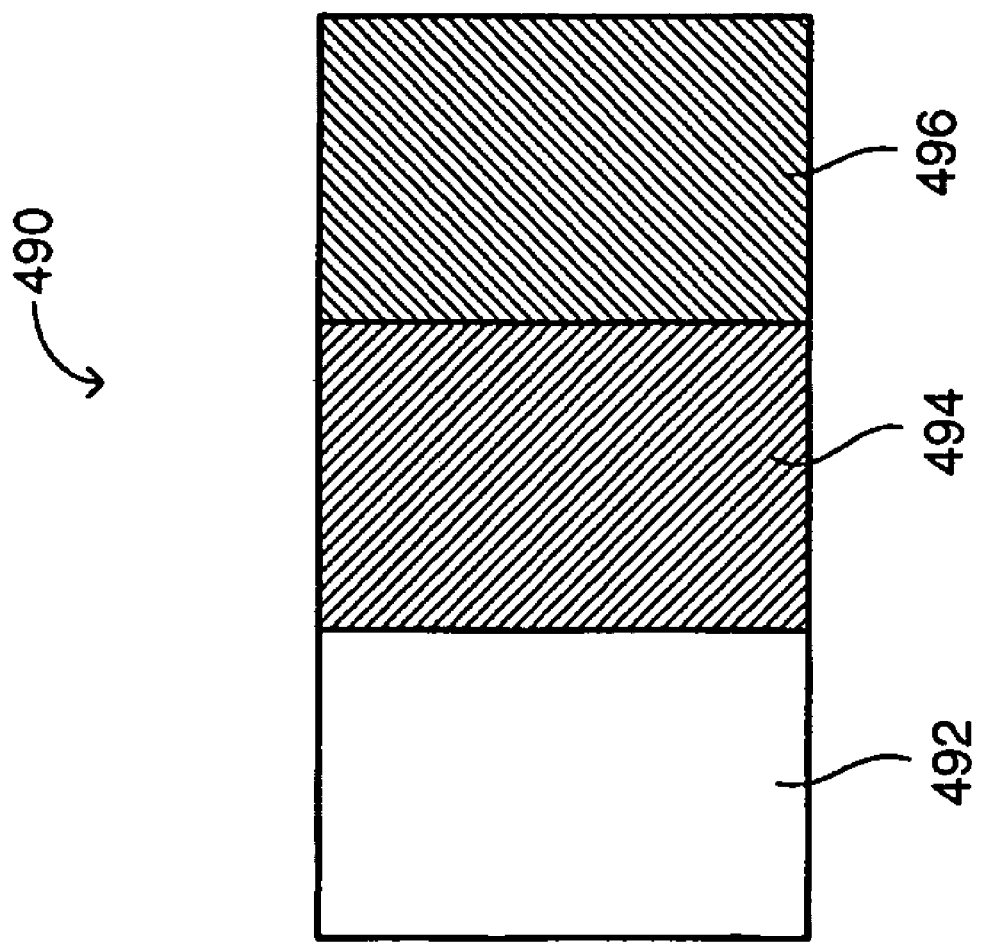
FIG. 9 is a schematic illustration of a variable transmitter, constructed and operative in accordance with a further embodiment of the disclosed technique.

Reference is now made to FIG. 9, which is a schematic illustration of a variable transmitter, generally referenced 490, constructed and operative in accordance with a further embodiment of the disclosed technique. Variable transmitter 490 can be a helmet visor, a welding visor, HUD, HMD, and the like. Variable transmitter 490 includes a plurality of transmitting regions 492, 494 and 496. Each of regions 492, 494 and 496 is similar to variable transmitter 410 as described herein above in connection with FIG. 8A. Thus, a controller (not shown) coupled with regions 492, 494 and 496 can control the applied electric voltage and hence, the applied electric field across each of the regions 492, 494 and 496, in order to transmit incoming light at a different luminance in each region. Such a controller can be further coupled with a camera, light sensors, and the like, to be operated by a user. In the example set forth in FIG. 9, region 492 is set to high transmittance, and hence appears highly transparent and regions 494 and 496 are set at low transmittance, and hence regions 494 and 496 appear dimmer than region 492.

It is noted that instead of variable transmitter 490, a variable reflector similar to variable reflector 100 as described herein above in connection with FIG. 1A, can be employed. In this case the variable reflector is divided into a plurality of reflecting regions, whose polarization level can be controlled individually.

It is further noted that each of the front variable polarizer and the rear variable polarizer in divided into a plurality of regions, similar to regions 492, 494 and 496, wherein each region of the front variable polarizer is spatially compatible with another region of the rear variable polarizer. The controller sets one region of the front variable polarizer, to the same polarization level as that of the respective region of the rear variable polarizer. Thus, the controller enables the variable transmitter to transmit light through a selected region, at a selected luminance.

Figure 10:
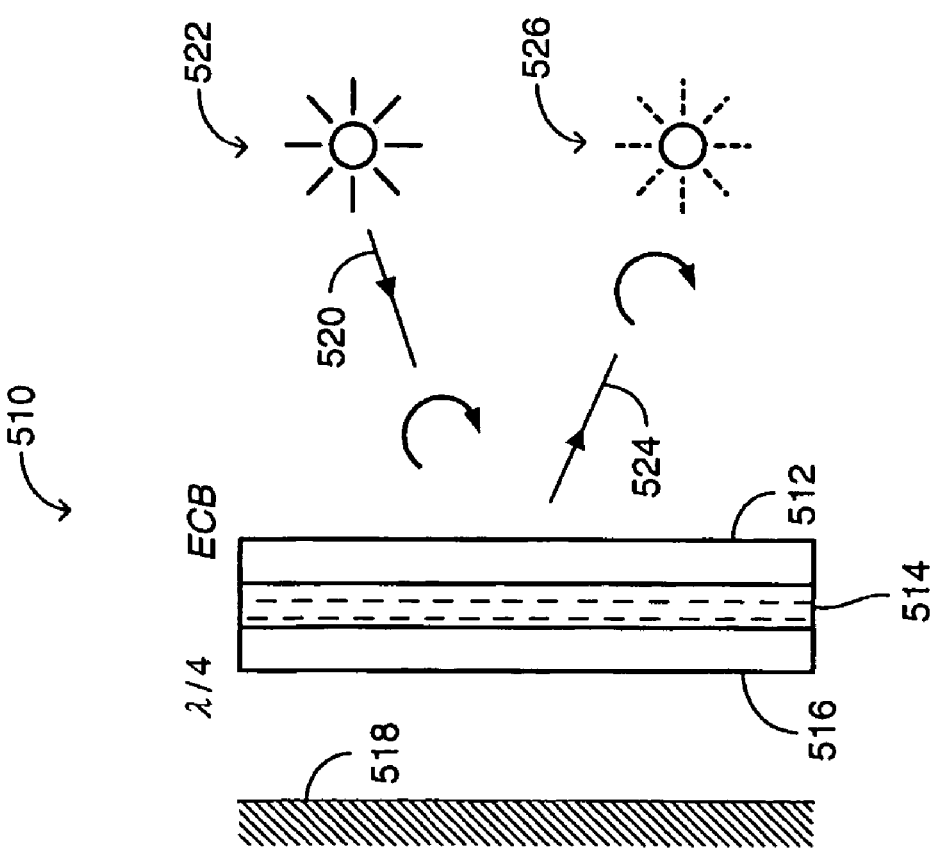
FIG. 10 is a schematic illustration of a variable reflector, constructed and operative in accordance with another embodiment of the disclosed technique.

Reference is now made to FIG. 10, which is a schematic illustration of a variable reflector, generally referenced 510, constructed and operative in accordance with another embodiment of the disclosed technique. Variable reflector 510 varies the luminance of the reflection of a generally circularly polarized light. Variable reflector 510 includes a switchable optical phase shifter 512, a variable polarizer 514, an optical phase shifter 516 and a mirror 518. Switchable optical phase shifter 512, variable polarizer 514 and optical phase shifter 516, are similar to switchable optical phase shifter 266 (FIG. 4), variable polarizer 262 and optical phase shifter 264, respectively. Variable polarizer 514 is located between switchable optical phase shifter 512 and optical phase shifter 516. Optical phase shifter 516 is located between variable polarizer 514 and mirror 518.

Switchable optical phase shifter 512 receives a circularly polarized light beam 520 from an object 522. Since no electric voltage is applied to switchable optical phase shifter 512, switchable optical phase shifter 512 operates as a quarter-wave plate. Thus, for example, switchable optical phase shifter 512 converts circularly polarized light beam 520 to a linearly polarized light beam (not shown). Variable polarizer 514 applies a selected level of polarization to the linearly polarized light beam, in a selected direction (i.e., polarization orientation). Optical phase shifter 516, together with mirror 518, rotate the linearly polarized light beam by $\pi/2$ radians, before reentering variable polarizer 514. Variable polarizer 514 then applies the same selected level of polarization, at that same direction, to the rotated linearly polarized light beam. The dual pass through variable polarizer 514 reduces the luminance of light passing there through. Switchable optical phase shifter 512 shifts the relative phase between two linearly polarized components of the light beam exiting variable polarizer 514 thus, for example, converting linearly polarized light to a circularly polarized light. A light beam 524 of reduced luminance exits variable reflector 510, thereby providing a reflected image 526 of object 522, at a reduced luminance.

It is noted that when an electric voltage is applied to switchable optical phase shifter 512, switchable optical phase shifter 512 operates as a transparent optical element, which does not retard any component of light passing there through. In this case, variable reflector 510 operates in a manner similar to that of variable reflector 180 of FIG. 2.

Figure 11:
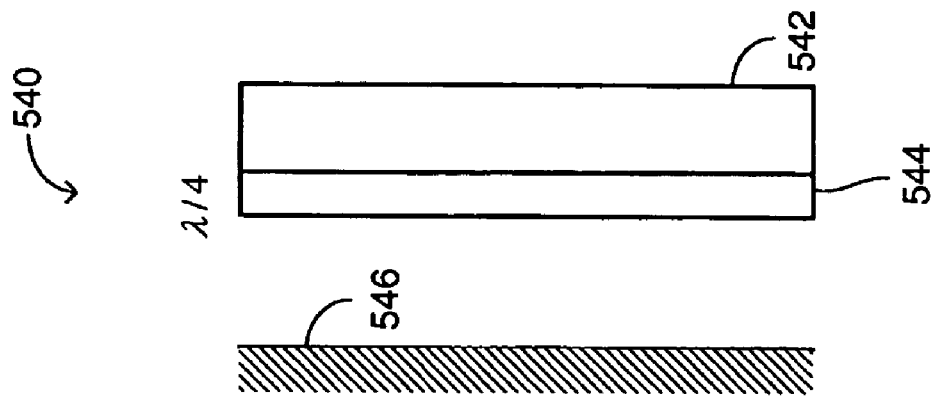
FIG. 11 is a schematic illustration of a variable reflector, constructed and operative in accordance with a further embodiment of the disclosed technique.

Reference is now made to FIG. 11, which is a schematic illustration of a variable reflector, generally referenced 540, constructed and operative in accordance with a further embodiment of the disclosed technique. Variable reflector 540 includes a variable polarizer 542, an optical phase shifter 544 and a mirror 546.

Variable polarizer 542 is constructed by integrating an optical phase shifter with a variable linear polarizer similar to variable polarizer 514. Optical phase shifter 544 is located between variable polarizer 542 and mirror 546. Variable polarizer 542 is positioned such that the switchable optical phase shifter portion thereof faces outwardly and hence, is the first to receive incoming light. Accordingly, variable polarizer 542 is an optical element which operates according to at least two modes. In the first mode, variable polarizer 542 admits components of incident light, which are circularly polarized and blocks any other component thereof. In the second mode, variable polarizer 542 substantially admits the entire incident light. Variable polarizer 542 may operate according to other modes, depending on the electric field applied thereto.

Figure 12:
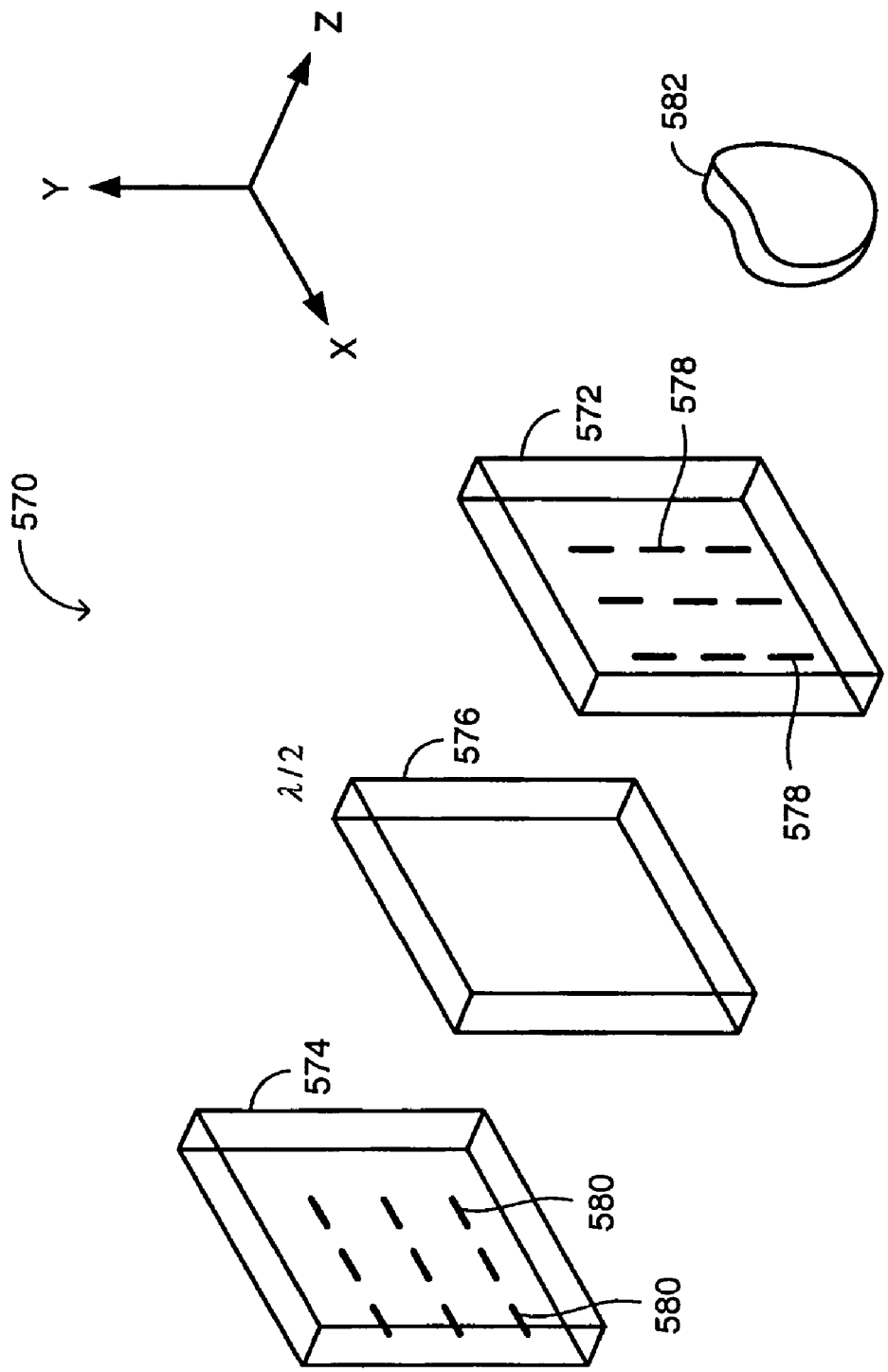
FIG. 12 is a schematic illustration of a variable transmitter, constructed and operative in accordance with another embodiment of the disclosed technique.

Reference is now made to FIG. 12, which is a schematic illustration of a variable transmitter, generally referenced 570, constructed and operative in accordance with another embodiment of the disclosed technique. Variable transmitter 570 includes variable polarizers 572 and 574 and a bi-stable optical phase shifter 576. Each of variable polarizers 572 and 574 is similar to variable polarizer 102 as described herein above in connection with FIG. 1A.

Each of variable polarizers 572 and 574 is a normally closed variable polarizer. Thus, when electric fields are applied to variable polarizers 572 and 574, rod-shaped molecules 578 and 580 of variable polarizers 572 and 574, respectively, are aligned along the Z axis. When no electric field is applied to variable polarizers 572 and 574, rod-shaped molecules 578 are aligned along the Y axis and rod-shaped molecules 580 are aligned along the X axis. Phase shifter 576 is a bi-stable optical phase shifter, which can operate either as a transparent optical element or a half-wave plate.

Variable polarizers 572 and 574 are positioned relative to each other in a cross-polarized manner (i.e., when in a polarizing mode, the polarization of one is perpendicular to the polarization of the other), as described herein above in connection with FIG. 8C. Bi-stable optical phase shifter 576 is located between variable polarizers 572 and 574.

During normal operation of variable transmitter 570, bi-stable optical phase shifter 576 operates as a transparent optical element. It is noted that bi-stable optical phase shifter 576 may be set to the transparent state thereof, by applying a pulse of predetermined shape to bi-stable optical phase shifter 576 when variable transmitter 570 is turned on, and further during the operation thereof. At this mode of operation, each of variable polarizers 572 and 574 can be set at different polarization levels, by applying electric fields of respective values.

At power failure, when variable polarizers 572 and 574 switch to the closed mode, an electric field of a predetermined pulse shape is applied to bi-stable optical phase shifter 576, so that bi-stable optical phase shifter 576 operates as a half-wave plate. Bi-stable optical phase shifter 576 retards the component of light incident there through, having an optical axis direction of 45 degrees relative to rod-shaped molecules 578 and rod-shaped molecules 580. Thus, bi-stable optical phase shifter 576 rotates the polarization angle of the light received from variable polarizer 572 and transmits this polarized light to variable polarizer 574. Since the polarization angle of the light that strikes variable polarizer 574, matches the direction of rod-shaped molecules 580, this light passes through variable polarizer 574 without a reduction in intensity. Thus, during power failure, variable transmitter 570 transmits there through approximately 50% of the (unpolarized) light arriving from an object 582 located in front of variable polarizer 572.

Figure 13:
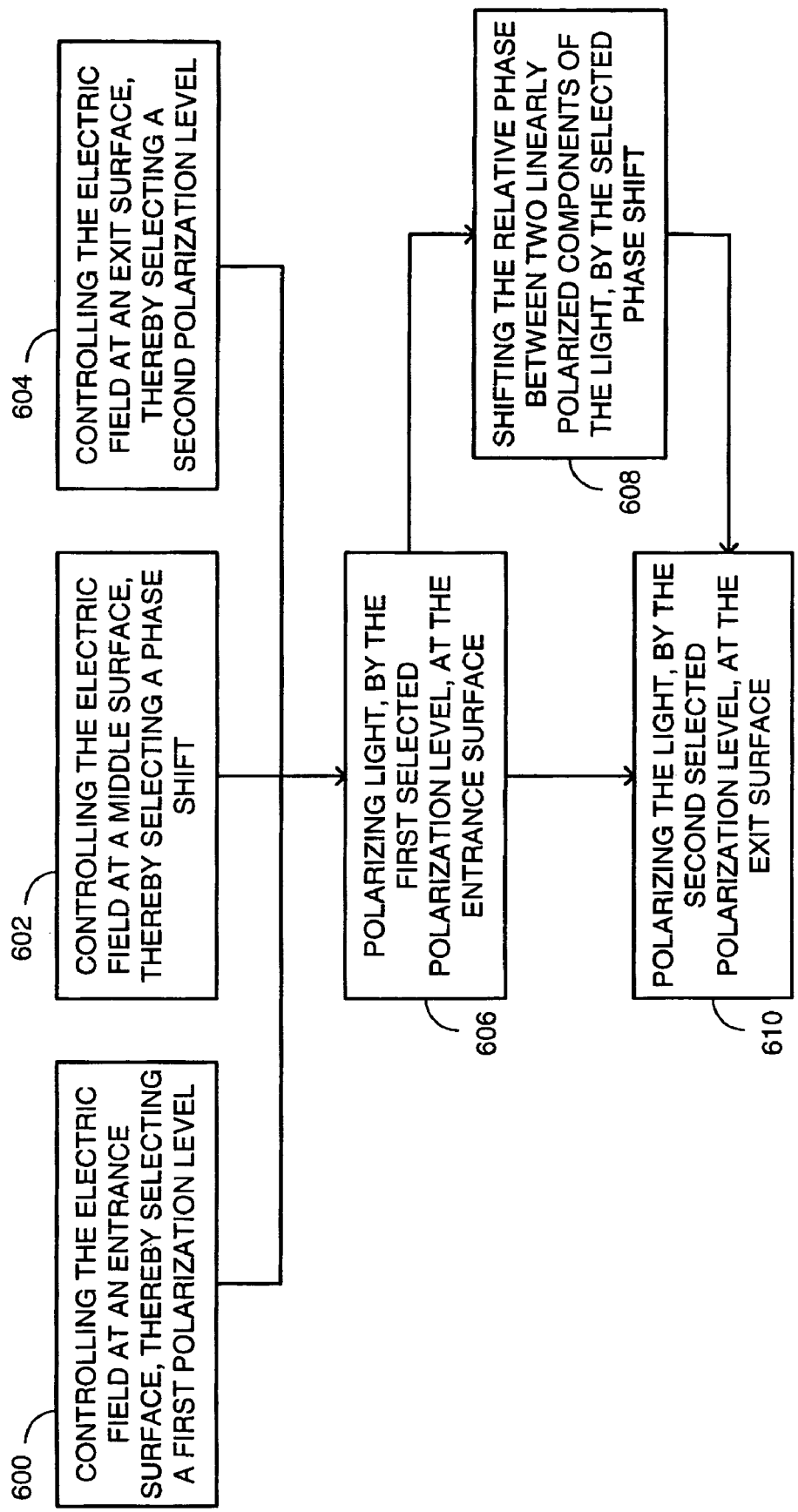
FIG. 13 is a schematic illustration of a method for transmitting light at variable intensity, operative in accordance with a further embodiment of the disclosed technique.

Reference is now made to FIG. 13, which is a schematic illustration of a method for transmitting light at a variable reflectance, operative in accordance with a further embodiment of the disclosed technique. In procedure 600, the electric field at an entrance surface is controlled, thereby selecting a first polarization level. The procedure is generally similar to procedure 380 of the method of FIG. 7. In the example set forth in FIGS. 8A and 8C, variable polarizer 416 is set to either a homeotropic state (i.e., a zero polarization level), as shown in FIG. 8A, or a planar state (i.e., a non-zero polarization level), as shown in FIG. 8C.

In procedure 602, the electric field at a middle surface is controlled, thereby selecting a phase shift. In the example set forth in FIG. 12, bi-stable optical phase shifter 576 can operate either as a transparent optical element (i.e., applying a zero phase shift) or a half-wave plate (i.e., applying a phase shift of $\pi$ radians).

In procedure 604, the electric field at an exit surface is controlled, thereby selecting a second polarization level of the exit surface. This procedure is generally similar to procedure 600. In the example set forth in FIGS. 8A and 8C, variable polarizer 418 is set to either a homeotropic state, as shown in FIG. 8A, or a planar state, as shown in FIG. 8C.

In procedure 606, light is polarized by the first selected polarization level. This procedure is generally similar to procedure 382 of the method of FIG. 7. In the example set forth in FIG. 8A, variable polarizer 416 transmits light beam 420 (i.e., applies a zero level polarization). In the example set forth in FIG. 8C, variable polarizer 416 polarizes light beam 420 in the direction of the Y axis (i.e., applies a non-zero level polarization).

In procedure 608, the relative phase between two linearly polarized components of the light, is shifted by the selected phase shift. In the example set forth in FIG. 12, bi-stable optical phase shifter 576 either operates as a transparent optical element (i.e., applies a zero phase shift to light) or as a half-wave plate (i.e., shifts the phase of one of the linearly components of light by $\pi$ radians).

In procedure 610, the light is polarized by the second selected polarization level. This procedure is generally similar to procedure 606. In the example set forth in FIG. 8A, variable polarizer 418 transmits light beam 420 (i.e., applies a zero level polarization). In the example set forth in FIG. 8C, variable polarizer 418 polarizes light beam 428 in the direction of the X axis (i.e., applies a non-zero level polarization).

It is noted that the method does not necessarily apply procedures 602 and 608. For example, variable transmitter 410 (FIG. 8A) can be operated by applying a sequence of procedures 600, 604, 606 and 610. It is further noted that procedures 600, 602 and 604 may be performed in any order or concurrently.

According to another aspect of the disclosed technique, the variable polarizer includes two protective layers enclosing a liquid crystal, a homeotropic surface alignment layer and an electrical insulating layer, wherein one of the protective layers is coated with a pair of interdigitating electrodes. When no electric voltage is applied across the pair of electrodes, the homeotropic surface alignment layer causes the rod-shaped molecules of the liquid crystal to be aligned perpendicular to the surface of the protective layers, wherein the variable polarizer applies no polarization to the incident light. When an electric voltage is applied across the pair of electrodes, the electric field generated between the electrodes, causes the rod-shaped molecules to be aligned with respect to the generated electric field (i.e., with components parallel to the surface of the protective layers), wherein the variable polarizer applies polarization to the incident light.

Figure 14A:
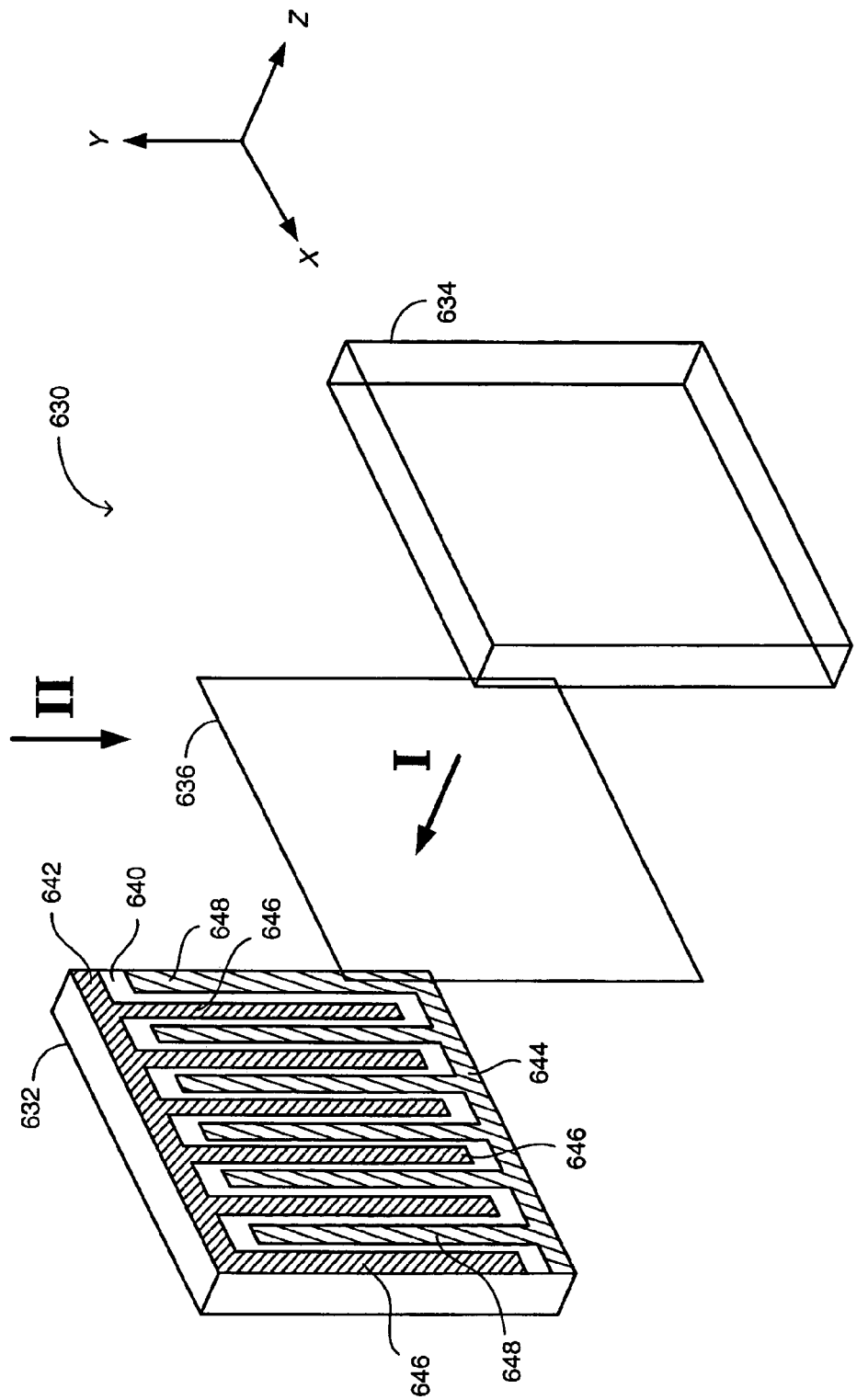
FIG. 14A is a schematic blown-up illustration in perspective of a variable polarizer, constructed and operative in accordance with another embodiment of the disclosed technique.
Figure 14C:
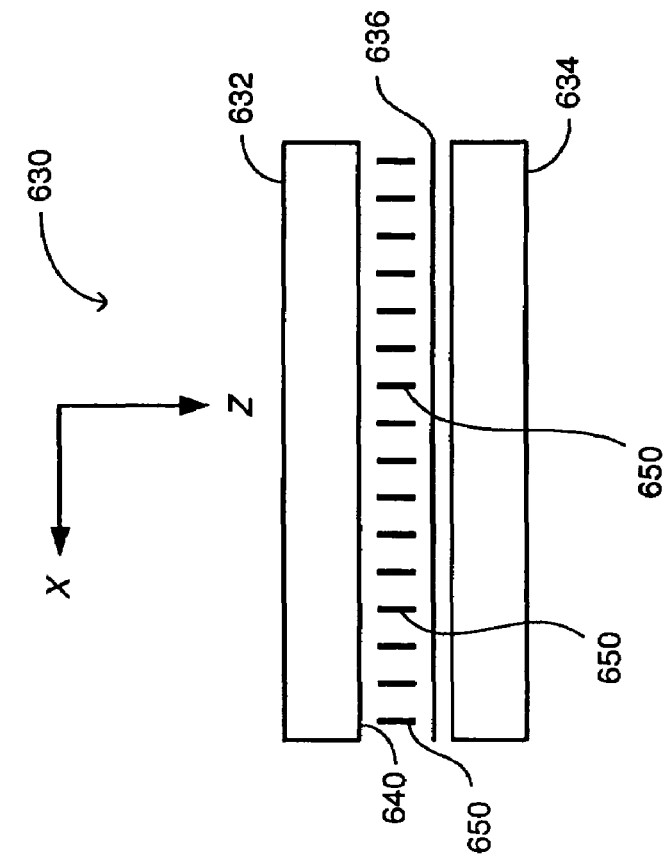
FIG. 14C is a schematic illustration of view II (top view) of the variable polarizer of FIG. 14A in an assembled form and when no electric field is applied across the pair of electrodes of the protective layer of the variable polarizer of FIG. 14A.
Figure 14B:
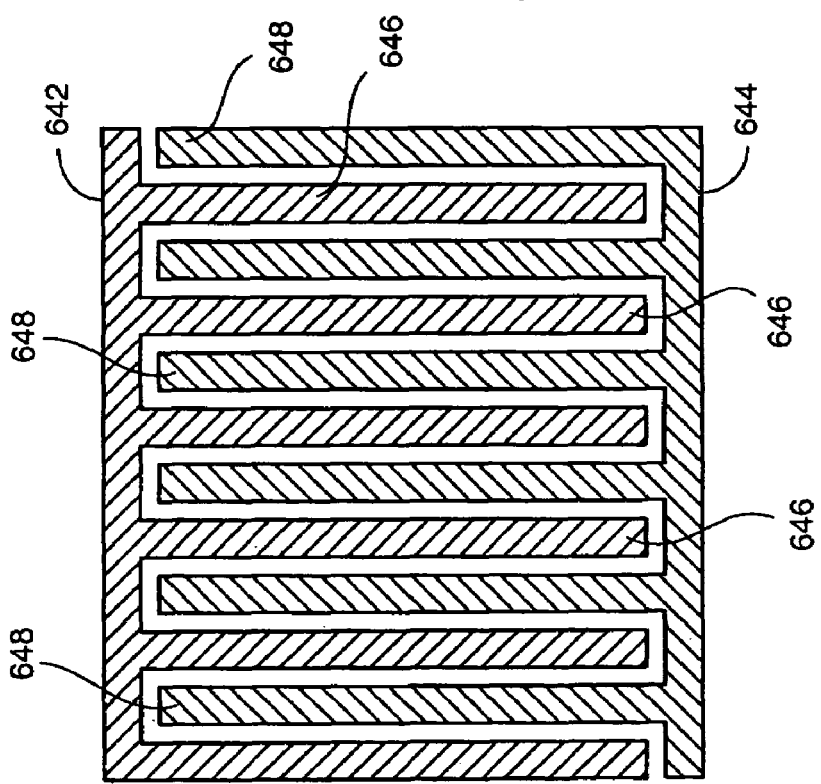
FIG. 14B is a schematic illustration of view I (front view) of one of the protective layers of the variable polarizer of FIG. 14A, when no electric voltage is applied across the pair of electrodes of the protective layer.
Figure 14E:
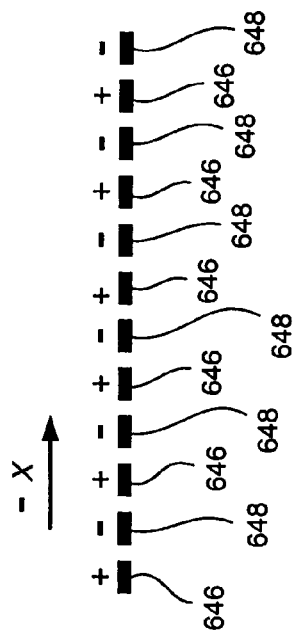
FIG. 14E is a schematic illustration of cross section III of the pair of electrodes of FIG. 14D.
Figure 14F:
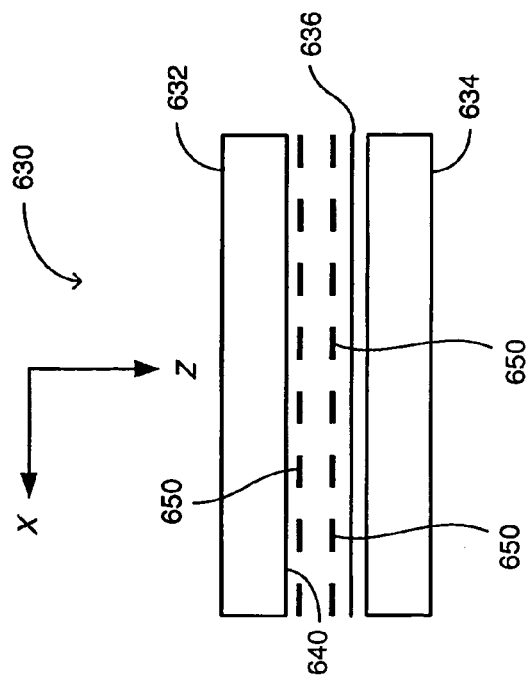
FIG. 14F is a schematic illustration of view II (top view) of the variable polarizer of FIG. 14A in an assembled form, having an LC material of positive dielectric anisotropy and a guest material of positive optical anisotropy, and when an electric field is applied across the pair of electrodes of the protective layer of the variable polarizer of FIG. 14A.
Figure 14D:
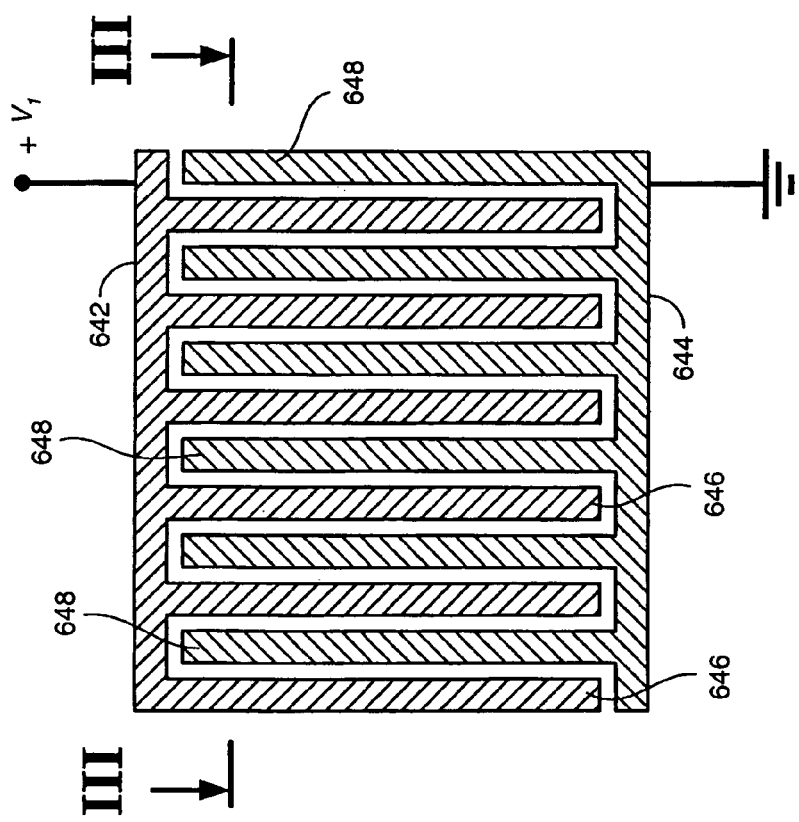
FIG. 14D is a schematic illustration of view I (front view) of one of the protective layers of the variable polarizer of FIG. 14A, when an electric voltage is applied across the pair of electrodes of the protective layer.
Figure 14G:
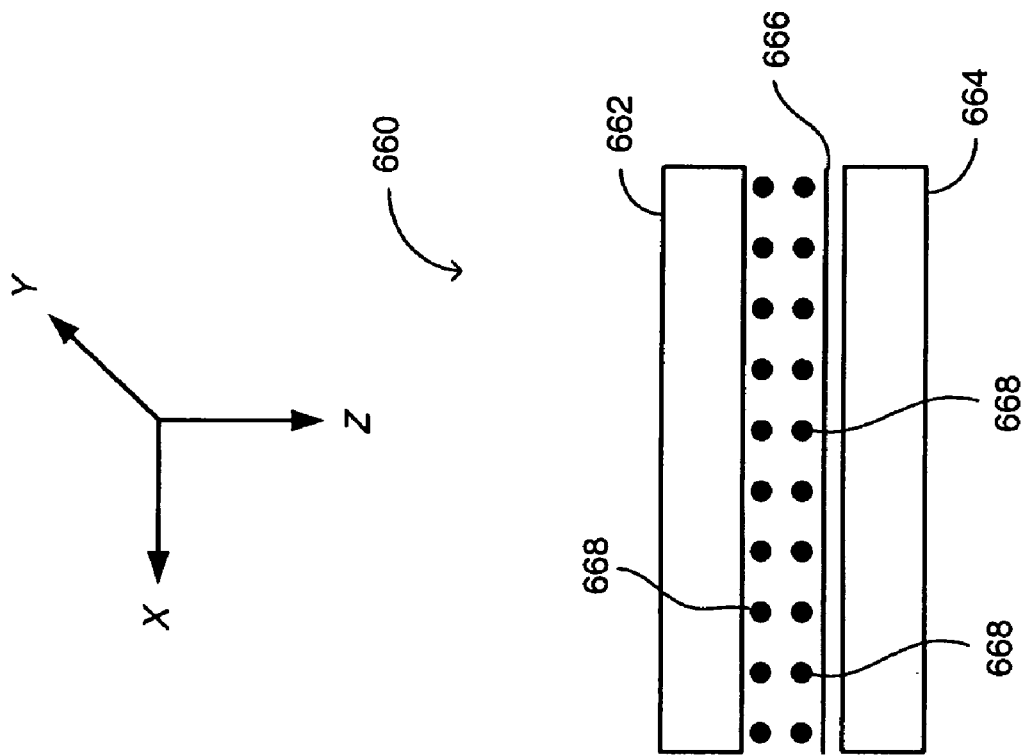
FIG. 14G is a schematic illustration of view II (top view) of a variable polarizer similar to the variable polarizer of FIG. 14A in an assembled form, constructed and operative in accordance with a further embodiment of the disclosed technique.

Reference is now made to FIGS. 14A, 14B, 14C, 14D, 14E and 14F. FIG. 14A is a schematic blown-up illustration in perspective of a variable polarizer, generally referenced 630, constructed and operative in accordance with another embodiment of the disclosed technique. FIG. 14B is a schematic illustration of view I (front view) of one of the protective layers of the variable polarizer of FIG. 14A, when no electric voltage is applied across the pair of electrodes of the protective layer. FIG. 14C is a schematic illustration of view II (top view) of the variable polarizer of FIG. 14A in an assembled form and when no electric field is applied across the pair of electrodes of the protective layer of the variable polarizer of FIG. 14A. FIG. 14D is a schematic illustration of view I (front view) of one of the protective layers of the variable polarizer of FIG. 14A, when an electric voltage is applied across the pair of electrodes of the protective layer. FIG. 14E is a schematic illustration of cross section III of the pair of electrodes of FIG. 14D. FIG. 14F is a schematic illustration of view II (top view) of the variable polarizer of FIG. 14A in an assembled form, having an LC material of positive dielectric anisotropy and a guest material of positive optical anisotropy, and when an electric field is applied across the pair of electrodes of the protective layer of the variable polarizer of FIG. 14A. FIG. 14G is a schematic illustration of view II (top view) of a variable polarizer similar to the variable polarizer of FIG. 14A in an assembled form, generally referenced 660, constructed and operative in accordance with a further embodiment of the disclosed technique.

With reference to FIG. 14A, variable polarizer 630 includes protective layers 632 and 634, an alignment layer 636 and a light affecting substance (e.g., GHLC). Each of protective layers 632 and 634 is similar to protective layer 302 (FIG. 5), as described herein above. Alignment layer 636 is made of an inorganic dielectric material, such as silicon dioxide or an organic dielectric material, such as polyvinyl alcohol, polyimide, photopolymerized substance, and the like. The molecules (not shown) of these types of alignment layers have side-branches (as in grafted polymers), which as a result of congestion (steric hindrance) move out of the plane of the molecular layer, thereby protruding from this plane and giving a homeotropic effect to alignment layer 636. A photopolymerized self alignment layer can be constructed by polymerizing the molecules of an alignment layer, thereby forming either a homeotropic or a planar alignment layer. In the example set forth in FIGS. 14A, 14B, 14C, 14D, 14E, 14F and 14G, alignment layer 636 is a homeotropic alignment layer.

The liquid crystal can be either of class 1 (dispersed) or class 2 (homogenous) and each class can be either in form of a mixture or a chemical compound, as described herein above.

A surface 640 of protective layer 632 facing alignment layer 636 is coated with an electrically conductive and transparent material, such as electrically conducting layer 306 (FIG. 5), as described herein above. Surface 640 is then etched by photolithography, into the shape of a pair of electrodes 642 and 644. Electrodes 642 and 644 possess a plurality of prongs 646 and 648, respectively, wherein prongs 646 and 648 intermingle. Electrodes 642 and 644 are coupled with a power source (not shown) and the output of the power source is controlled by a controller (not shown), similar to controllers 190, 230 and 270 as described herein above in connection with FIGS. 2, 3 and 4, respectively. Electrode 642 is coupled with one pole of the power source and electrode 644 is coupled with the other pole of the power source. The arrangement of electrodes 642 and 644 in this manner, is referred to herein below, as "in-plane configuration".

Alignment layer 636 is located between protective layers 632 and 634. Electrodes 642 and 644 are located on surface 640 of protective layer 632 and electrodes 642 and 644 are located between protective layer 632 and alignment layer 636. After assembly of protective layers 632 and 634, and alignment layer 636, the edges (not shown) of variable polarizer 630 are sealed with an adhesive and the gaps between protective layers 632 and 634, and alignment layer 636 are filled with the liquid crystal, or preferably with a suitable spacer material.

With reference to FIGS. 14B and 14C, no electric voltage is applied across electrodes 642 and 644 (i.e., an un powered condition). Due to the presence of alignment layer 636, rod shaped molecules 650 of the liquid crystal are aligned along the Z axis (i.e., perpendicular to surface 640 and the surfaces—not shown—of variable polarizer 630 ). Thus, when no electric voltage is applied across electrodes 642 and 644, variable polarizer 630 transmits the incident light without affecting the incident light (i.e., variable polarizer 630 is of the normally open type). In this case, the anisotropic light absorbing particles (i.e., the dye molecules) align along the direction of the molecules of the optically active substance (e.g., the liquid crystal molecules), and the anisotropic light absorbing particles do not affect the incident light in any way.

Thus, when alignment layer 636 is a homeotropic alignment layer, the dielectric anisotropy of the host molecules is positive and the optical anisotropy of the guest molecules is positive, variable polarizer 630 is normally open (N.O.) (i.e., variable polarizer 630 transmits the incoming light, when no electric field is applied across electrodes 642 and 644). Accordingly, using the in-plane electrode configuration in conjunction with homeotropic alignment and a positive-positive GH material combination, provides a new cell driving variant of the N.O. (clear) type.

With reference to FIG. 14D, the controller controls the operation of the power source to apply a voltage $V_1$ across electrodes 642 and 644 (i.e., a powered condition). With reference to FIG. 14E, an electric field is generated by every pair of contiguous prongs 646 and 648, in direction of –X. With reference to FIG. 14F, rod-shaped molecules 650 having positive dielectric anisotropy, are aligned along the generated electric fields (i.e., along the X axis and parallel with surface 640 and the surfaces of protective layers 632 and 634). Thus, when an electric voltage is applied across electrodes 642 and 644, variable polarizer 630 applies a polarization to the incident light, at a level which corresponds to the value of the applied electric voltage.

Variable polarizer 630 can have either a positive radius of curvature (i.e., being convex), a negative radius of curvature (i.e., being concave), or a combination of positive and negative radii of curvature (i.e., an arbitrary curved plane), as well as being substantially flat. Variable polarizer 630 can be used in a liquid environment as well as in a gaseous one. Variable polarizer 630 can be flexible as well as being rigid.

It is noted that the liquid crystal of variable polarizer 630 can be a multi-stable GHLC. For example, the liquid crystal can be in the form of a bi-stable (i.e., having two stable states) twisted nematic liquid crystal, a bi-stable polymer stabilized liquid crystal, a bi-stable surface stabilized liquid crystal, and the like. In this case, the application of a predetermined electric pulse across electrodes 642 and 644, causes rod-shaped molecules 650 to be aligned either along the Z axis or the X axis.

It is further noted that variable polarizer 630 can be incorporated with a variable reflector similar to variable reflector 100 (FIG. 1A). A pair of variable polarizers 630 can be employed as a variable transmitter, similar to variable transmitter 410 (FIG. 8A). In this case, different voltages can be applied across the electrodes of the two variable polarizers, thereby allowing control of the intensity of the incident light passing through the variable transmitter. It is further noted that since each of these variable polarizers is of the normally open type, the variable reflector or the variable transmitter which employs these variable polarizers is a fail-safe type variable reflector or variable transmitter, respectively, (i.e., either of variable reflector or the variable transmitter, reflects the incident light or transmits the incident light, respectively, without affecting the intensity of the incident light, in case of power failure).

It is further noted that the dielectric anisotropy of the host molecules (i.e., rod-shaped molecules) of the variable polarizer, wherein the electrodes are arranged in an in-plane configuration, can be either positive or negative. Likewise, the optical anisotropy of the guest molecules (e.g., dichroic or pleochroic dye molecules), can be either positive or negative. By constructing the variable polarizer from different combinations of host molecules and guest molecules, the variable polarizer can operate in the following manners, as summarized in Table I. The parallel-plane mode of operation as summarized in Table I, is described herein below in connection with FIG. 15A.

TABLE I

GH-LC cell parameters for homeotropic aligned cells for two electrode structures and four GH anistropy combinations.

| GH-Material + Electrode Structure | Cell parameters and operation | | | | | |
|---|---|---|---|---|---|---|
| | Power off | | | Power on | | |
| | Phase | Director | T-state | Phase | Director | T-state |
| 1. In-plane | | | | | | |
| LC-p + G-p | Homeo-tr. | Z | open | Q-planar | X | Closed |
| LC-p + G-n | | | closed | Q-planar | X | Semi |
| LC-n + G-p | | | open | Q-planar* | Y | Closed |
| LC-n + G-n | | | closed | Q-planar* | Y | Semi |
| 2. Parallel plane | | | | | | |
| LC-p + G-p | Homeo-tr. | Z | open | Homeo-tr. | Z | Open |
| LC-p + G-n | | | closed | Homeo-tr. | Z | Closed |
| LC-n + G-p | | | open | Planar | Y (or X) | Closed |
| LC-n + G-n | | | closed | Planar | Y (or X) | Semi |

Figure 15A:
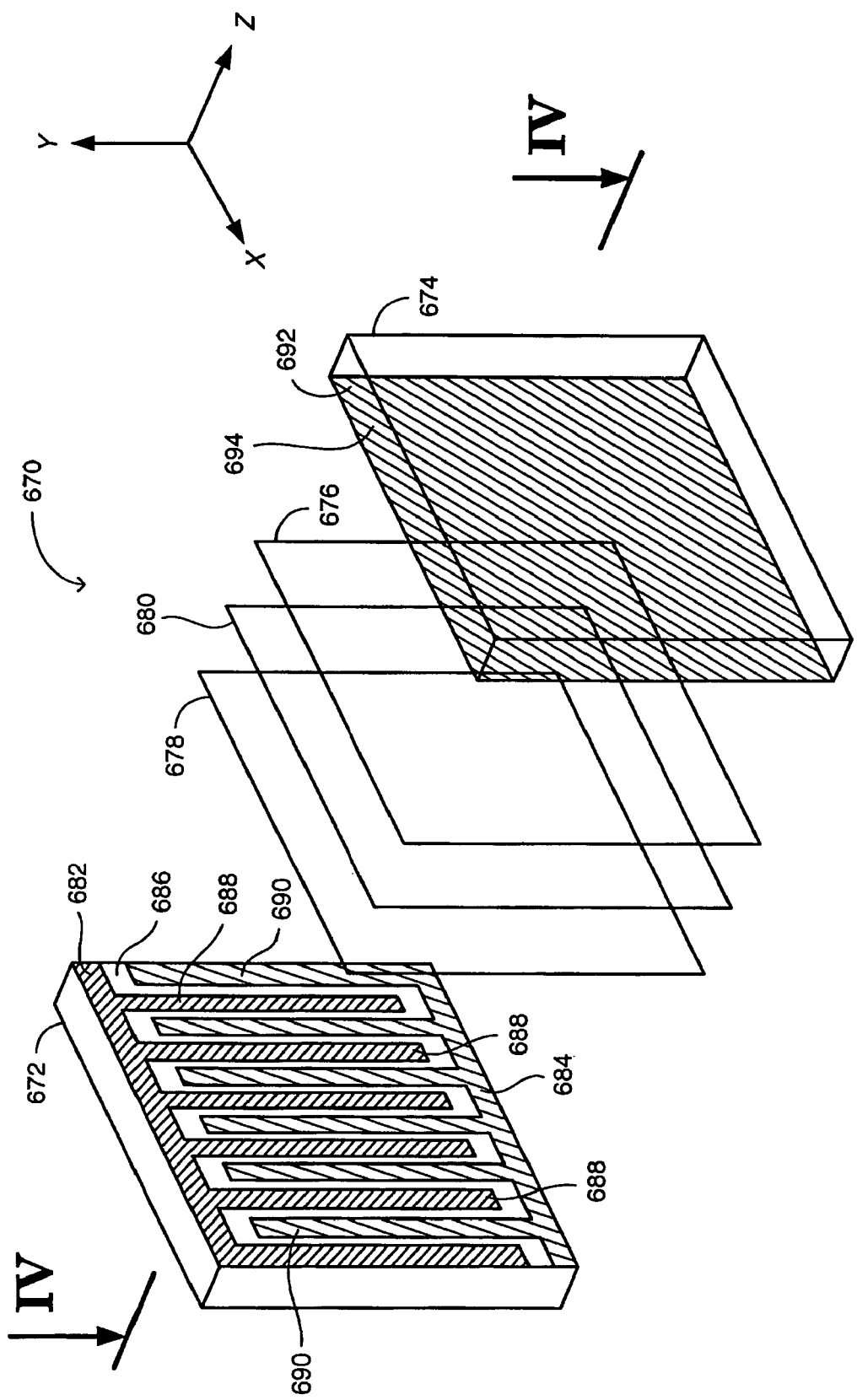
FIG. 15A is a schematic blown-up illustration in perspective of a variable polarizer, constructed and operative in accordance with another embodiment of the disclosed technique.

Wherein:
-p - positive
-n - negative
G - guest dye molecule
T-state - transmittance state
Homeo-tr. - homeotropic phase which has vertical (Z) alignment
Q-planar - quasi planar phase which has some out-of-plane components
*most probable alignment; less energetically favored would be a quasi homeotropic phase
Semi - means semitransparent due to out-of-plane components
The combinations of LC-p and LC-n refer to positive or negative dielectric anisotropy of liquid crystal, respectively, whereas the combinations of G-p and G-n refer to positive or negative optical anisotropy of the guest dye molecule, respectively The directors correspond to the axes of the coordinate system illustrated in FIG. 14A, and FIG. 15A as described herein below.

With reference to FIG. 14G, variable polarizer 660 includes protective layers 662 and 664 and an alignment layer 666. Alignment layer 666 is a homeotropic alignment layer and is located between protective layers 662 and 664. The host molecules of variable polarizer 660 have negative dielectric anisotropy, the guest molecules thereof have positive optical anisotropy. When an electric field is applied across a pair of electrodes similar to electrodes 642 (FIG. 14D) and 644, rod-shaped molecules 668 of variable polarizer 660 are aligned along the Y direction (see Table I herein above for in-plane electrode structure and LC-n+G-p GH material).

It is noted that since rod-shaped molecules 668 align along the pair of electrodes similar to electrodes 642 and 644, the contrast of a polarized image (not shown) which variable polarizer 660 polarizes, is greater than that of variable polarizer 630. Both configurations illustrated in FIGS. 14F and 14G, as described herein above, exhibit simple homogenous homeotropic alignment, electrical uniformity, and are highly reproducible in manufacturing.

It is noted that variable polarizer 630 can be incorporated with variable reflector 100 (FIG. 1A), replacing variable polarizer 102. Variable polarizer 630 can also be incorporated with variable transmitter 410 (FIG. 8A), replacing variable polarizers 412 and 414.

Figure 15D:
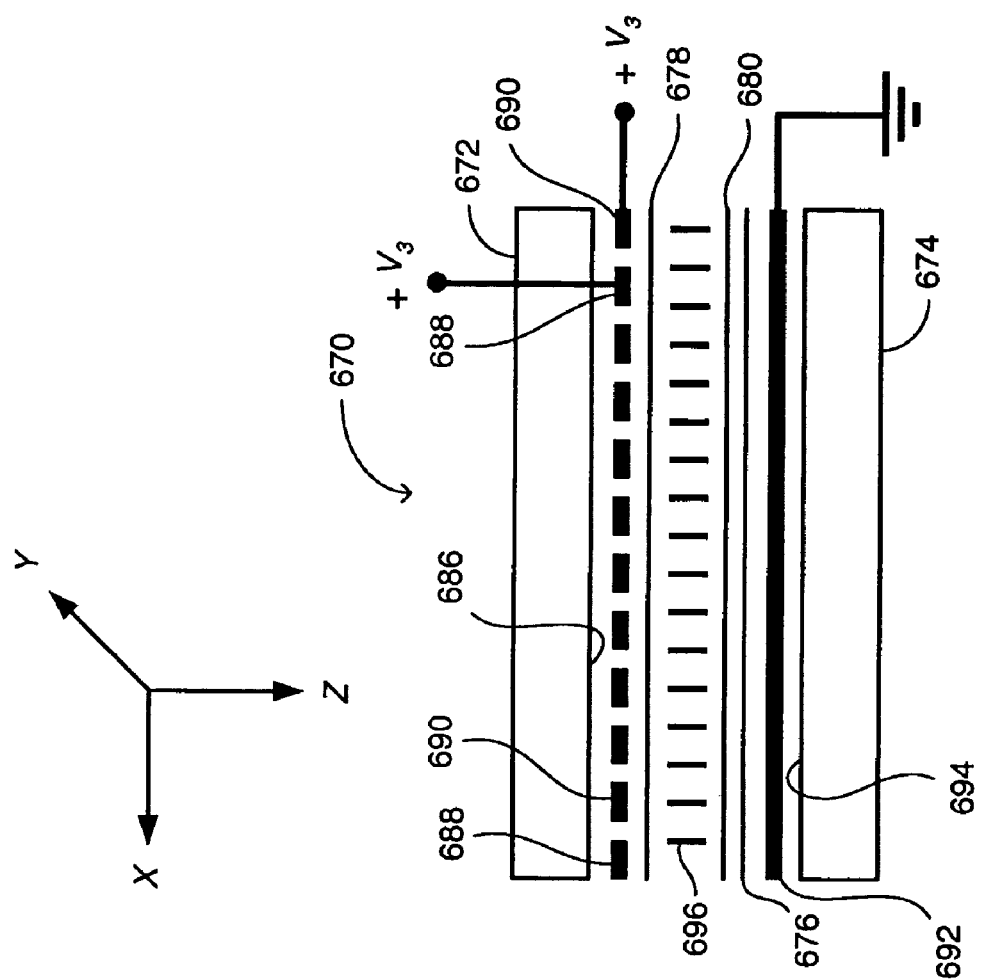
FIG. 15D is a schematic illustration of cross section IV of the variable polarizer of FIG. 15A, operating in a parallel-plane mode.

Reference is now made to FIGS. 15A, 15B, 15C and 15D. FIG. 15A is a schematic blown-up illustration in perspective of a variable polarizer, generally referenced 670, constructed and operative in accordance with another embodiment of the disclosed technique. FIG. 15B is a schematic illustration of cross section IV of the variable polarizer of FIG. 15A, when no electric voltage is applied across the interdigitating electrodes and the planar electrode of the protective layers of the variable polarizer of FIG. 15A. FIG. 15C is a schematic illustration of cross section IV of the variable polarizer of FIG. 15A, operating in an in-plane mode. FIG. 15D is a schematic illustration of cross section IV of the variable polarizer of FIG. 15A, operating in a parallel-plane mode.

With reference to FIG. 15A, variable polarizer 670 includes protective layers 672 and 674, electrically insulating layers 676 and 678, an alignment layer 680 and a light affecting substance (not shown). Each of protective layers 672 and 674 is similar to protective layer 302 (FIG. 5), as described herein above. Each of electrically insulating layers 676 and 678 is similar to electrically insulating layer 310 (FIG. 5), as described herein above. Alignment layer 680 is similar to alignment layer 636 (FIG. 14A), as described herein above. In the example set forth in FIGS. 15A, 15B, 15C and 15D, alignment layer 680 is a homeotropic alignment layer. In the example set forth in FIGS. 15A, 15B, 15C and 15D, the LC host molecules have a positive dielectric anisotropy and the guest molecules have a positive optical anisotropy. The light affecting substance can be either of class 1 (dispersed) or class 2 (homogenous) and each class can be either in form of a mixture or a chemical compound, as described herein above.

Protective layer 672 is coated with a pair of interdigitating electrodes 682 and 684 on a surface 686 of protective layer 672. Interdigitating electrodes 682 and 684 are constructed in a manner similar to the construction of electrodes 642 (FIG. 14A) and 644, as described herein above. Interdigitating electrodes 682 and 684 include a plurality of prongs 688 and 690, respectively. Protective layer 674 is coated with a planar electrode 692 on a surface 694 thereof. Planar electrode 692 is made of an electrically conductive and transparent material, such as electrically conducting layer 306 (FIG. 5), as described herein above.

Alternatively, planar electrode 692 could be made of a reflective metallic material, so as to serve at the same time as the mirror layer in ADM applications.

Electrically insulating layer 676 is located between protective layer 674 and alignment layer 680. Alignment layer 680 is located between electrically insulating layer 676 and electrically insulating layer 678. Electrically insulating layer 678 is located between alignment layer 680 and protective layer 672. Interdigitating electrodes 682 and 684 are located on surface 686 of protective layer 672 and interdigitating electrodes 682 and 684 are located between protective layer 672 and electrically insulating layer 678. Planar electrode 692 is located on surface 694 of protective layer 674 and planar electrode 692 is located between protective layer 674 and electrically insulating layer 676.

Interdigitating electrodes 682 and 684 and planar electrode 692 are coupled with a power source (not shown) and the output of the power source is controlled by a controller (not shown), similar to controllers 190, 230 and 270 as described herein above in connection with FIGS. 2, 3 and 4, respectively. The controller controls the coupling between the poles of the power source and interdigitating electrodes 682 and 684 and planar electrode 692, thereby allowing operation of variable polarizer 670, either in the in-plane mode (as described herein above in connection with FIG. 14A), or the parallel-plane mode (as described herein above in connection with FIG. 5). The controller controls also the power output of the power source, thereby allowing variable polarizer 670 to apply various levels of polarization and absorbance to the incoming light.

With reference to FIG. 15B, no electric voltage is applied across interdigitating electrodes 682 and 684 and planar electrode 692. Due to the presence of alignment layer 680, rod-shaped molecules 696 of the light affecting substance are aligned along the Z axis (i.e., perpendicular to surface 686 and 694). Thus, when no electric voltage is applied across interdigitating electrodes 682 and 684 and planar electrode 692, variable polarizer 670 transmits the incident light without affecting the incident light (i.e., variable polarizer 670 is of the normally open type).

With reference to FIG. 15C, the controller couples prongs 688 of interdigitating electrodes 682 to one pole of the power source and prongs 690 of interdigitating electrode 684 to the other pole of the power source, thereby applying a voltage $V_2$ across prongs 688 and 690. In this case, variable polarizer 670 operates in the in-plane mode as described herein above in connection with FIG. 14A. The electric field generated between prongs 688 and 690 causes rod-shaped molecules 696 to be aligned along the X axis (see Table I herein above, for in-plane electrode structure and LC-p+G-p GH material). Thus, variable polarizer 670 applies a polarization level to the incoming light, thereby switching to the closed state.

With reference to FIG. 15D, the controller couples interdigitating electrodes 682 and 684 with one pole of the power source and planar electrode 692 with the other pole of the power source. The power source applies a voltage $V_3$ between interdigitating electrodes 682 and 684 on one hand and planar electrode 692 on the other hand. In this case, variable polarizer 670 operates in the parallel-plane mode, wherein the electric field generated between interdigitating electrodes 682 and 684 on one hand and planar electrode 692 on the other, causes rod-shaped molecules 696 to be aligned along the Z axis (see Table I for parallel-plane electrode structure and LC-p+G-p GH material). Thus, variable polarizer 670 reverts back to the open state.

It is noted that the switch from closed state back to the open state, by switching off the electric power in the in-plane mode of operation (i.e., FIG. 15B), takes an order of magnitude longer than switching on the electric power in the parallel-plane mode of operation (i.e., FIG. D). This switching time depends on the magnitude of the electric field, the pulse shape, the thermal molecular movements and the materials and parameters of variable polarizer 670. The conservation in switching time applies to other combinations of dielectric anisotropy and optical anisotropy of the host molecules and the guest molecules, respectively, in a variable polarizer with homeotropic alignment (Table I, herein above), as well as planar alignment (Table II, herein below).

Thus, the combination of in-plane mode and parallel-plane mode of operation in variable polarizer 670, allows a more flexible operation, and a more rapid switching between different illumination levels. Furthermore, the combination of in-plane mode and parallel-plane mode of operation in variable polarizer 670, provides an image with improved contrast and allows to control the spatial molecular anisotropy, more efficiently.

Additional multi-drive schemes using the simultaneous in-plane and parallel-plane configuration may be derived from Tables I and II. Table II summarizes the various possible combinations of GH material anisotropy in conjunction with the planar alignment and the two different electrode configurations (i.e., in-plane configuration and parallel-plane configuration).

TABLE II

GH-LC cell parameters for planar aligned cells for two electrode structures and four GH anisotropy combinations.

| GH-Material + Electrode Structure | Cell parameters and operation | | | | | |
|---|---|---|---|---|---|---|
| | Power off | | | Power on | | |
| | Phase | Director | T-state | Phase | Director | T-state |
| 1. In-plane | | | | | | |
| LC-p + G-p | planar | Y* (or X) | Closed | Q-planar | X | Closed* |
| LC-p + G-n | | | Open | Q-planar | X | open* |
| LC-n + G-p | | | Closed | Q-planar* | Y (or X) | Closed* |
| LC-n + G-n | | | Open | Q-planar* | Y (or X) | open* |
| 2. Parallel plane | | | | | | |
| LC-p + G-p | Planar | Y* (or X) | Closed | Homeo-tr. | Z | Open |
| LC-p + G-n | | | Open | Homeo-tr. | Z | Closed |

TABLE II-continued

GH-LC cell parameters for planar aligned cells for two electrode structures and four GH anisotropy combinations.

| GH-Material + Electrode Structure | Cell parameters and operation | | | | | |
|---|---|---|---|---|---|---|
| | Power off | | | Power on | | |
| | Phase | Director | T-state | Phase | Director | T-state |
| LC-n + G-p | | | Closed | Planar | X* (or Y) | Closed |
| LC-n + G-n | | | Open | Planar | X* (or Y) | Open |

Figure 16:
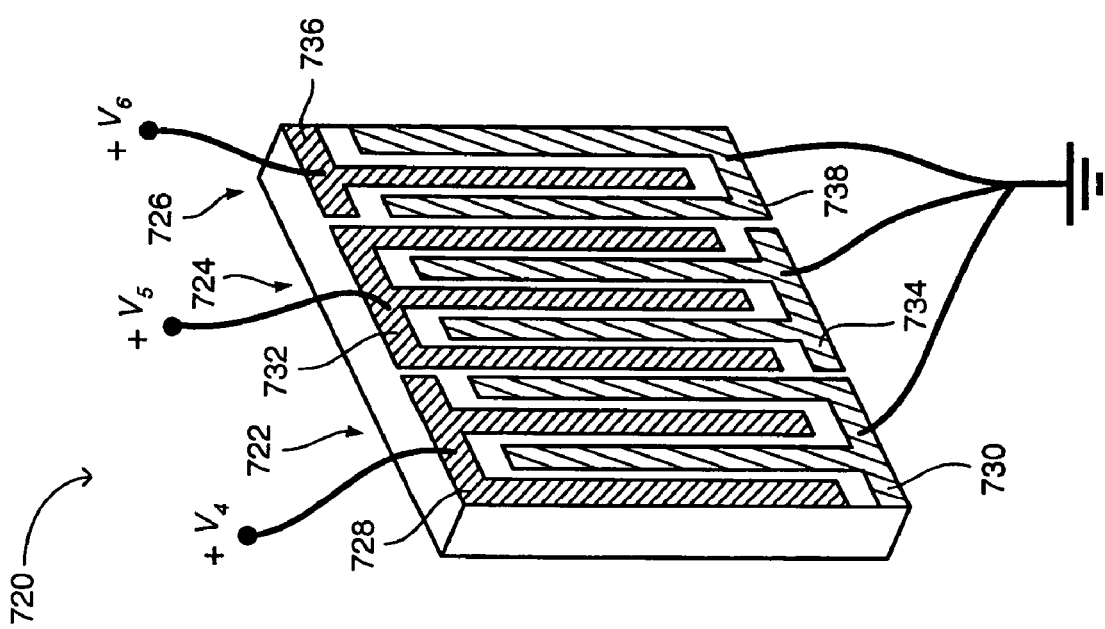
FIG. 16 is a schematic illustration in perspective of a protective layer of a variable polarizer, constructed and operative in accordance with a further embodiment of the disclosed technique.

Wherein:
-p - positive
-n - negative
G - guest dye molecule
T-state - transmittance state
Homeo-tr. - homeotropic phase which has vertical (Z) alignment
Q-planar - quasi planar phase which has some out-of-plane components
*most probable alignment; less energetically favored would be a quasi homeotropic phase
Semi - means semitransparent due to out-of-plane components
The combinations of LC-p and LC-n refer to positive or negative dielectric anisotropy of liquid crystal, respectively, whereas the combinations of G-p and G-n refer to positive or negative optical anisotropy of the guest dye molecule, respectively The directors correspond to the axes of the coordinate system illustrated in FIGS. 14A and 15A Reference is now made to FIG. 16, which is a schematic illustration in perspective of a protective layer, generally referenced 720, of a variable polarizer, constructed and operative in accordance with a further embodiment of the disclosed technique. Protective layer 720 is divided into a plurality of sections 722, 724 and 726.

A pair of electrodes 728 and 730 are etched on section 722. A pair of electrodes 732 and 734 are etched on section 724. A pair of electrodes 736 and 738 are etched on section 726. A voltage $V_4$ is applied across electrodes 728 and 730. A voltage $V_5$ is applied across electrodes 732 and 734. A voltage $V_6$ is applied across electrodes 736 and 738. When protective layer 720 is incorporated in a variable polarizer (not shown), similar to variable polarizer 630 (FIG. 14A), voltages $V_4$, $V_5$ and $V_6$ can be controlled individually, such that each section of the variable polarizer (such as sections 722, 724 and 726), applies a different polarization level to the incident light.

A protective layer similar to protective layer 720 can be incorporated in a variable polarizer similar to variable polarizer 670, wherein a protective layer similar to protective layer 674 includes a plurality of separate planar electrodes similar to planar electrode 692. The controller switches electric power to one pair of electrodes similar to electrodes 728 and 730 on one hand and a respective planar electrode on the other hand, thereby enabling the variable polarizer to apply a polarization level to the incident light at the respective section thereof, similar to section 722. In this case too, the variable polarizer can be operated either in the in-plane mode or the parallel-plane mode.

It will be appreciated by persons skilled in the art that the present invention is not limited to what has been particularly shown and described herein above. Rather the scope of the present invention is defined only by the claims, which follow.

The invention claimed is:

1. A device for transmitting light at variable intensity, the device comprising:

a front variable polarizer, polarizing incoming light at a first selected polarization level in a first direction;

a rear variable polarizer, optically coupled with said front variable polarizer, polarizing light exiting said front variable polarizer at a second selected polarization level, in a second direction; and at least one of the front variable polarizer and the rear variable polarizer includes a mixed homeotropic and planar surface alignment material, wherein the mixed homeotropic and planar surface alignment material includes rod-shaped molecules that in the homeotropic state align substantially in one direction and in the planar state align substantially in another direction;

wherein said first selected polarization level and said second selected polarization level are substantially zero, when no substantial electric power is applied respectively, to said front variable polarizer and said rear variable polarizer.

2. The device according to claim 1, wherein said first selected polarization level is selected by controlling the electric field at said front variable polarizer.

3. The device according to claim 1, wherein said second selected polarization level is selected by controlling the electric field at said rear variable polarizer.

4. The device according to claim 1, wherein each of said first selected polarization level and said second selected polarization level is selected by setting said front variable polarizer and said rear variable polarizer, respectively, to one of a plurality of states.

5. The device according to claim 4, wherein said states comprise at least one homeotropic state.

6. The device according to claim 4, wherein said states comprise at least one planar state.

7. The device according to claim 4, wherein said states comprise at least one state wherein at least one of said first selected polarization level and said second selected polarization level is substantially zero.

8. The device according to claim 1, wherein at least one of said front variable polarizer and said rear variable polarizer is a multi-stable liquid crystal device.

9. The device according to claim 1, wherein each of said front variable polarizer and said rear variable polarizer comprises a light affecting substance, said light affecting substance comprises:

an optically active substance; and a plurality of anisotropic light absorbing particles,
wherein said light affecting substance polarizes said incoming light according to the direction of said anisotropic light absorbing particles.

10. The device according to claim 9, wherein the dielectric anisotropy of said optically active substance is selected from the list consisting of:
positive; and
negative.

11. The device according to claim 9, wherein the optical anisotropy of said anisotropic light absorbing particles is selected from the list consisting of;
positive; and
negative.

12. The device according to claim 9, wherein said optically active substance is selected from the list consisting of:
liquid crystal;
liquid crystal polymer;
bireferingent crystal;
bireferingent polymer; and
bireferingent plastic.

13. The device according to claim 9, wherein said anisotropic light absorbing particles are selected from the list consisting of:
dichroic dye molecules;
dichroic microcrystals; and
pleochroic dye stuff.

14. The device according to claim 9, wherein said anisotropic light absorbing particles are distributed within said optically active substance, in a phrase distribution selected from the list consisting of:
dispersed; and
homogeneous.

15. The device according to claim 14, wherein each of said dispersed phase distribution and said homogeneous phase distribution, is in a form selected from the list consisting of:
mixture; and
chemical compound.

16. The device according to claim 14, wherein said homogeneous phase distribution is derived from liquid crystal materials and phases selected from the list consisting of:
nematic;
twisted nematic;
supertwisted nematic;
cholesteric;
smectic;
multi-stable; and
a combination of the above.

17. The device according to claim 14, wherein said dispersed phase distribution is derived from liquid crystal materials and phases selected from the list consisting of:
Guest-Host Polymer Dispersed Liquid Crystal;
Dichroic Polymer Dispersed Liquid Crystal;
Polymer Stabilized Cholesteric Texture Liquid Crystal;
Surface Stabilized Cholesteric Texture Liquid Crystal; and
Nematic Curved Aligned Polymeric Liquid Crystal.

18. The device according to claim 14, wherein has a non-spherical anisotropic geometry selected from the list consisting of:
elliptical;
elongated;
sheared; and
a combination of the above.

19. The device according to claim 14, wherein the refractive index anisotropy of said dispersed phase distribution, between the ordinary index of said dispersed phase distribution and the extraordinary index of said dispersed phase distribution, is sufficiently small, that each of said front variable polarizer and said rear variable polarizer polarizes incident light without substantially scattering said incident light.

20. The device according to claim 1, wherein the plane defined by said device is selected from the list consisting of:
flat;
concave;
convex; and
curved.

21. The device according to claim 1, wherein the type of said device is selected from the list consisting of:
rigid; and
flexible.

22. The device according to claim 1, wherein said first direction is substantially perpendicular to said second direction.

23. The device according to claim 1, wherein said first selected polarization level and said second selected polarization level are selected by controlling the electric field at said front variable polarizer and at said rear variable polarizer, respectively.

24. The device according to claim 1, wherein setting said front variable polarizer and said rear variable polarizer to said first polarization level and said second polarization level, respectively, determines the contrast and brightness of an image produced by said device.

25. The device according to claim 1, further comprising a controller, controlling at least one of said variable polarizer and said rear variable polarizer.

26. The device according to claim 25, wherein said controller is coupled with said front variable polarizer,
wherein said front variable polarizer is divided into a plurality of sections, and
wherein said controller sets each of said sections to a respective polarization level.

27. The device according to claim 25, wherein said controller is coupled with said rear variable polarizer,
wherein said rear variable polarizer is divided into a plurality of rear end sections, and
wherein said controller sets each of said rear end sections to a respective polarization level.

28. The device according to claim 27, wherein said controller is further coupled with said front variable polarizer,
wherein said front variable polarizer is divided into a plurality of front end sections, said front end sections being compatible with said rear end sections, and
wherein said controller sets each of said front end sections to another respective polarization level.

29. The device according to claim 25, further comprising at least one light detector, coupled with said controller, wherein said at least one light detector provides at least one light-intensity value.

30. The device according to claim 29, wherein said at least one light value is produced according to a meeting scheme selected from the list consisting of:
spot;
center-weighted;
multi-zone; and
ambient.

31. The device according to claim 29, wherein said controller sets said front variable polarizer and said rear variable polarizer to said first selected polarization level and to said second selected polarization level, respectively, according to said at least one light-intensity value.

32. The device according to claim 29, wherein at least one of said at least one light detector is a active-region light detector, respective of an active region of interest.

33. The device according to claim 29, wherein at least one of said at least one light detector is a passive-region light detector, respective of a passive region of interest.

34. The device according to claim 29, wherein said controller, at least one of said at least one light detector, said front variable polarizer and said rear variable polarizer are coupled together in a control system loop.

35. The device according to claim 1, wherein said front variable polarizer comprises:
- a first protective layer;
- a second protective layer;
- a first pair of multi-pronged electric conductors located between said first protective layer and said second protective layer, a first set of prongs of said first pair lying along a first multi-prong direction, said first set of prongs being intermingled; and
- a light affecting substance said light affecting substance comprises;
- an optically active substance; and
- a plurality of anisotropic light absorbing particles being substantially aligned with the molecules of said optically active substance, wherein said rear variable polarizer comprises;
- a third protective layer;
- a fourth protective layer;
- a second pair of multi-pronged electric conductors located between said third protective layer and said fourth protective layer, a second set of prongs of said second pair lying along a second multi-prong direction, said first multi-prong direction being rotated by substantially ninety degrees relative to said second multi-prong direction, said second set of prongs being intermingled, and
- another light affecting substance similar to said light affecting substance, wherein said optically active substance is aligned along said first direction, when said electric power is applied to said first pair, thereby said anisotropic light absorbing particles polarizing said incoming light at a first powered condition polarization level, and wherein said other optically active substance is aligned along said second direction, when said electric power is applied to said second pair, thereby said anisotropic light absorbing particles polarizing said incoming light at a first powered condition polarization level.

36. The device according to claim 35, wherein said front variable polarizer further comprises a first alignment layer located between said first protective layer and said second protective layer, said first pair being located between said first protective layer and said first alignment layer, said first alignment layer affecting a molecular direction of said molecules, such that when substantially no electric power is applied to said first pair, said anisotropic light absorbing particles polarize said incoming light at an un-powered condition polarization level, and wherein said rear variable polarizer further comprises a second alignment layer located between said third protective layer and said fourth protective layer, said second pair being located between said third protective layer and said second alignment layer, said second alignment layer affecting said molecular direction, such that when substantially no electric power is applied to said second pair, said anisotropic light absorbing particles polarize said incoming light at said un-powered condition polarization level.

37. The device according to claim 36, wherein each of said first alignment layer and second alignment layer is selected from the list consisting of:
- homeotropic;
- planar;
- inorganic dielectric; and
- organic dielectric.

38. The device according to claim 35, wherein said front variable polarizer further comprises:
- a first insulating layer located between said first protective layer and said second protective layer, said first pair being located between said first protective layer and said first insulating layer; and
- a first electrically conducting layer located between said first insulating layer and said second protective layer, wherein said rear variable polarizer further comprises:
- a second insulating layer located between said third protective layer and said forth protective layer, said second pair being located between said third protective layer and said second insulating layer; and
- a second electrically conducting layer located between said second insulating layer and said fourth protective layer, wherein said optically active substance is aligned along said first direction, when said electric power is applied to said first pair and to said first electrically conducting layer, and wherein said optically active substance is aligned along said second direction, when said electric power is applied to said second pair and to said second electrically conducting layer.

39. The device according to claim 38, wherein said front variable polarizer further comprises:
- a third insulating layer located between said first insulating layer and said first pair; and
- a first alignment layer located between said first insulating layer and said third insulating layer, said first alignment layer affecting a molecular direction of said molecules, such that when substantially no electric power is applied to said first pair and to said first electrically conducting layer, said anisotropic light absorbing particles polarize said incoming light at an un-powered condition polarization level, and wherein said rear variable polarizer further comprises;
- a fourth insulating layer located between said second insulating layer and said second pair; and
- a second alignment layer located between said second insulating layer and said fourth insulating layer, said second alignment layer affecting said molecular direction, such that when substantially no electric power is applied to said second pair and to said second electrically conducting layer, said anisotropic light absorbing particles polarize said incoming light at said un-powered condition polarization level.

40. The variable polarizer according to claim 38, wherein said first pair, said second pair, said first electrically conducting layer, and said second electrically conducting layer are coupled with a power source and with a controller, wherein said controller controls said electric power across said first pair and said first electrically conducting layer on one hand and said second pair and said second electrically conducting layer on the other hand, and wherein said anisotropic light absorbing particles polarize said incoming light at said first powered condition polarization level, in a first region of said front variable polarizer corresponding to said first pair and to said first electrically conducting layer, and said other anisotropic light absorbing particles polarize said incoming light at said second powered condition polarization level, in a second region of said rear variable polarizer corresponding to said second pair and to said second electrically conducting layer.

41. The device according to claim 38, wherein each of said first electrically conducting layer and said second electrically conducting layer is made of substantially thin, transparent and electrically conductive material, selected from the list consisting of:
   conductive polymer;
   glass coated by indium-tin-oxide;
   tin-oxide; and
   metal.

42. The device according to claim 35, wherein each of said first protective layer, said second protective layer, said third protective layer, and said fourth protective layer is made of a substantially transparent material selected from the list consisting of:
   glass;
   crystal;
   polymer; and
   plastic.

43. The device according to claim 35, wherein each of said first pair and said second pair is made of a substantially thin transparent and electrically conductive material, selected from the list of:
   conductive polymer;
   glass coated by indium-tin-oxide;
   tin-oxide; and
   metal.

44. The device according to claim 35, wherein said first pair and said second pair are coupled with a power source and with a controller,
   wherein said controller controls said electric power across said first set of prongs and across said second set of prongs, and
   wherein said anisotropic light absorbing particles polarize said incoming light at said first powered condition polarization level, in a first region of said front variable polarizer corresponding to said first pair, and at said second powered condition polarization level, in a second region of said rear variable polarizer corresponding to said second pair, when said electric power is applied across said first of prongs and across said second set of prongs.

45. A method for transmitting light at variable intensity, the method comprising the procedures of:
   polarizing light, at a first selected polarization level, by a front variable polarizer;
   polarizing said light, at a second selected polarization level, by a rear variable polarizer; and
   providing in at least one of the front variable polarizer and the rear variable polarizer a mixed homeotropic and planar surface alignment material, wherein the mixed homeotropic and planar surface alignment material includes rod-shaped molecules that in the homeotropic state align substantially in one direction and in the planar state align substantially in another direction;
   wherein said first selected polarization level and said second polarization levels are substantially zero, when no substantial power is available.

46. The device according to claim 45, further comprising a preliminary procedure of controlling the electric field at least one of said front variable polarizer and said rear variable polarizer, thereby selecting at least one of said first selected polarization level and said second selected polarization level, respectively.

47. The method according to claim 46, wherein at least one of said first selected polarization level and said second selected polarization level is selected according to at least one light-intensity value.

48. The method according to claim 45, further comprising a preliminary procedure of detecting the intensity of light, thereby providing at least one light-intensity value.

49. The method according to claim 48, wherein said procedure of detecting comprises the sub-procedure of detecting the intensity of active-region light, thereby providing at least one active-region light-intensity value.

50. The method according to claim 48, wherein said procedure of detecting comprises the sub-procedure of detecting the intensity of passive-region light, thereby providing at least one passive-region light-intensity value.

51. An apparatus for viewing an image at variable intensity, the apparatus comprising:
   an optical assembly;
   a variable transmitter, said variable transmitter including:
   a front variable polarizer;
   a rear variable polarizer, optically coupled with said front variable polarizer; and
   at least one of the front variable polarizer and the rear variable polarizer includes a mixed homeotropic and planar surface alignment material, wherein the mixed homeotropic and planar surface alignment material includes rod-shaped molecules that in the homeotropic state align substantially in one direction and in the planar state align substantially in another direction;
   wherein said front variable polarizer applies substantially no polarization to an incoming light and transmits said incoming light as an outgoing light, when a first change in an electric field is applied to said front variable polarizer,
   wherein said front variable polarizer polarizes said incoming light in a first direction, thereby producing a polarized incoming light, when a second change in said electric field is applied to said front variable polarize,
   wherein said rear variable polarizer applies substantially no polarization to said outgoing light, when said first change is applied to said rear variable polarizer, and
   wherein said rear variable polarizer said polarized incoming light in a second direction, when said second change is applied to said rear variable polarizer.

52. The apparatus according to claim 51, wherein said optical assembly is selected from the list consisting of:
   spectacles;
   helmet visor;
   welding visor;
   periscope;
   telescope;
   microscope;
   binoculars;
   ground vehicle window;
   aircraft window;
   spacecraft window;
   marine vehicle window;
   grazing;
   greenhouse window.

53. Device for transmitting light at variable intensity, the device comprising:
   a front variable polarizer, polarizing incoming light at a first selected polarization level in a first direction; and
   a rear variable polarizer, optically coupled with said front variable polarizer, polarizing light exiting said front variable polarizer at a second selected polarization level, in a second direction, wherein said first selected polarization level and said second selected polarization level are substantially zero, when no substantial electric power is applied respectively, to said front variable polarizer and said rear variable polarizer; and wherein each of said front variable polarizer and said rear variable polarizer comprises a light affecting substance, said light affecting substance comprising an optically active substance and a plurality of anisotropic light absorbing particles, wherein said light affecting substance polarizes said incoming light according to the direction of said anisotropic light absorbing particles, a controller for controlling at least one of said front variable polarizer and said rear variable polarizer, said controller being coupled with said front variable polarizer which is divided into a plurality of sections and said controller sets each of said sections to a respective polarization level and said controller is also coupled with said rear variable polarizer which also is divided into a plurality of rear end sections, and said controller sets each of said rear end sections to a respective polarization level, wherein said front variable polarizer further comprises:

a first protective layer;

a second protective layer;

a first pair of multi-pronged electric conductors located between said first protective layer and said second protective layer, a first set of prongs of said first pair lying along a first multi-prong direction, said first set of prongs being intermingled; and a light affecting substance said light affecting substance comprises;

an optically active substance; and a plurality of anisotropic light absorbing particles being substantially aligned with the molecules of said optically active substance, wherein said rear variable polarizer further comprises;

a third protective layer;

a fourth protective layer;

a second pair of multi-pronged electric conductors located between said third protective layer and said fourth protective layer, a second set of prongs of said second pair lying along a second multi-prong direction, said first multi-prong direction being rotated by substantially ninety degrees relative to said second multi-prong direction, said second set of prongs being intermingled, and another light affecting substance similar to said light affecting substance, wherein said optically active substance is aligned along said first direction, when said electric power is applied to said first pair, thereby said anisotropic light absorbing particles polarizing said incoming light at a first powered condition polarization level, and wherein said other optically active substance is aligned along said second direction, when said electric power is applied to said second pair, thereby said anisotropic light absorbing particles polarizing said incoming light at a first powered condition polarization level.

54. The device according to claim 53 wherein the dielectric anisotropy of said optically active substance is selected from the list consisting of:

positive and negative.

55. The device according to claim 53 wherein said front variable polarizer is divided into a plurality of front end sections, said front end sections being compatible with said rear end sections, and wherein said controller sets each of said front end sections to another respective polarization level.

56. The device according to claim 53, wherein said front variable polarizer further comprises a first alignment layer located between said first protective layer and said second protective layer, said first pair being located between said first protective layer and said first alignment layer, said first alignment layer affecting a molecular direction of said molecules, such that when substantially no electric power is applied to said first pair, said anisotropic light absorbing particles polarize said incoming light at an un-powered condition polarization level, and wherein said rear variable polarizer further comprises a second alignment layer located between said third protective layer and said fourth protective layer, said second pair being located between said third protective layer and said second alignment layer, said second alignment layer affecting said molecular direction, such that when substantially no electric power is applied to said second pair, said anisotropic light absorbing particles polarize said incoming light at said un-powered condition polarization level.

57. The device according to claim 53, wherein said front variable polarizer further comprises:

a first insulating layer located between said first protective layer and said second protective layer, said first pair being located between said first protective layer and said first insulating layer; and a first electrically conducting layer located between said first insulating layer and said second protective layer, wherein said rear variable polarizer further comprises:

a second insulating layer located between said third protective layer and said forth protective layer, said second pair being located between said third protective layer and said second insulating layer; and a second electrically conducting layer located between said second insulating layer and said fourth protective layer, wherein said optically active substance is aligned along said first direction, when said electric power is applied to said first pair and to said first electrically conducting layer, and wherein said optically active substance is aligned along said second direction, when said electric power is applied to said second pair and to said second electrically conducting layer.

* * * * *